(12) United States Patent
Lin et al.

(10) Patent No.: US 11,912,650 B2
(45) Date of Patent: Feb. 27, 2024

(54) BAKUCHIOL DERIVATIVES, PHARMACEUTICALLY ACCEPTABLE SALTS THEREOF, AND PREPARATION METHOD AND USE OF THE SAME

(71) Applicant: JIANGXI SHIMEI PHARMACEUTICAL CO., LTD., Jiangxi (CN)

(72) Inventors: Shuimu Lin, Guangzhou (CN); Shouping Liu, Guangzhou (CN); Hongxia Li, Guangzhou (CN); Hong Jiang, Fuzhou (CN)

(73) Assignee: JIANGXI SHIMEI PHARMACEUTICAL CO., LTD, Fuzhou (CN)

( * ) Notice: Subject to any disclaimer, the term of this patent is extended or adjusted under 35 U.S.C. 154(b) by 0 days.

(21) Appl. No.: 18/033,414

(22) PCT Filed: Oct. 30, 2020

(86) PCT No.: PCT/CN2020/125481
§ 371 (c)(1),
(2) Date: Apr. 24, 2023

(87) PCT Pub. No.: WO2022/088091
PCT Pub. Date: May 5, 2022

(65) Prior Publication Data
US 2023/0391717 A1    Dec. 7, 2023

(30) Foreign Application Priority Data

Oct. 26, 2020   (CN) .......................... 202011152645.9

(51) Int. Cl.
C07C 279/14        (2006.01)
C07D 263/38        (2006.01)

(52) U.S. Cl.
CPC .......... *C07C 279/14* (2013.01); *C07D 263/38* (2013.01); *C07C 2601/16* (2017.05)

(58) Field of Classification Search
CPC ............................. C07C 279/14; C07D 263/38
See application file for complete search history.

(56) References Cited

U.S. PATENT DOCUMENTS

| 9,957,247 B2 | 5/2018 | Wang et al. |
| 2015/0152077 A1 | 6/2015 | Wang et al. |
| 2015/0238401 A1 | 8/2015 | Yoshioka et al. |
| 2018/0222880 A1 | 8/2018 | Wang et al. |

FOREIGN PATENT DOCUMENTS

| CN | 104755452 A | 7/2015 |
| CN | 104870438 A | 8/2015 |
| WO | 2005/033065 A1 | 4/2005 |
| WO | 2008/062436 A2 | 5/2008 |
| WO | 2020/149295 A1 | 7/2020 |

OTHER PUBLICATIONS

Jun. 24, 2021 International Search Report issued in International Patent Application No. PCT/CN2020/125481.
Jun. 24, 2021 Written Opinion issued in International Patent Application No. PCT/CN2020/125481.
Apr. 14, 2022 Office Action issued in Chinese Patent Application No. 202011152645.9.
Jul. 20, 2022 Office Action issued in Chinese Patent Application No. 202011152645.9.

*Primary Examiner* — Sikarl A Witherspoon
(74) *Attorney, Agent, or Firm* — Oliff PLC

(57) ABSTRACT

A bakuchiol derivative, a pharmaceutically acceptable salt thereof, and a preparation method and use of the same. The bakuchiol derivative has a structure shown in formula (I):

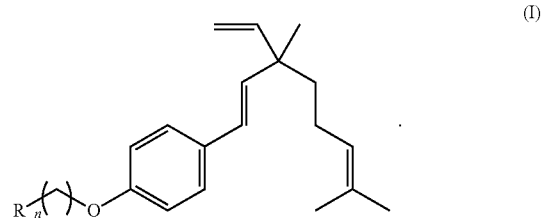

The above series of amphiphilic antibacterial compounds based on bakuchiol have comparatively excellent antibacterial activities and can overcome the generation of drug resistance of bacteria in drug resistance research simulated in a laboratory.

9 Claims, 1 Drawing Sheet

BAKUCHIOL DERIVATIVES, PHARMACEUTICALLY ACCEPTABLE SALTS THEREOF, AND PREPARATION METHOD AND USE OF THE SAME

TECHNICAL FIELD

The disclosure relates to the technical field of medicinal chemistry, in particular to bakuchiol derivatives, pharmaceutically acceptable salts thereof, and a preparation method and use of the same.

BACKGROUND

At present, infectious diseases have become the main cause of human death in the world, and multidrug-resistant bacteria are one of the most common causes of infection death. Antibiotic resistance of bacteria along with a sharp increase in morbidity and mortality and expensive treatment costs poses a serious threat to the global public health system. The World Health Organization and many countries have realized that the problem of antibiotic resistance will seriously hinder the control of infectious diseases and endanger human health. However, most pharmaceutical companies have greatly reduced their investment in the research and development of antibacterial agents since the antibacterial agents have a short medication cycle and drug resistance can be easily produced. In the past two decades, the number of approved new antibacterial agents has decreased drastically, especially of those based on new molecular entities. Therefore, there is an urgent need to develop a new antibacterial agent with high efficiency and low toxicity, which can effectively overcome the generation of drug resistance.

SUMMARY

Based on this, it is necessary to provide a bakuchiol derivative, a pharmaceutically acceptable salt thereof, and a preparation method and use of the same.

Provided are a bakuchiol derivative and a pharmaceutically acceptable salt thereof. The bakuchiol derivative has a structure shown in formula (I):

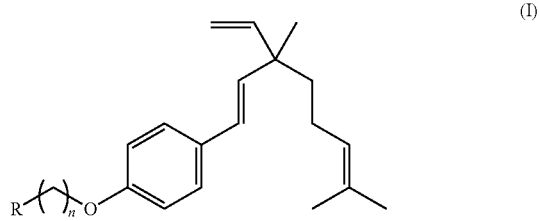

(I)

where n is an integer from 1 to 16;
R is selected from halogens, —$CONR_1R_2$, —$COOR_3$, —$NR_4R_5$,

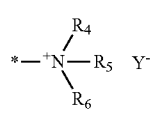

or

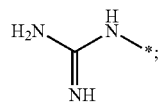

$R_1$ and $R_2$ are each independently selected from: —H,

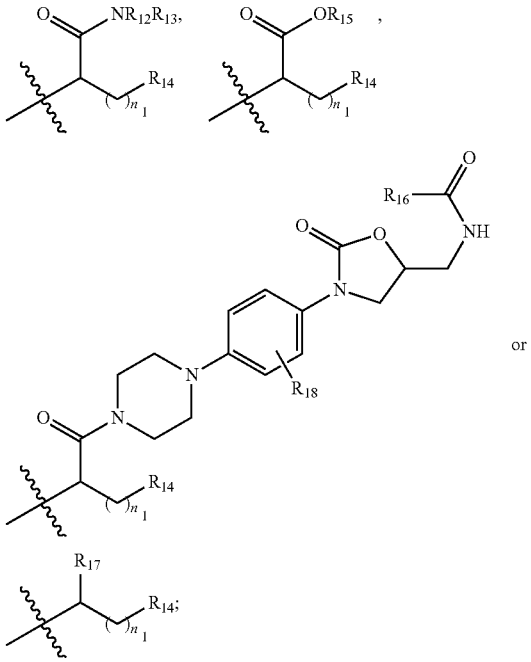

$R_{12}$ and $R_{13}$ are each independently selected from: —H,

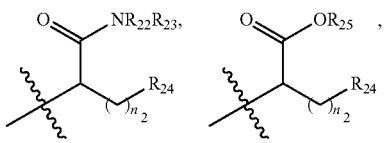

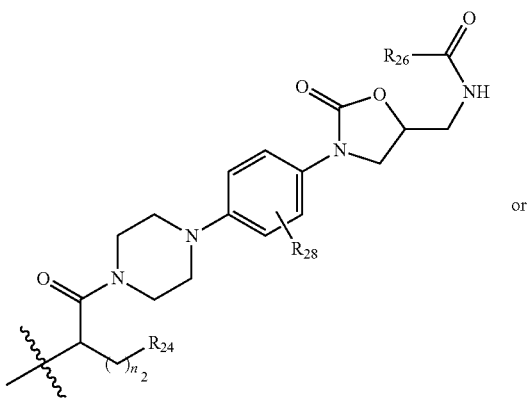

or

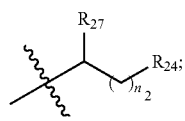
$R_{22}$ and $R_{23}$ are each independently selected from: —H,
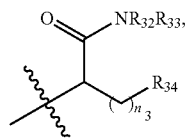 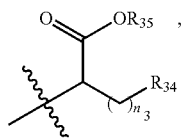
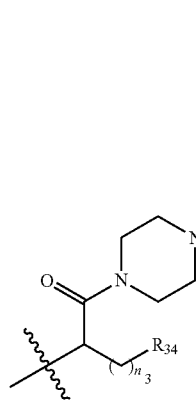
or
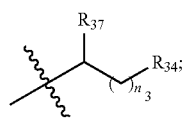
$R_{32}$ and $R_{33}$ are each independently selected from: —H,
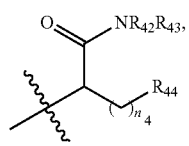 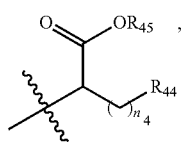
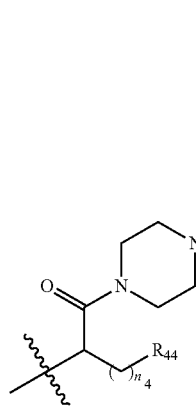
or
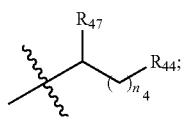
$R_{42}$ and $R_{43}$ are each independently selected from: —H,
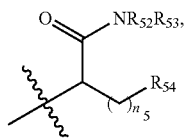 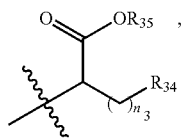
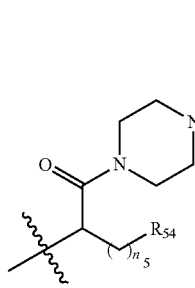
or
 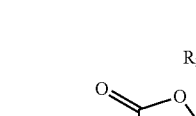
$R_{52}$ and $R_{53}$ are each independently selected from: —H,
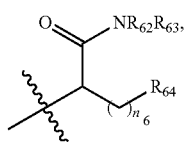 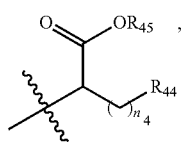
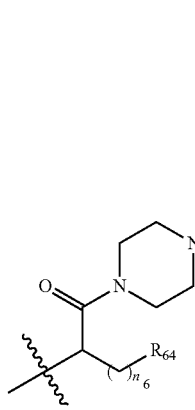 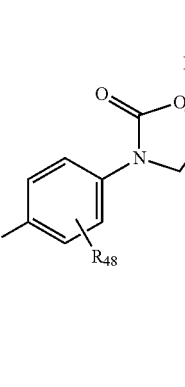
or

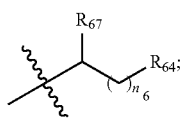

$R_{62}$ and $R_{63}$ are each independently selected from: —H or

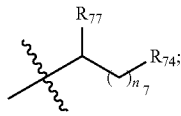

where $R_{14}$, $R_{24}$, $R_{34}$, $R_{44}$, $R_{54}$, $R_{64}$ and $R_{74}$ are each independently selected from: —H, guanidyl, —NR$_4$R$_5$, —SR$_4$, 5- to 20-membered nitrogen-containing heteroaryl,

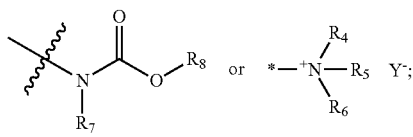

$R_{15}$-$R_{17}$, $R_{25}$-$R_{27}$, $R_{35}$-$R_{37}$, $R_{45}$-$R_{47}$, $R_{55}$-$R_{57}$ and $R_{65}$-$R_{67}$ are each independently selected from: —H or $C_{1-6}$ alkyl;

$R_{18}$, $R_{28}$, $R_{38}$, $R_{48}$, $R_{58}$ and $R_{68}$ are each independently selected from: —H, $C_{1-6}$ alkyl or halogen;

each of $n_1$, $n_2$, $n_3$, $n_4$, $n_5$, $n_6$ and $n_7$ is independently 0, 1, 2, 3, 4, 5, 6, 7, 8, 9 or 10;

$R_{77}$ is selected from: —H or $C_{1-6}$ alkyl;

$R_3$ is selected from: —H or $C_{1-4}$ alkyl;

$R_4$ and $R_5$ are each independently selected from: —H, $C_{1-6}$ alkyl, COOR$_8$, -Fmoc or $R_a$-substituted $C_{1-16}$ alkyl; or $R_4$ and $R_5$ together with N linked thereto may form a 5- to 20-membered heterocyclic ring, a 5- to 20-membered heteroaromatic ring, a 5- to 20-membered heterocyclic ring substituted by $R_b$ or a 5- to 20-membered heteroaromatic ring substituted by $R_b$;

$R_a$ is selected from: 5- to 10-membered aryl, 5- to 10-membered heteroaryl, —NR$_{a1}$R$_{a2}$ or —SR$_{a3}$;

$R_b$ is selected from: $C_{1-10}$ alkyl, —(CH$_2$)$_p$NR$_{b1}$R$_{b2}$ or —SR$_{b3}$, where p is 0, 1, 2, 3, 4, 5, 6, 7, 8, 9 or 10;

each of $R_{a1}$, $R_{a2}$, $R_{b1}$ and $R_{b2}$ is independently —H, $C_{1-10}$ alkyl or $R_c$-substituted $C_{1-10}$ alkyl; or $R_{a1}$ and $R_{a2}$ together with a N atom linked thereto may form a 5- to 10-membered heterocyclic ring or a 5- to 10-membered heteroaromatic ring; or $R_{b1}$ and $R_{b2}$ together with a N atom linked thereto may form a 5- to 10-membered heterocyclic ring or a 5- to 10-membered heteroaromatic ring;

each of $R_{a3}$ and $R_{b3}$ is independently $C_{1-10}$ alkyl;

$R_c$ is selected from: —NR$_{c1}$R$_{c2}$, guanidyl or 5- to 6-membered nitrogen-containing heteroaryl, where each of $R_{c1}$ and $R_{c2}$ is independently: —H, $C_{1-4}$ alkyl; or $R_{c1}$ and $R_{c2}$ together with a N atom linked thereto may form a 5- to 10-membered heterocyclic ring or a 5- to 10-membered heteroaromatic ring;

$R_6$ is $C_{1-4}$ alkyl; $R_7$ is selected from: —H or $C_{1-4}$ alkyl; $R_8$ is —H, $C_{1-6}$ alkyl or

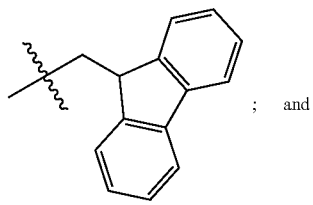 [SMILES: *CC1c2ccccc2-c2ccccc21]

; and

Y— is an anion.

Provided is a preparation method of the above bakuchiol derivative and a pharmaceutically acceptable salt thereof. When R is a halogen, the preparation method includes the following step:

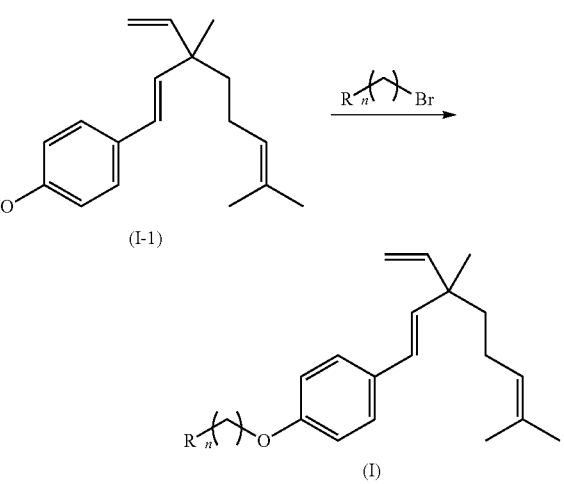

reacting a compound shown in formula (I-1) with

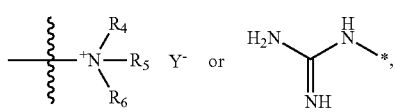

to obtain a compound shown in formula (I-1) with R being a halogen;

when R is NR$_4$R$_5$,

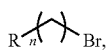

the preparation method includes the following steps:

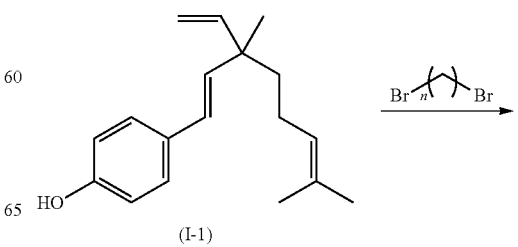

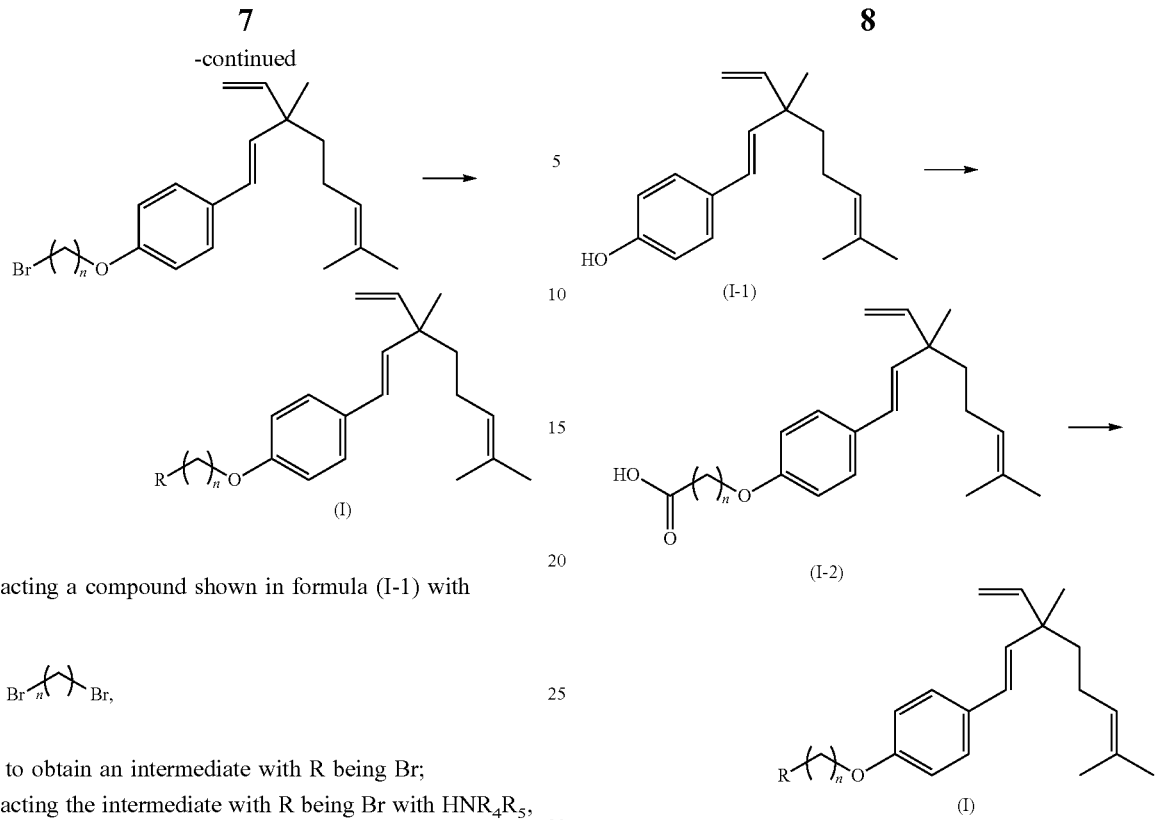

reacting a compound shown in formula (I-1) with

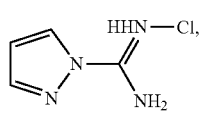

to obtain an intermediate with R being Br;

reacting the intermediate with R being Br with $HNR_4R_5$, to obtain a compound shown in formula (I) with R being $NR_4R_5$;

reacting the compound shown in formula (I) with R being $NR_4R_5$ with haloalkyl, to obtain a compound shown in formula (I) with R being

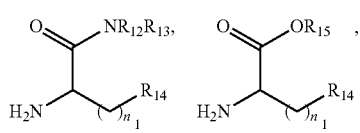

and reacting a compound shown in formula (I) with R being $NH_2$ with

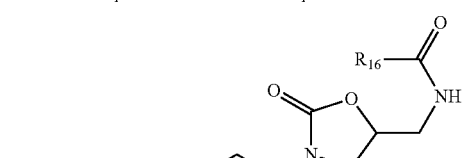

to obtain a compound shown in formula (I) with R being

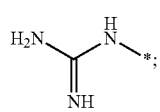

and when R is selected from $CONR_1R_2$ and $—COOR_3$, the preparation method includes the following steps:

performing a condensation reaction on a compound shown in formula (I-1) and an alkyl bromoalkylate, to obtain a compound shown in formula (I) with R being $—COOR_3$;

hydrolyzing to obtain a compound shown in formula (I-2); and performing a condensation reaction on the compound shown in formula (I-2) and

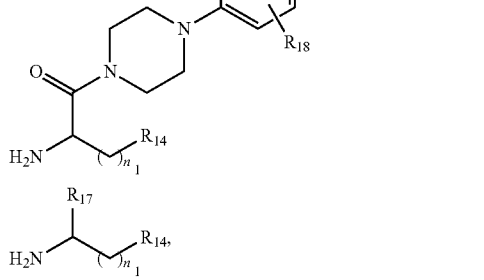

to obtain a compound shown in formula (I) with R being $CONR_1R_2$.

Provided is a pharmaceutical composition including at least one of the above bakuchiol derivative and a pharmaceutically acceptable salt thereof, and a pharmaceutically acceptable excipient.

Provided is use of the above bakuchiol derivative and a pharmaceutically acceptable salt thereof or the above pharmaceutical composition in preparation of antibacterial agents.

Provided is use of the above bakuchiol derivative and a pharmaceutically acceptable salt thereof or the above pharmaceutical composition in preparation of drugs for treating or preventing diseases caused by bacterial infection.

Provided is use of the above bakuchiol derivative and a pharmaceutically acceptable salt thereof or the above pharmaceutical composition in preparation of drugs for treating or preventing infectious diseases.

Provided is a method for treating or preventing bacterial infection, including administration of an effective amount of the above bakuchiol derivative and a pharmaceutically acceptable salt thereof or the above pharmaceutical composition.

The disclosure designs and synthesizes a series of amphiphilic antibacterial compounds based on bakuchiol, which have comparatively excellent antibacterial activity. Specifically, the bakuchiol derivatives and pharmaceutically acceptable salts thereof exhibit excellent antibacterial activity on both Gram-positive bacteria (including methicillin-resistant Staphylococcus aureus) and Gram-negative bacteria, have good water solubility, show comparatively low cytotoxicity and hemolytic activity on mammalian cells, possess comparatively high membrane selectivity and comparatively favorable druggability, and could overcome the generation of drug resistance of bacteria in drug resistance research simulated in a laboratory.

DETAILED DESCRIPTION

Figure 1:
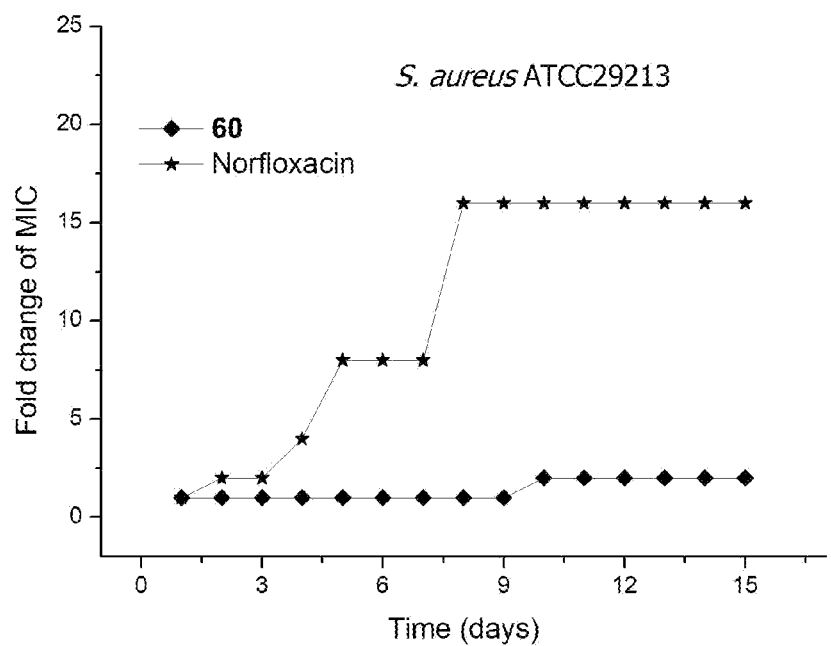
FIG. 1 is a graph showing drug resistance of S. aureus ATCC29213 to a compound 60 and norfloxacin.

In order to facilitate the understanding of the disclosure, the disclosure will be described more comprehensively below, and preferred embodiments of the disclosure will be given. However, the disclosure may be embodied in many different forms, and is not limited to the embodiments described herein. On the contrary, these embodiments are provided to make the understanding of the disclosure of the disclosure more thorough and comprehensive.

Unless defined otherwise, all technical and scientific terms used herein have the same meaning as commonly understood by those skilled in the technical field of the disclosure. The terms used in the description of the disclosure herein are only for the purpose of describing specific embodiments, and are not intended to limit the disclosure. As used herein, the term "and/or" includes any and all combinations of one or more related listed items.

Explanation of Terms

Definitions and General Terms

Unless stated to the contrary, the following terms used in the description and claims have the following meanings.

In the disclosure, the term "optionally substituted by one or more substituents" means being substituted by one or more substituents, or unsubstituted. Specifically, "optional" or "optional" means that an event or environment described subsequently may but does not have to occur, and this description includes occasions when the event or environment occurs or does not occur. For example, "$C_{1-16}$ alkyl is optionally substituted by one or more hydroxyl groups" means that hydroxyl groups may but do not have to exist, and this description includes a situation in which $C_{1-16}$ alkyl is substituted by hydroxyl groups and a situation in which $C_{1-16}$ alkyl is not substituted by hydroxyl groups.

In the disclosure, "may form a ring together with . . . " indicates that this situation may or may not occur. For example, $R_{a1}$ and $R_{a2}$ together with a N atom linked thereto may form a 5- to 10-membered heterlcyclic ring, indicating that $R_{a1}$ and $R_{a2}$ together with a N atom linked thereto may form a 5- to 10-membered heterlcyclic ring and may not form a 5- to 10-membered heterlcyclic ring.

"Alkyl" refers to a saturated aliphatic hydrocarbon group, including straight-chain and branched-chain groups. $C_{1-16}$ alkyl refers to an alkyl group containing 1 to 16 carbon atoms. Non-limiting examples of alkyl in the disclosure include: methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl and 2,3-dimethylbutyl. $C_1$-$C_4$ alkyl refers to an alkyl group containing 1 to 4 carbon atoms. In an embodiment, $C_1$-$C_4$ alkyl is methyl, ethyl, n-propyl, isopropyl, n-butyl, isobutyl, tert-butyl and sec-butyl. Alkyl may be substituted or unsubstituted, and when it is substituted, a substituent may be substituted at any available point of attachment.

The term "alkoxy" refers to a group having —O-alkyl, i.e. an alkyl group as defined above attached to a parent nucleus structure via an oxygen atom. Suitable examples of phrases containing this term include, but not limited to, methoxy (—O—CH$_3$ or —OMe), ethoxy (—O—CH$_2$CH$_3$ or -OEt) and tert-butoxy (—O—C(CH$_3$)$_3$ or -OtBu).

"Heterocyclyl" refers to a saturated or partially unsaturated monocyclic or polycyclic cyclic hydrocarbon substituent, i.e. a ring moiety in which one or more ring atoms are selected from heteroatoms such as nitrogen, oxygen or S(O)$_m$ (where m is an integer from 0 to 2), preferably nitrogen or oxygen heteroatoms, but excluding —O—O—, —O—S— or —S—S—; and the remaining ring atoms are carbon. 5- to 20-membered heterocyclyl refers to a ring containing 5 to 20 ring atoms, at least one of which is a heteroatom. Preferably, the heterocyclyl ring contains 5 to 6 ring atoms, of which 1 to 2 are heteroatoms. In an embodiment, heterocyclyl is dihydrofuranyl, tetrahydrofuranyl, pyrrolidinyl, piperidinyl, piperazinyl, morpholinyl, thiomorpholinyl or homopiperazinyl, etc.

"Aryl" refers to an aromatic hydrocarbon group derived by removing a hydrogen atom on the basis of an aromatic ring compound, which may be monocyclic aryl, fused aryl or polycyclic aryl. For polycyclic ring species, at least one of them is an aromatic ring system. For example, 5- to 20-membered aryl refers to an aryl group having 5 to 20 ring atoms, and the aryl group is optionally further substituted. Suitable examples of "aryl" in the disclosure include, but not limited to, benzene, biphenyl, naphthalene, anthracene, phenanthrene, perylene, triphenylene and derivatives thereof. It could be understood that a plurality of aryl groups interrupted by short non-aromatic units (for example, <10% of non-H atoms, such as C, N or O atoms), specifically such as acenaphthene, fluorene, or 9,9-diarylfluorene, triarylamine and diarylether systems, should also be included in the definition of aryl.

"Heteroaryl" means that at least one carbon atom is replaced by a non-carbon atom on the basis of aryl, and the non-carbon atom may be a N atom, an O atom, a S atom, etc. For example, "5- to 20-membered heteroaryl" refers to a heteroaryl group having 5 to 20 ring atoms, and the heteroaryl group is optionally further substituted. Suitable examples of "heteroaryl" in the disclosure include, but not limited to, furan, benzofuran, thiophene, benzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, perimidine, quinazoline and quinazolinone.

"Amino" refers to a derivative of ammonia, having structural characteristics of a formula —N(X)$_2$, where each "X" is independently H, substituted or unsubstituted alkyl, substituted or unsubstituted cycloalkyl, substituted or unsubstituted heterocyclyl, etc. Non-limiting types of amino include —NH$_2$, —N(alkyl)$_2$, —NH(alkyl), —N(cycloalkyl)$_2$, —NH(cycloalkyl), —N(heterocyclyl)$_2$, —NH(heterocyclyl), —N(aryl)$_2$, —NH(aryl), —N(alkyl)(aryl), —N(alkyl)(heterocyclyl), —N(cycloalkyl)(heterocyclyl), —N(aryl)(heteroaryl), —N(alkyl)(heteroaryl), etc.

"Halogen" or "halo" refers to F, Cl, Br or I.
Guanidyl refers to

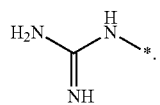

In the disclosure, when the configuration of chiral carbon atoms is not indicated, it should be understood as including any configuration acceptable in the art.

The compounds of the disclosure can exist in non-solvated forms and solvated forms containing pharmaceutically acceptable solvents (such as water, ethanol, etc.), that is, both solvated and non-solvated forms are included.

In the disclosure, a single bond interrupted by a wave " 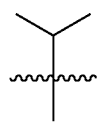 [SMILES: *C(C)C] " represents an attachment position. For example,

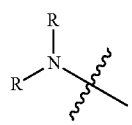

means that carbon at the 2-position of propane is a site of attachment, and means that N is a site of attachment. In the disclosure, * denotes a site of attachment.

In the disclosure, a certain substitutable site may be substituted by one or more substituents, and when there are a plurality of substituents for this substitutable site, the plurality of substituents may be the same as or different from each other.

A "pharmaceutical composition" denotes a mixture containing one or more of the compounds described herein or physiologically/pharmaceutically acceptable salts thereof or prodrugs and other chemical components, as well as additional components. such as physiologically/pharmaceutically acceptable carriers and excipients. The purpose of the pharmaceutical composition is to promote the administration to organisms, facilitate the absorption of active ingredients and further exert biological activity.

The excipients contained in the composition may be one or more buffers, stabilizers, anti-sticking agents, surfactants, wetting agents, lubricants, emulsifiers, adhesives, suspending agents, disintegrating agents, fillers, adsorbents, coating, (intestinal or slow-release) preservatives, antioxidants, opaquing agents, glidants, processing aids, colorants, sweeteners, perfuming agents, flavoring agents and other known additives.

"Pharmaceutically acceptable salt" refers to an organic or inorganic salt of a pharmaceutically acceptable compound.

When the compound is acidic or includes bioelectronic isotopes that are sufficiently acidic, appropriate "pharmaceutically acceptable salts" refer to salts prepared from pharmaceutically acceptable nontoxic bases including inorganic bases and organic bases. The salts are derived from inorganic bases containing aluminum, ammonium, calcium, copper, iron, lithium, magnesium, manganese salts, manganese, potassium, sodium, zinc, etc. Specific examples include ammonium, calcium, magnesium, potassium and sodium salts. The salts are derived from pharmaceutically acceptable organic nontoxic bases. The organic nontoxic bases include salts of primary, secondary and tertiary amines, substituted amines including naturally occurring substituted amines, cyclic amines and basic ion exchange resins such as arginine, betaine, caffeine, choline, N,N'-dibenzylethylenediamine, ethylenediamine, 2-diethylaminoethanol, 2-dimethylaminoethanol, ethanolamine, ethylenediamine, N-ethylmorpholine, N-ethylhexahydropyridine, reduced glucosamine, glucosamine, histidine, hydrabamine, isopropylamine, lysine, meglumine, morpholine, piperazine, piperidine, polyamine resin, procaine, purine, theobromine, triethylamine, trimethylamine, tripropylamine, tromethamine and the like.

When the compound is basic or includes bioelectronic isotopes that are sufficiently basic, salts may be prepared from pharmaceutically acceptable nontoxic acids including inorganic and organic acids. Such acids include acetic acid, benzenesulfonic acid, benzoic acid, camphorsulfonic acid, citric acid, ethanesulfonic acid, fumaric acid, gluconic acid, hydrobromic acid, hydrochloric acid, hydroxyethylsulfonic acid, lactic acid, maleic acid, malic acid, amygdalic acid, methanesulfonic acid, mucic acid, nitric acid, pamoic acid, pantothenic acid, phosphoric acid, sulfuric acid, succinic acid, tartaric acid, p-toluenesulfonic acid and the like. Specific examples include citric acid, hydrobromic acid, hydrochloric acid, phosphoric acid, sulfuric acid, maleic acid and tartaric acid. Other exemplary salts include, but not limited to, sulfate, citrate, acetate, oxalate, chloride, bromide, iodide, nitrate, sulfate, phosphate, superphosphate, isonicotinic acid, lactic acid, salicylate, acid citrate, tartrate, oleate, tannate, pantothenate, bitartrate, ascorbate, succinate, fumarate, maleate, gentisate, gluconate, glucuronate, saccharate, formate, benzoate, glutamate, methanesulfonate, ethanesulfonate, benzenesulfonate, p-toluenesulfonate and pamoate (for example, 1,1'-methylene-bis-(2-hydroxy-3-naphthoate)).

In addition, pharmaceutical preparations containing the compounds may be tablets, capsules, oral liquids, pills, granules, powders, ointments, patches, suppositories, buccal tablets, eye drops, eye ointments, ear drops, sprays, aerosols, inhalants, injections, etc.

The term "therapeutically effective amount" refers to the amount of an effective compound or pharmaceutical agent, which is the minimum amount necessary to improve, cure or treat one or more symptoms of a disease or disorder.

In addition, the compound and the pharmaceutical composition of the disclosure may be administered alone or in combination with other drugs. For combined therapy with more than one active agent, when the active agent exists in divided doses of a preparation, the active agent may be administered individually or in combination. In addition, the administration of one drug may be performed before, at the same time of or after the administration of another drug. During the administration in combination with other drugs, the "effective amount" of a second drug will depend on the type of drug being used.

The compound or the pharmaceutical composition of the disclosure may also be included in a kit.

It should be noted that the agent whose specific source is not indicated in the disclosure is a conventional one available in the market.

DETAILED DESCRIPTION

An embodiment of the disclosure provides a bakuchiol derivative and a pharmaceutically acceptable salt thereof, having a structure shown in formula (I):

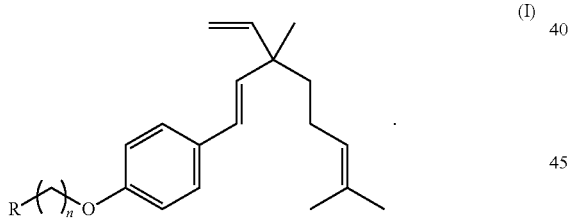

(I)

Further, the bakuchiol derivative and a pharmaceutically acceptable salt thereof have a structure shown in formula (I'):

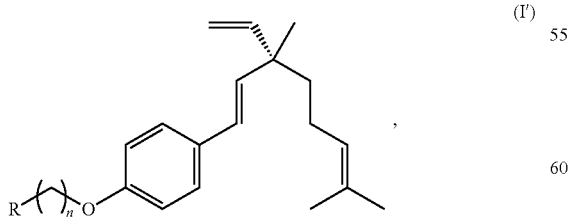

(I')

where n is an integer from 1 to 16. In an embodiment, n is 1, 2, 3, 4, 5, 6, 7, 8, 9, 10, 11 or 12;
R is selected from halogen, $CONR_1R_2$, $-COOR_3$, $NR_4R_5$,

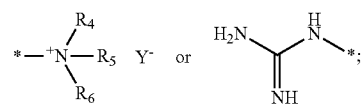

$R_1$ and $R_2$ are each independently selected from: —H,

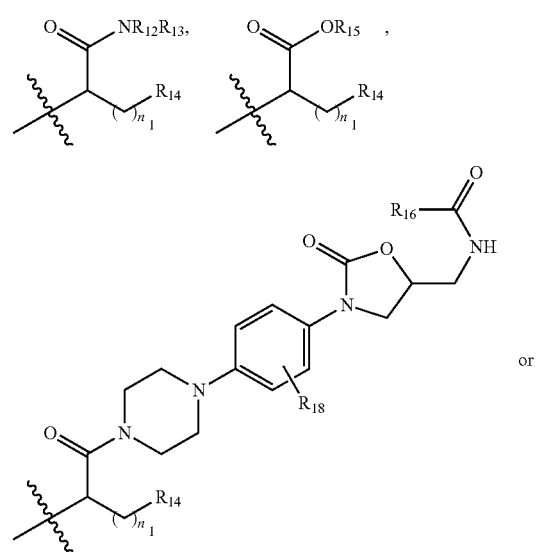

or

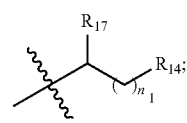

;

$R_{12}$ and $R_{13}$ are each independently selected from: —H,

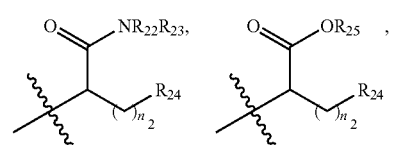

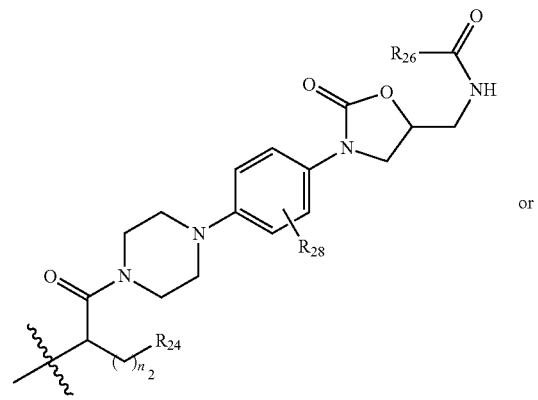

or

-continued
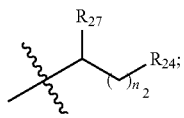
$R_{22}$ and $R_{23}$ are each independently selected from: —H,
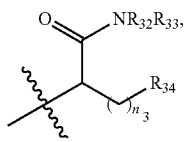
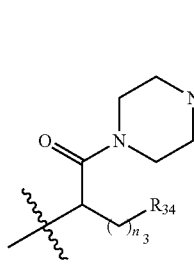
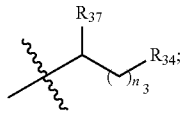
$R_{32}$ and $R_{33}$ are each independently selected from: —H,
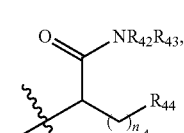
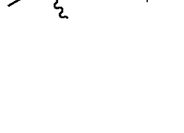
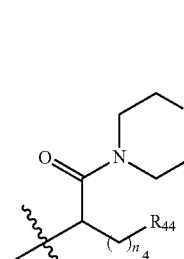
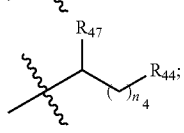
$R_{42}$ and $R_{43}$ are each independently selected from: —H,
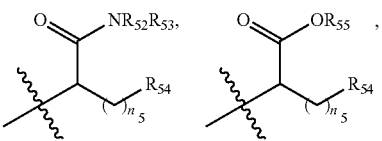
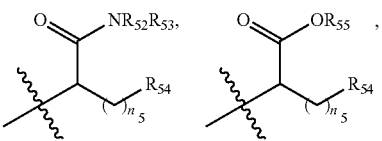
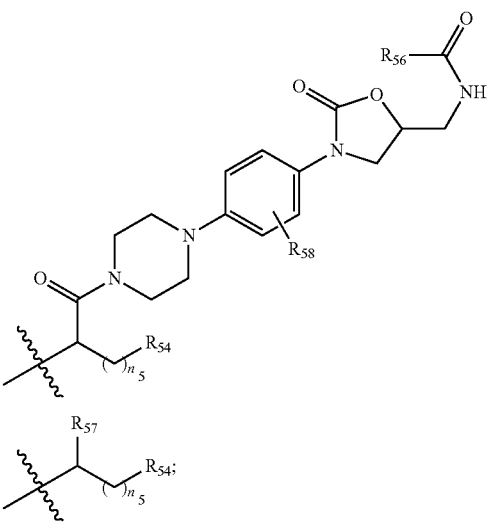
or
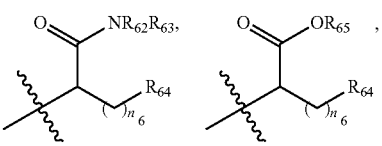
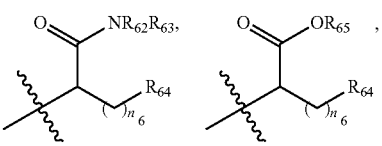
$R_{52}$ and $R_{53}$ are each independently selected from: —H,
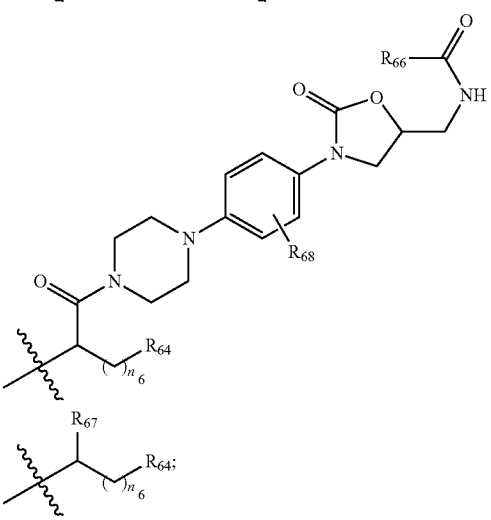
or
$R_{62}$ and $R_{63}$ are each independently selected from: —H or
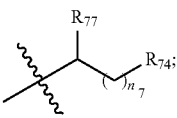

where $R_{14}$, $R_{24}$, $R_{34}$, $R_{44}$, $R_{54}$, $R_{64}$ and $R_{74}$ are each independently selected from: —H, guanidyl, —$NR_4R_5$, —$SR_4$, 5- to 20-membered nitrogen-containing heteroaryl,

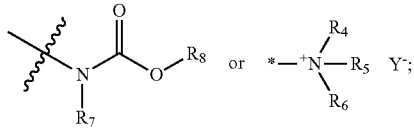

$R_{15}$-$R_{17}$, $R_{25}$-$R_{27}$, $R_{35}$-$R_{37}$, $R_{45}$-$R_{47}$, $R_{55}$-$R_{57}$ and $R_{65}$-$R_{67}$ are each independently selected from: —H or $C_{1-6}$ alkyl;

$R_{18}$, $R_{28}$, $R_{38}$, $R_{48}$, $R_{58}$ and $R_{68}$ are each independently selected from: —H, $C_{1-6}$ alkyl or halogen;

each of $n_1$, $n_2$, $n_3$, $n_4$, $n_5$, $n_6$ and $n_7$ is independently 0, 1, 2, 3, 4, 5, 6, 7, 8, 9 or 10;

$R_{77}$ is selected from: —H or $C_{1-6}$ alkyl;

$R_3$ is selected from: —H or $C_{1-4}$ alkyl;

$R_4$ and $R_5$ are each independently selected from: —H, $C_{1-6}$ alkyl, $COOR_8$, -Fmoc or $R_a$-substituted $C_{1-16}$ alkyl; or $R_4$ and $R_5$ together with N linked thereto may form a 5- to 20-membered heterocyclic ring, a 5- to 20-membered heteroaromatic ring, a 5- to 20-membered heterocyclic ring substituted by $R_b$ or a 5- to 20-membered heteroaromatic ring substituted by $R_b$;

$R_a$ is selected from: 5- to 10-membered aryl, 5- to 10-membered heteroaryl, —$NR_{a1}R_{a2}$ or —$SR_{a3}$;

$R_b$ is selected from: $C_{1-10}$ alkyl, —$(CH_2)_pNR_{b1}R_{b2}$ or —$SR_{b3}$, where p is 0, 1, 2, 3, 4, 5, 6, 7, 8, 9 or 10;

each of $R_{a1}$, $R_{a2}$, $R_{b1}$ and $R_{b2}$ is independently —H, $C_{1-10}$ alkyl or $R_c$-substituted $C_{1-10}$ alkyl; or $R_{a1}$ and $R_{a2}$ together with a N atom linked thereto may form a 5- to 10-membered heterocyclic ring or a 5- to 10-membered heteroaromatic ring; or $R_{b1}$ and $R_{b2}$ together with a N atom linked thereto may form a 5- to 10-membered heterocyclic ring or a 5- to 10-membered heteroaromatic ring;

each of $R_{a3}$ and $R_{b3}$ is independently $C_{1-10}$ alkyl;

$R_c$ is selected from: —$NR_{c1}R_{c2}$, guanidyl or 5- to 6-membered nitrogen-containing heteroaryl, where each of $R_{c1}$ and $R_{c2}$ is independently: —H, $C_{1-4}$ alkyl; or $R_{c1}$ and $R_{c2}$ together with a N atom linked thereto may form a 5- to 10-membered heterocyclic ring or a 5- to 10-membered heteroaromatic ring;

$R_6$ is $C_{1-4}$ alkyl; $R_7$ is selected from: —H or $C_{1-4}$ alkyl; $R_8$ is —H, $C_{1-6}$ alkyl or

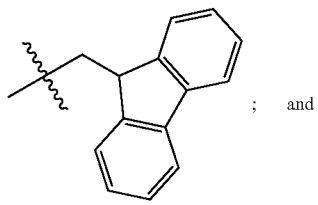 [SMILES: *CC1c2ccccc2-c2ccccc21]

; and $Y-$ is an anion. Furthermore, $Y-$ is a halogen anion. Furthermore, $Y-$ is an iodide ion.

In the disclosure, bakuchiol used as a starting material is prepared into a series of amphiphilic cationic bakuchiol compounds. Bakuchiol contains a hydrophobic skeleton consisting of a benzene ring and an isopentenyl lipid chain, and has good antibacterial activity on gram-positive bacteria. By introducing different cationic groups into the molecular skeleton of bakuchiol, a series of cationic amphiphilic bakuchiol compounds may be synthesized as small molecular antibacterial peptide mimetics. Cationic groups introduced into bakuchiol derivatives may enhance the interaction between the bakuchiol derivatives and negatively charged bacterial cell membranes through electrostatic interaction, and its hydrophobic portions may be inserted into phospholipid bilayers of the bacterial cell membranes through hydrophobic interaction, thereby destroying the integrity of the bacterial cell membranes, leading to the leakage of cell contents and eventually leading to death of bacteria. the structure of the bakuchiol derivatives is systematically optimized to obtain a series of new antibacterial agents with high efficiency and low toxicity, which have membrane targeting or multi-targeting properties and could overcome the generation of drug resistance of bacteria.

Further, $R_3$ is selected from: H, methyl, ethyl or isopropyl.

Further, $R_4$ and $R_5$ are each independently selected from: H, Cl-12 alkyl, $COOR_8$, -Fmoc and $R_a$-substituted $C_{1-12}$ alkyl; and $R_4$ and $R_5$ together with N linked thereto may form a 5- to 15-membered heterocyclic ring, a 5- to 10-membered heteroaromatic ring, a 5- to 15-membered heterocyclic ring substituted by $R_b$ and a 5- to 15-membered heteroaromatic ring substituted by $R_b$. Further, $R_4$ and $R_5$ are each independently selected from: H, $C_{1-10}$ alkyl, $COOR_8$, -Fmoc and $R_a$-substituted $C_{1-10}$ alkyl; and $R_4$ and $R_5$ together with N linked thereto may form a 5- to 15-membered heterocyclic ring, a 5- to 10-membered heteroaromatic ring, a 5- to 15-membered heterocyclic ring substituted by $R_b$ and a 5- to 15-membered heteroaromatic ring substituted by $R_b$.

Further, heterocyclyl is selected from the following structural groups:

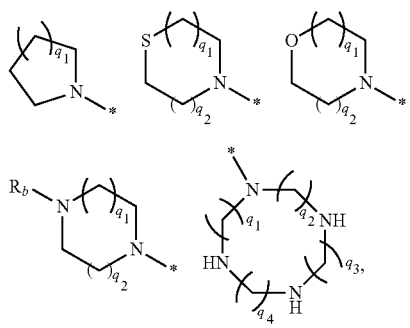

where $q_1$, $q_2$, $q_3$ and $q_4$ are each independently selected from: 1, 2, 3 or 4.

Furthermore, heterocyclyl is selected from:

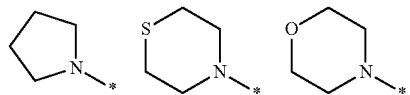

-continued

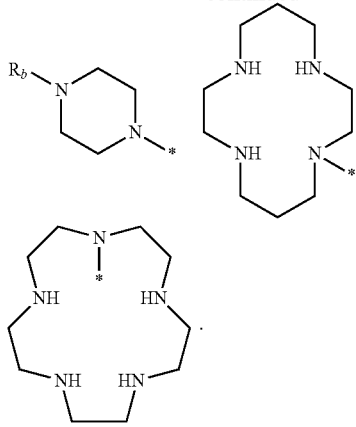

Further, $R_a$ is selected from pyridine, pyrimidine, triazine, —$NR_{a1}R_{a2}$ or —$SR_{a3}$. Furthermore, $R_a$ is selected from pyridine, —$NR_{a1}R_{a2}$ or —$SR_{a3}$.

Further, each of $R_{a1}$ and $R_{a2}$ is independently H, $C_{1-4}$ alkyl or $NR_{c1}R_{c2}$-substituted $C_{1-4}$ alkyl. Further, $R_{a3}$ is $C_{1-4}$ alkyl. Further, each of $R_{c1}$ and $R_{c2}$ is independently H or $C_{1-4}$ alkyl. Further, $R_b$ is selected from H, $C_{1-6}$ alkyl or —$(CH_2)_p NR_{b1}R_{b2}$, where p is 0, 1, 2, 3, 4, 5 or 6. Furthermore, each of $R_{b1}$ and $R_b2$ is independently H or $C_{1-4}$ alkyl.

Further, R is selected from the following groups:

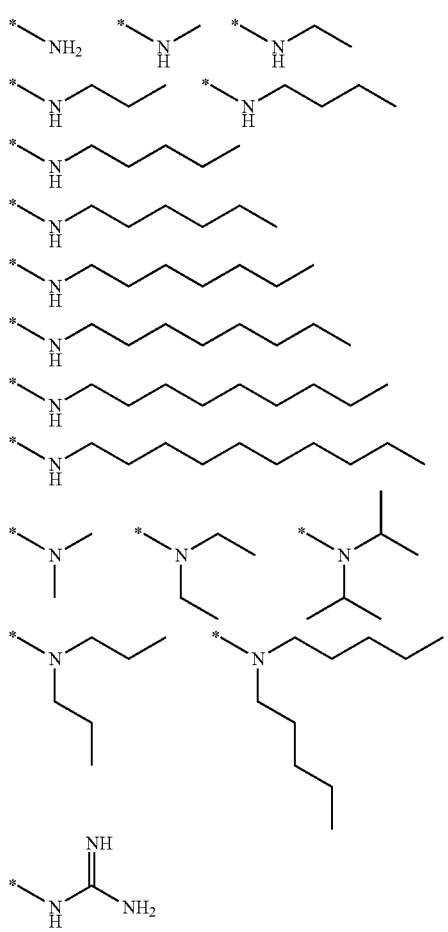

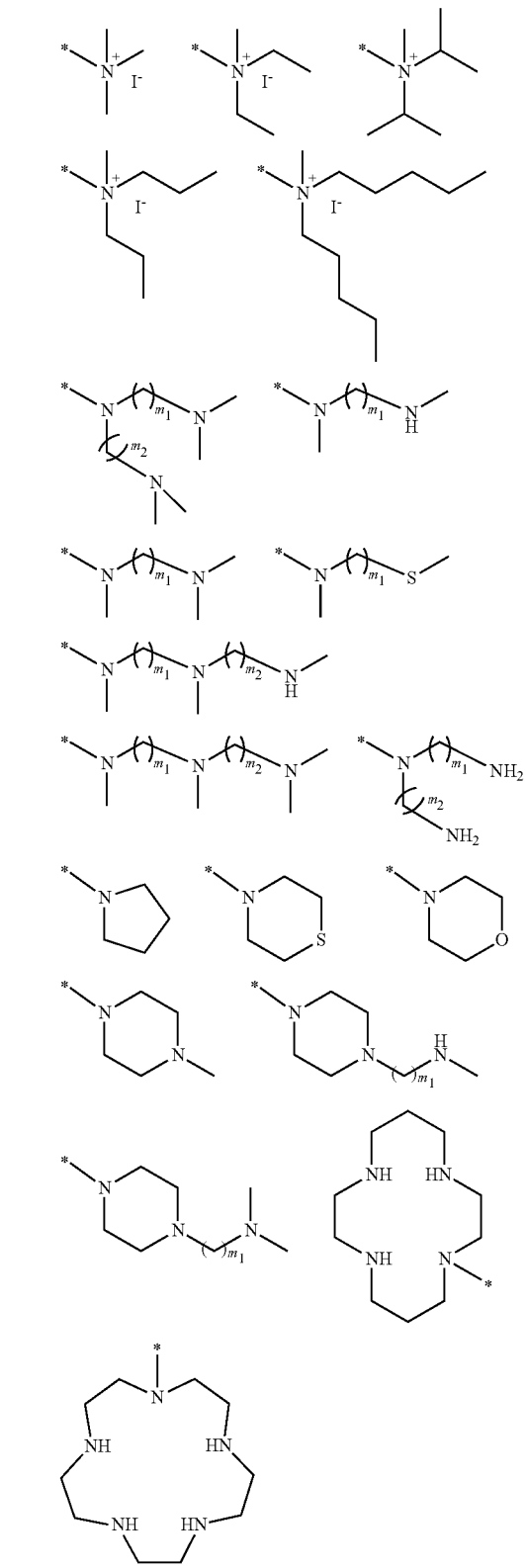

where each of $m_1$ and $m_2$ is independently 1, 2, 3, 4, 5, 6, 7 or 8.

Further, $R_1$ and $R_2$ are not simultaneously H. Further, one of $R_1$ and $R_2$ is H, and another one is

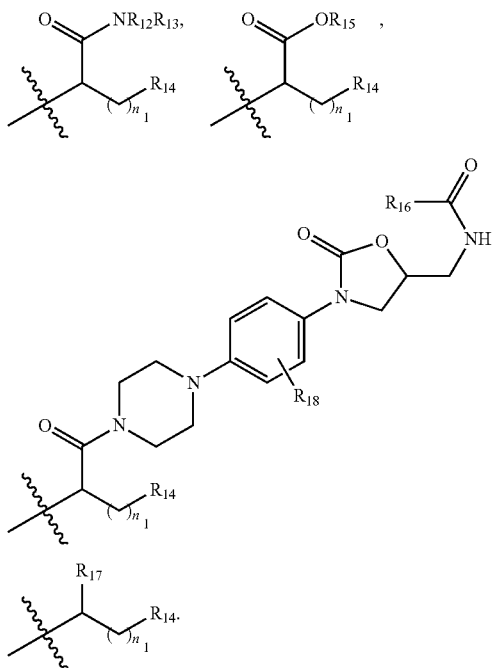

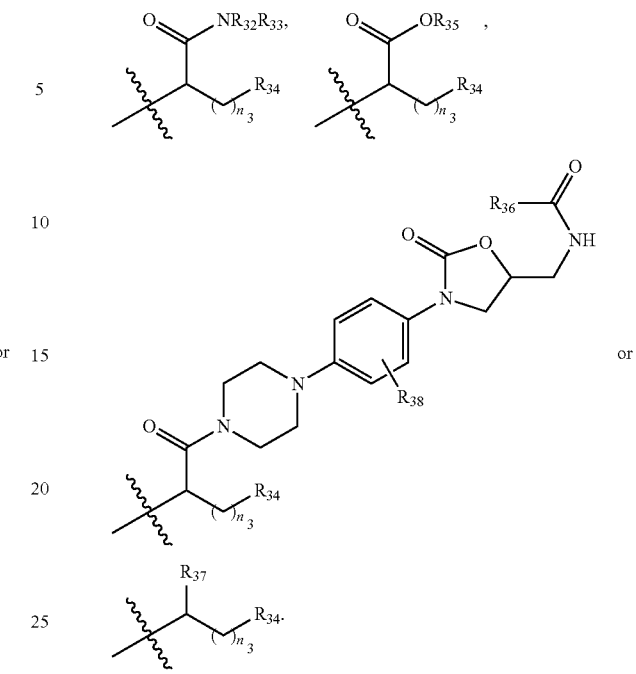

In an embodiment, $R_{12}$ and $R_{13}$ are both H. In an embodiment, one of $R_{12}$ and $R_{13}$ is H, and another one is selected from In an embodiment, $R_{32}$ and $R_{33}$ are both H. In an embodiment, one of $R_{32}$ and $R_{33}$ is H, and another one is selected from

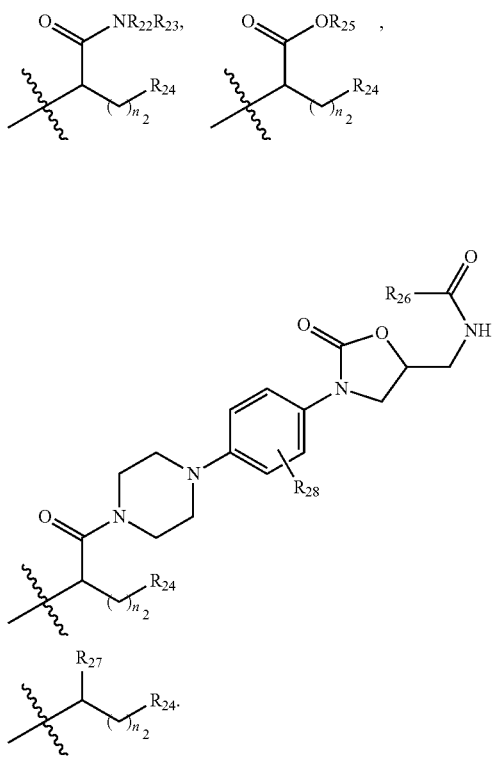

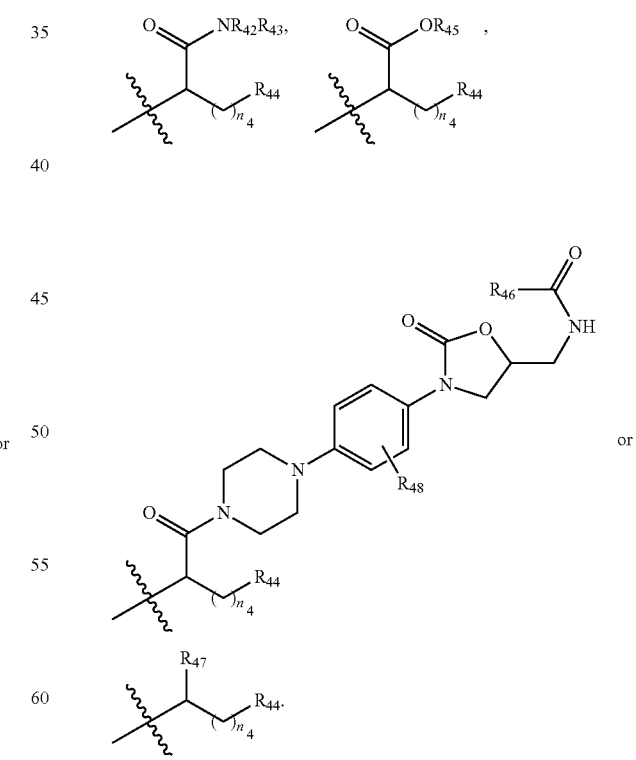

In an embodiment, $R_{22}$ and $R_{23}$ are both H. In an embodiment, one of $R_{22}$ and $R_{23}$ is H, and another one is selected from In an embodiment, $R_{42}$ and $R_{43}$ are both H. In an embodiment, one of $R_{42}$ and $R_{43}$ is H, and another one is selected from

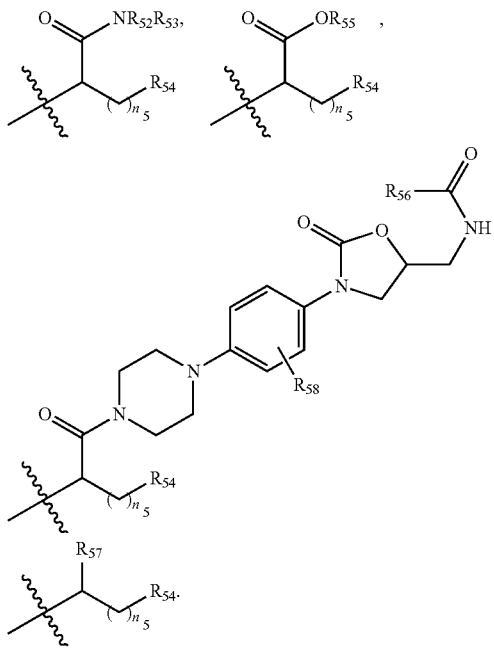

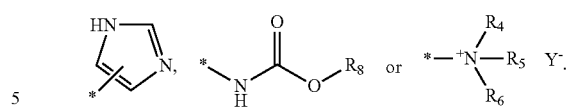

Further, $R_4$ and $R_5$ are each independently selected from H or $C_{1-4}$ alkyl. Furthermore, $R_4$ and $R_5$ are each independently selected from H, methyl, ethyl, propyl, isopropyl or butyl.

Further, the above bakuchiol derivative is selected from compounds of the following general formula:

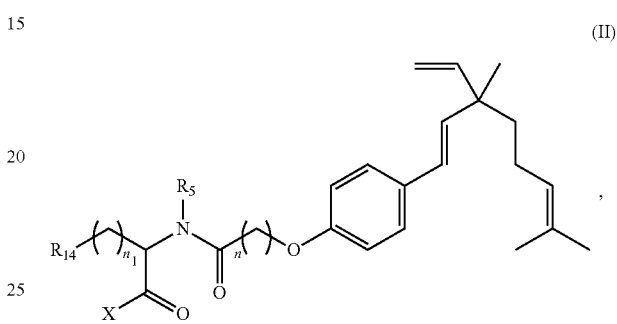

(II)

where X is $NR_{12}R_{13}$, $OR_{15}$ or

In an embodiment, $R_{52}$ and $R_{53}$ are both H. In an embodiment, one of $R_{52}$ and $R_{53}$ is H, and another one is selected from

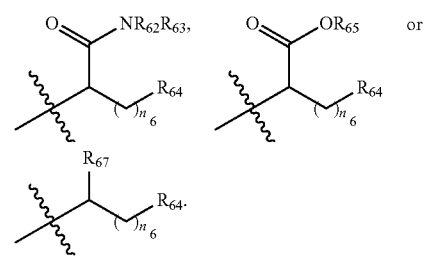

Further, $R_{14}$, $R_{24}$, $R_{34}$, $R_{44}$, $R_{54}$, $R_{64}$ and $R_{74}$ are each independently selected from: H, guanidyl, —$NR_4R_5$, —$SR_4$, 5- to 10-membered nitrogen-containing heteroaryl,

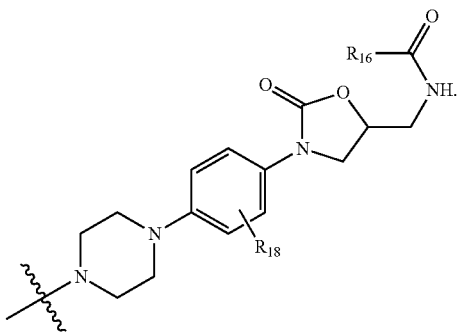

Further, the above bakuchiol derivative is selected from compounds of the following general formula:

(II')

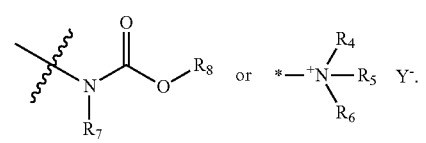

Further, $R_{14}$, $R_{24}$, $R_{34}$, $R_{44}$, $R_{54}$, $R_{64}$ and $R_{74}$ are each independently selected from H, guanidyl, —$NR_4R_5$, —$SR_4$, 5-membered nitrogen-containing heteroaryl

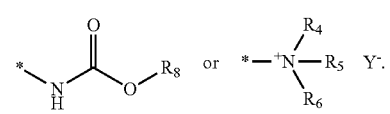

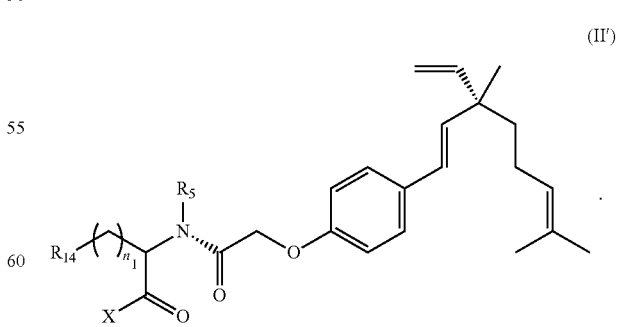

Further, $R_{14}$, $R_{24}$, $R_{34}$, $R_{44}$, $R_{54}$, $R_{64}$ and $R_{74}$ are each independently selected from H, guanidyl, —$NR_4R_5$, —$N(CH_3)_2$, —$SCH_3$, Further, in the above general formula (II) or formula (II'), X is $OR_{15}$, and $R_{14}$ is selected from: H, guanidyl, —$NH_2$, —$SCH_3$,

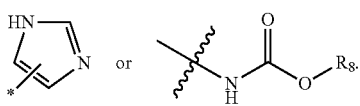

Further, in the above general formula (II) or formula (II'), X is $NR_{12}R_{13}$, and at least one of $R_{14}$, $R_{24}$, $R_{34}$, $R_{44}$, $R_{54}$, $R_{64}$ and $R_{74}$ is guanidyl.

Further, in the above general formula (II) or formula (II'), X is $NR_{12}R_{13}$; one of $R_{12}$ and $R_{13}$ is H, and another one is selected from

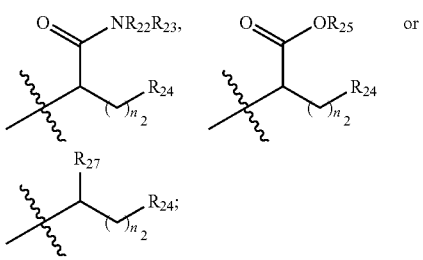

one of $R_{22}$ and $R_{23}$ is H, and another one is selected from

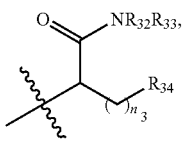

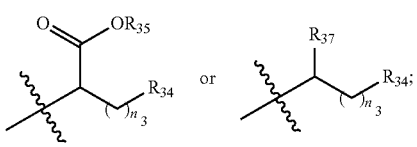

one of $R_{32}$ and $R_{33}$ is H, and another one is selected from

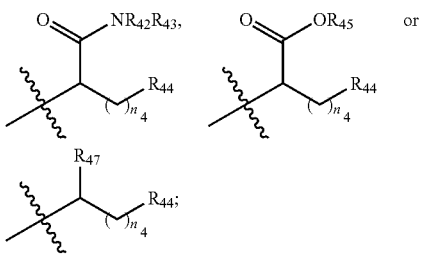

one of $R_{42}$ and $R_{43}$ is H, and another one is selected from

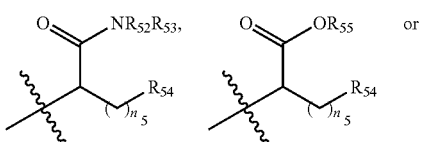

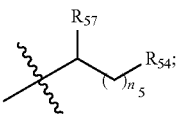

and one of $R_{62}$ and $R_{63}$ is H, and another one is selected from

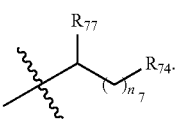

In an embodiment, in the above general formula (II) or formula (II'), X is

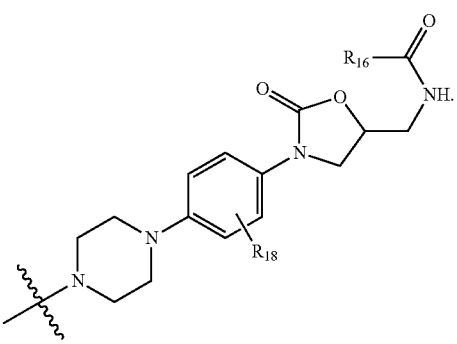

In an embodiment, in the above general formula (II) or formula (II'), X is $NR_{12}R_{13}$; and one of $R_{12}$ and $R_{13}$ is H, and another one is selected from

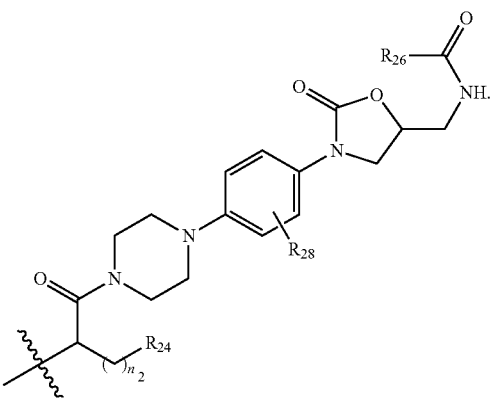

In an embodiment, in the above general formula (II) or formula (II'), X is $NR_{12}R_{13}$; one of $R_{12}$ and $R_{13}$ is H, and another one is selected from

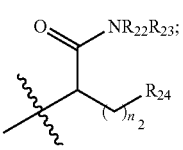

and one of $R_{22}$ and $R_{23}$ is H, and another one is selected from

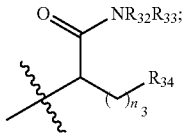

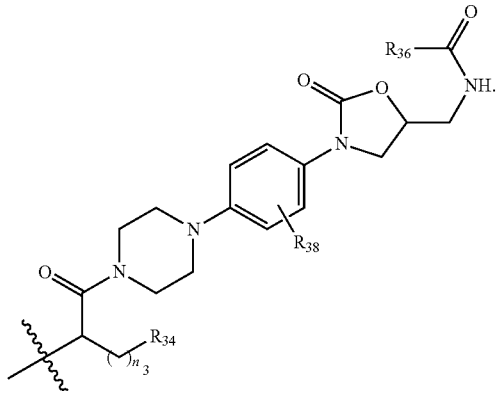

In an embodiment, in the above general formula (II) or formula (II') X is $NR_{12}R_{13}$; one of $R_{12}$ and $R_{13}$ is H, and another one is selected from

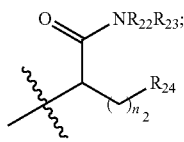

one of $R_{22}$ and $R_{23}$ is H, and another one is selected from and one of $R_{32}$ and $R_{23}$ is H, and another one is selected from

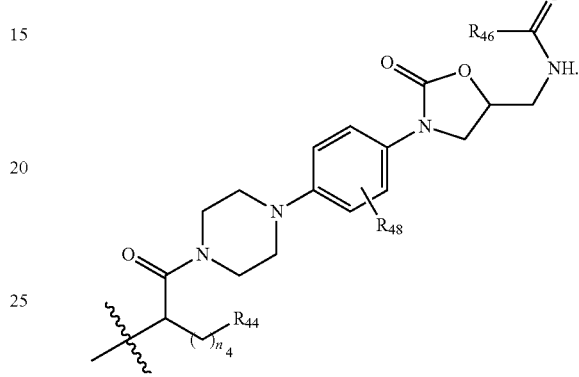

Further, the above bakuchiol derivative is selected from compounds of the following general formulae:

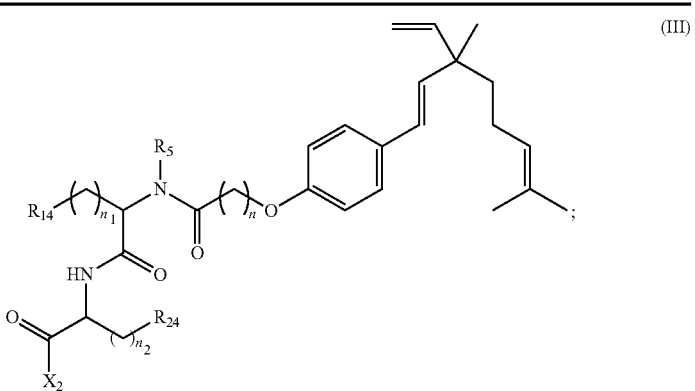

(III)

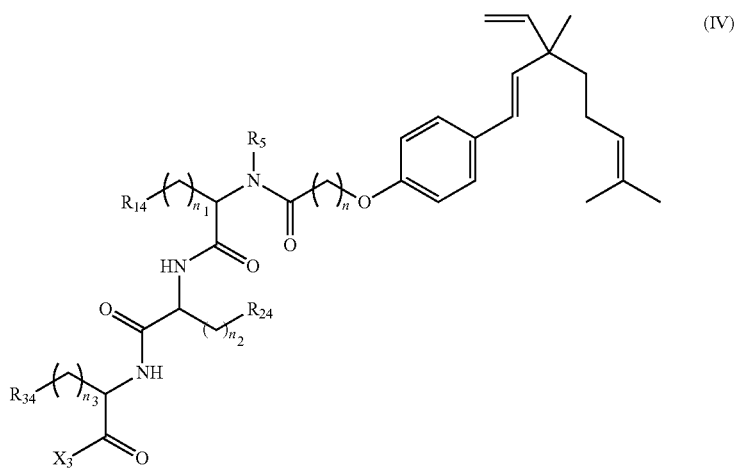

(IV)

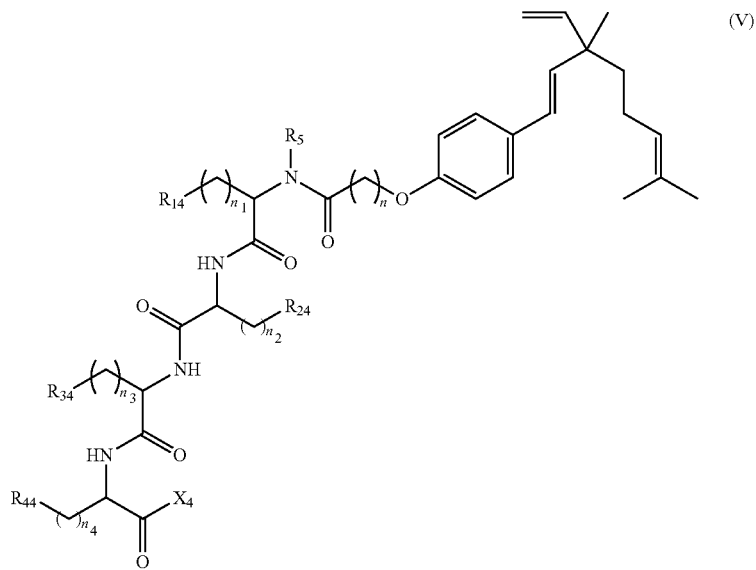
(V)
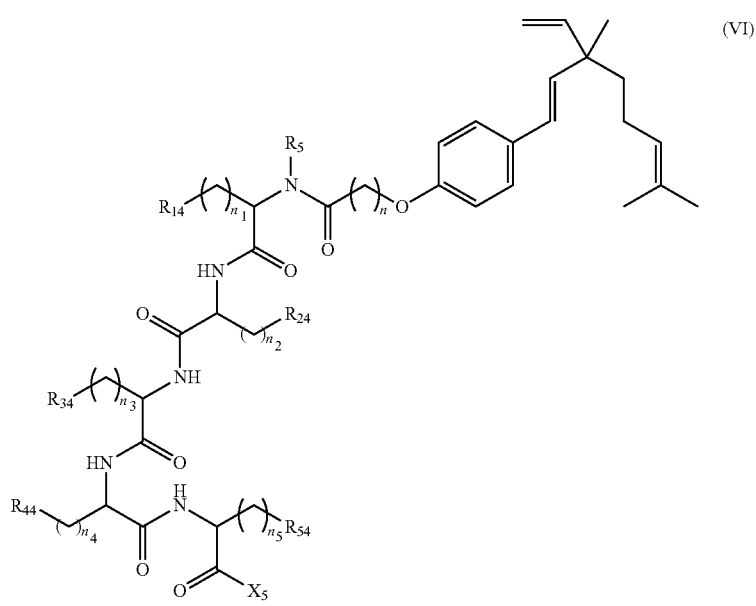
(VI)

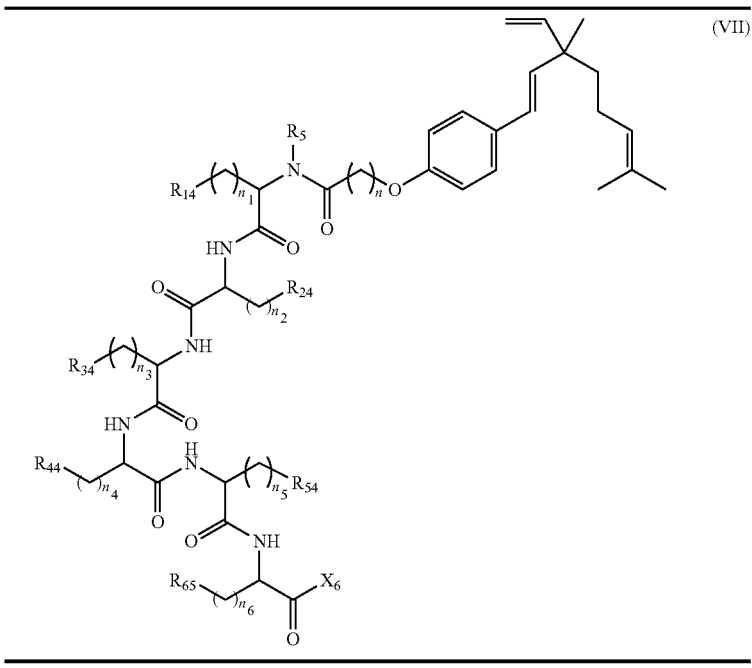
wherein X₂ is $NR_{22}R_{23}$, $OR_{25}$ or
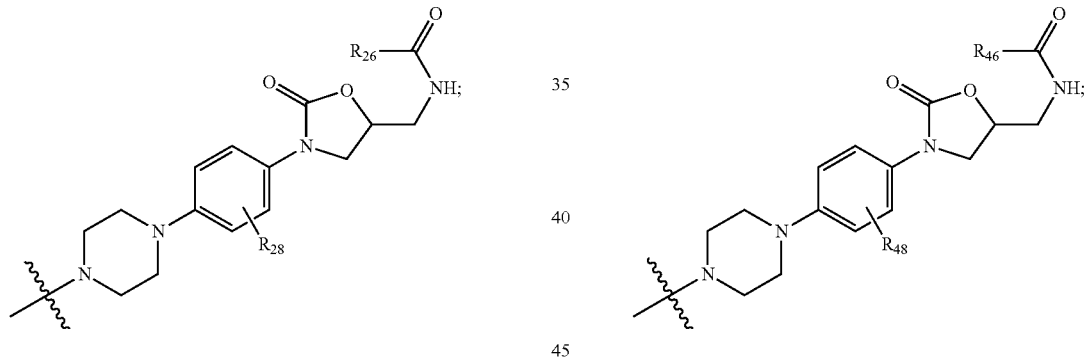
X₃ is $NR_{32}R_{33}$, $OR_{35}$ or
X₄ is $NR_{42}R_{43}$, $OR_{45}$ or
X₅ is $NR_{52}R_{53}$, $OR_{55}$ or
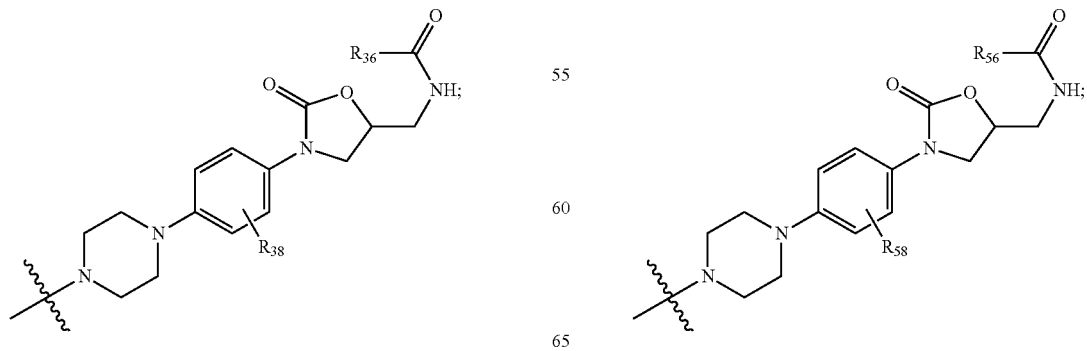

$X_6$ is $NR_{62}R_{63}$, $OR_{65}$ or
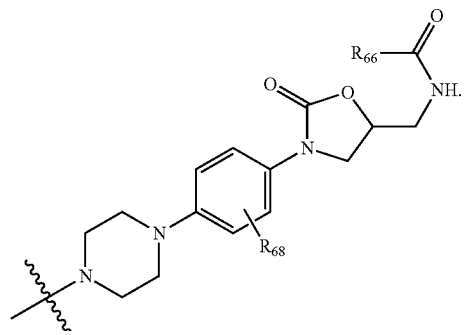
Further, the above bakuchiol derivative is selected from compounds of the following general formulae:
(III')
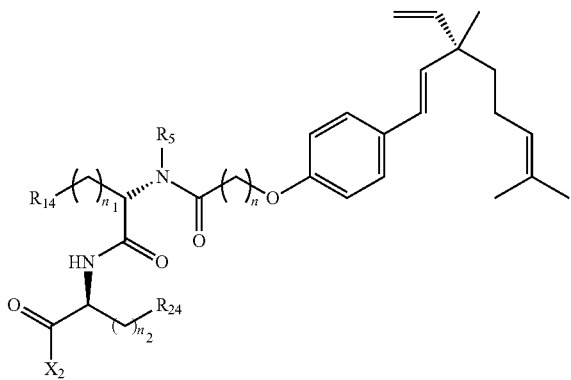
(IV')
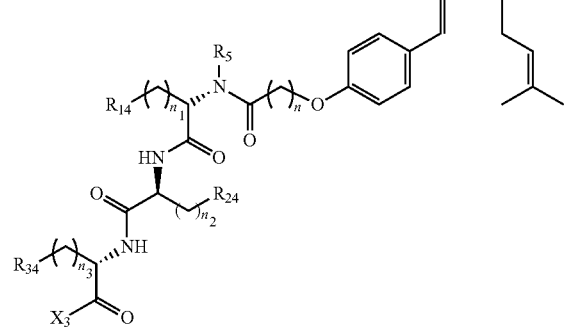
(V')
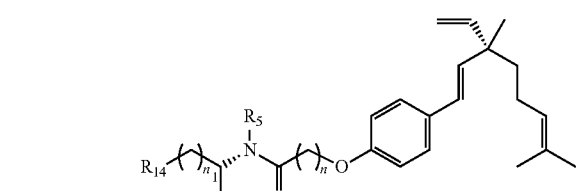
(VI')
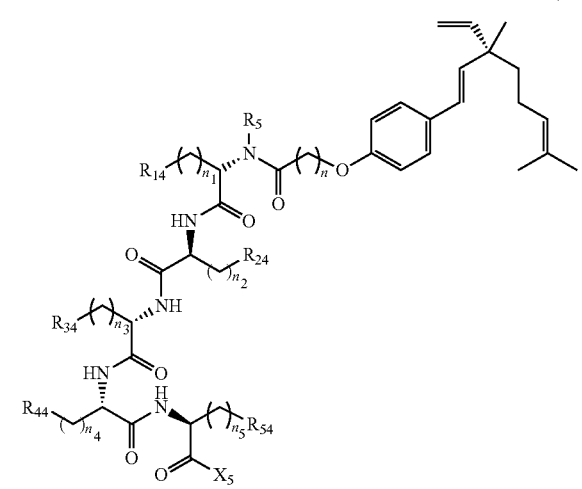
(VII')
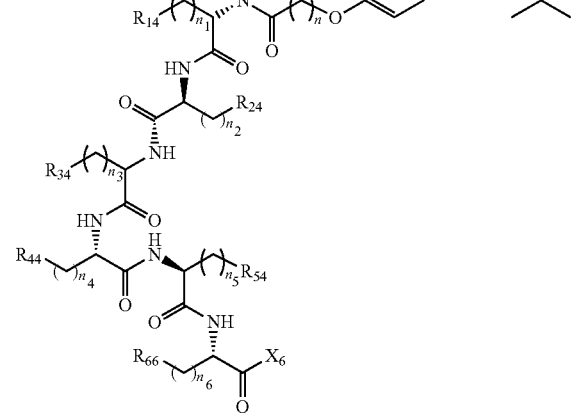
Further, the above bakuchiol derivative is selected from the following compounds:

Compound 1
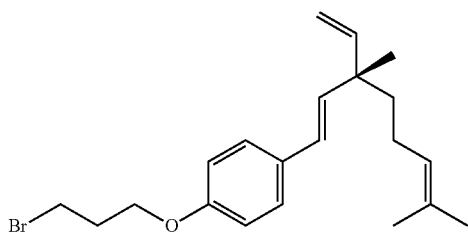
Compound 2
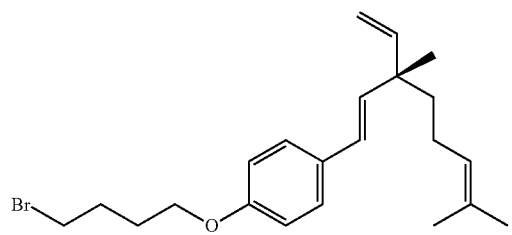
Compound 3
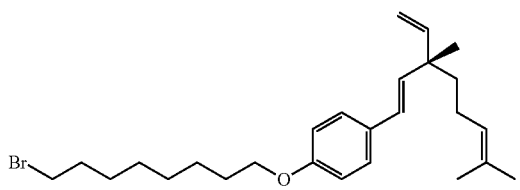
Compound 4
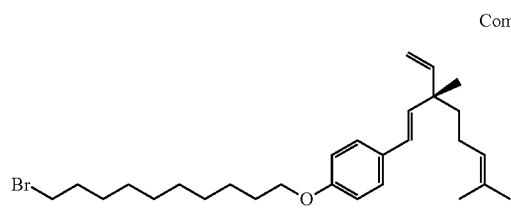
Compound 5
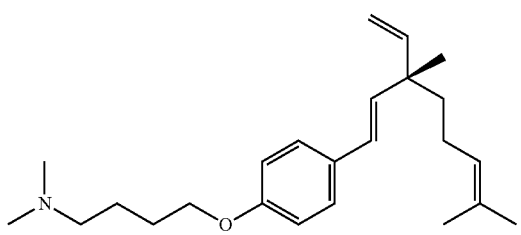
Compound 6
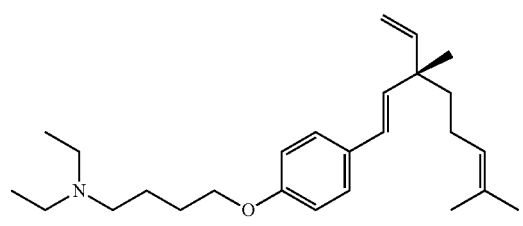
Compound 7
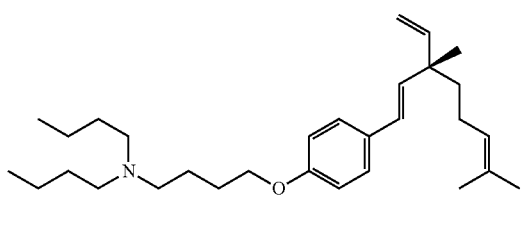
Compound 8
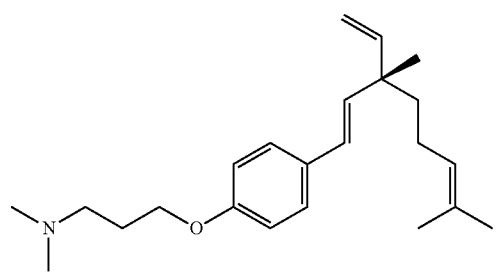
Compound 9
Compound 10
Compound 11
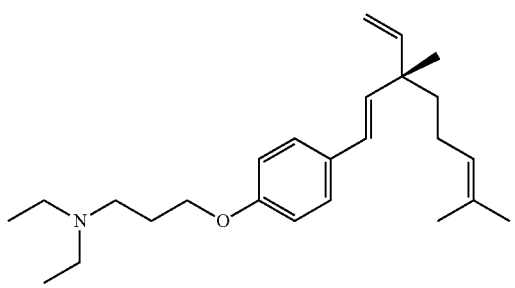

-continued
Compound 12
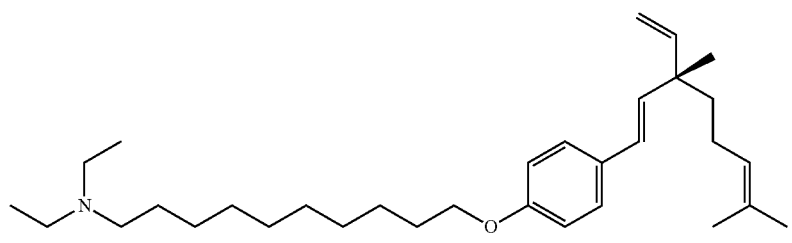
Compound 13
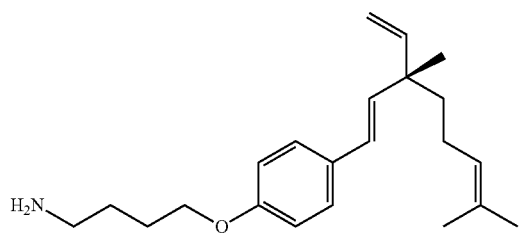
Compound 14
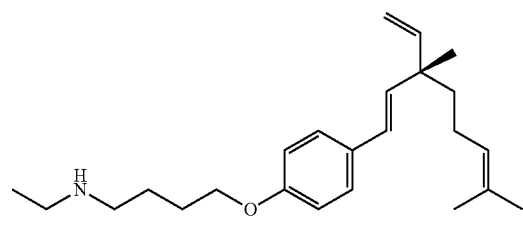
Compound 15
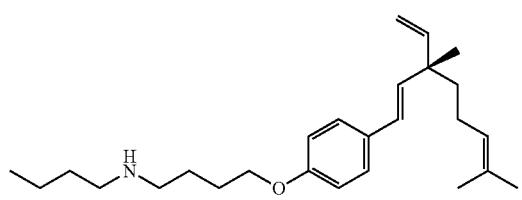
Compound 16
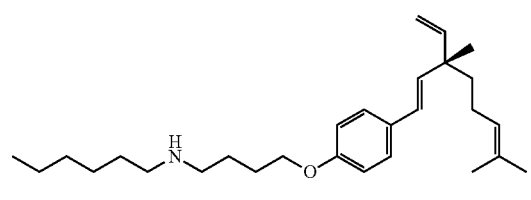
Compound 17
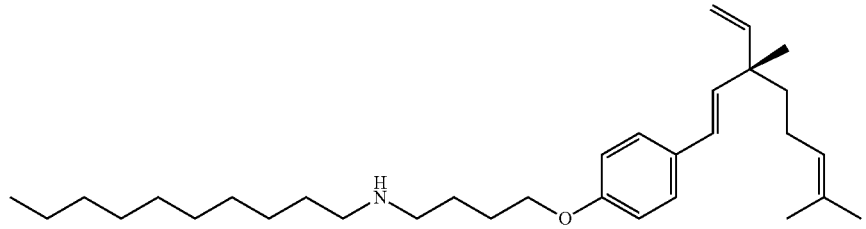
Compound 18
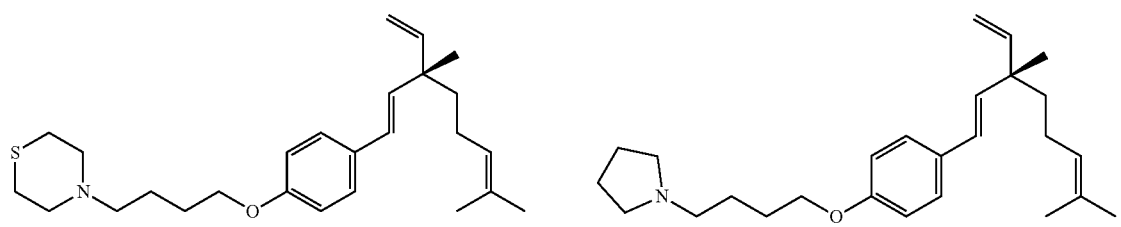
Compound 19
Compound 20

-continued
Compound 21
Compound 22
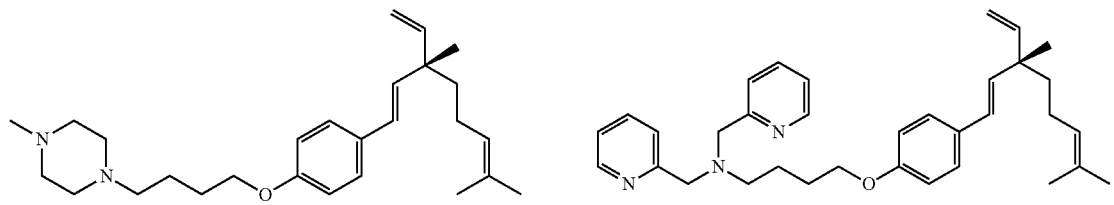
Compound 23
Compound 24
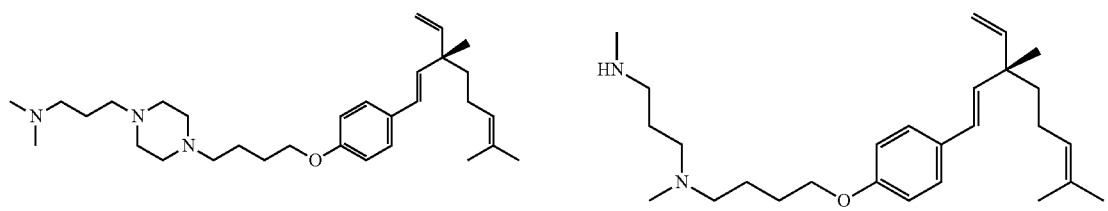
Compound 25
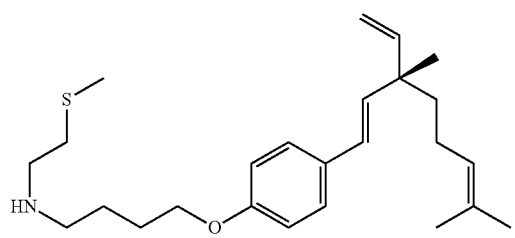
Compound 26
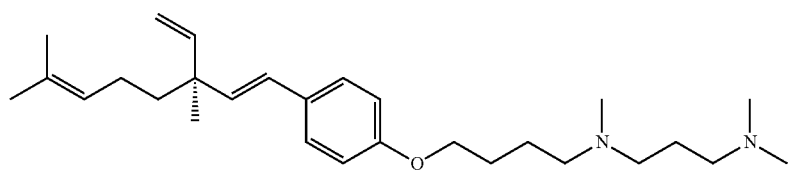
Compound 27
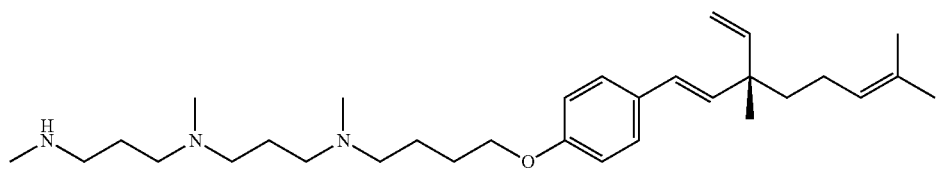
Compound 28
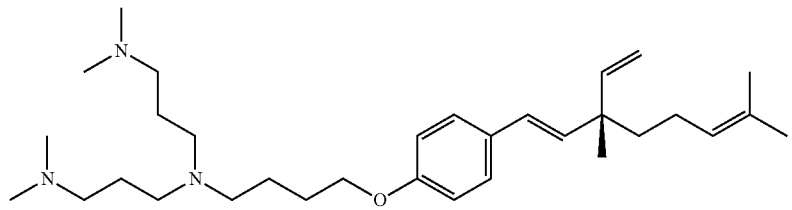
Compound 29
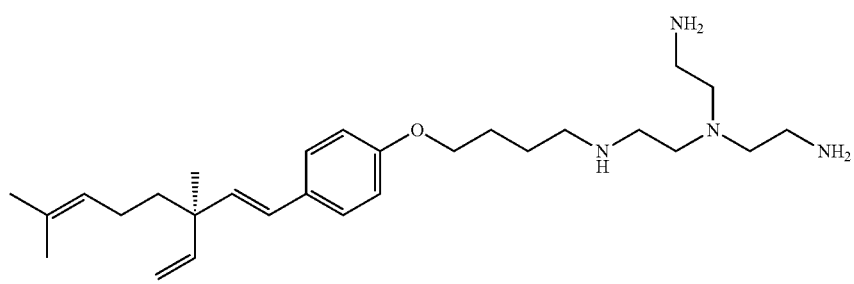

-continued
Compound 30
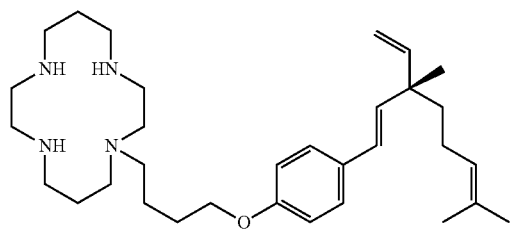
Compound 31
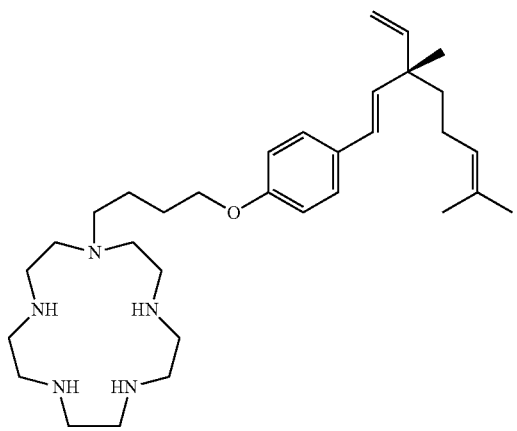
Compound 32
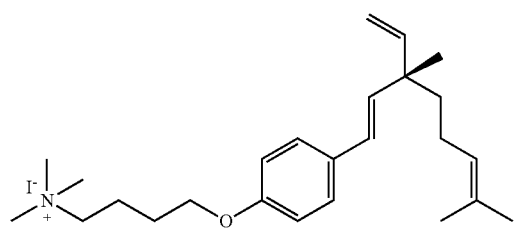
Compound 33
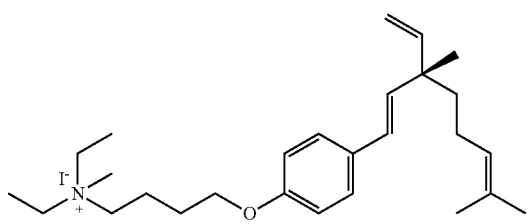
Compound 34
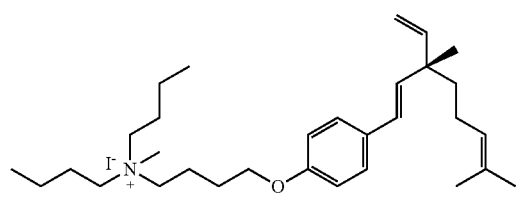
Compound 35
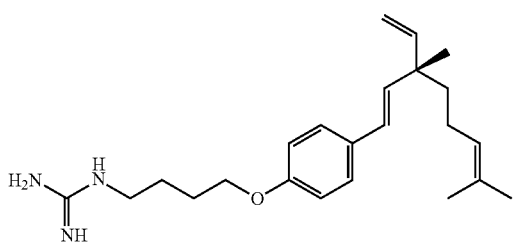
Compound 36
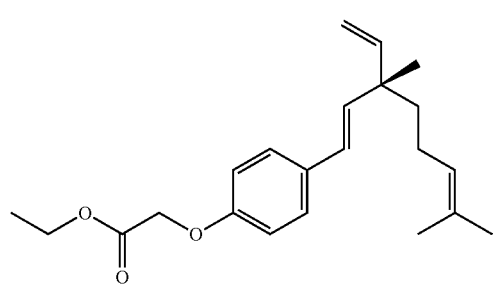
Compound 38
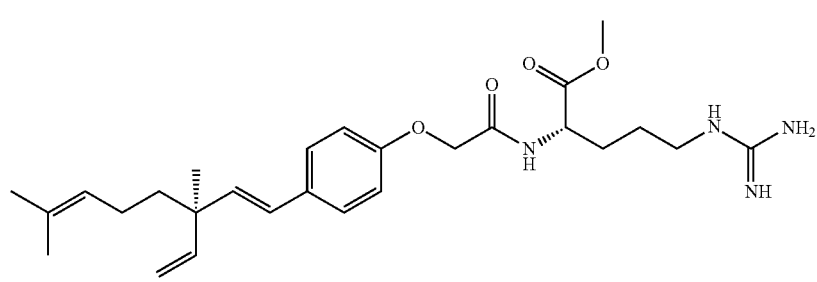

-continued
Compound 39
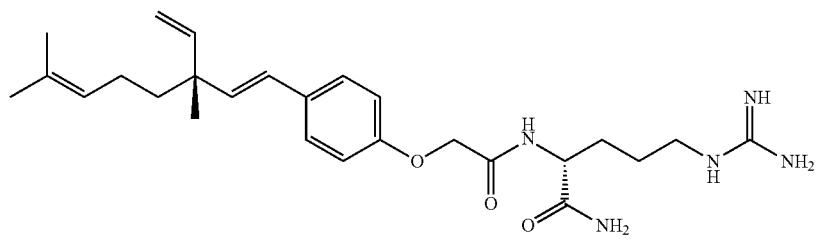
Compound 40
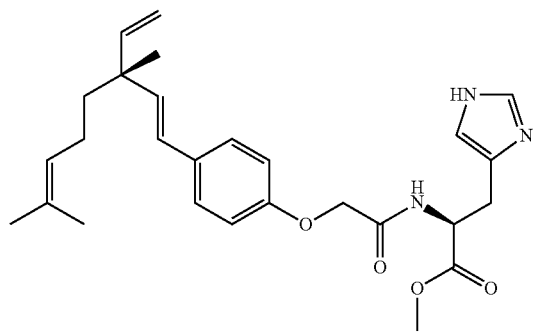
Compound 41
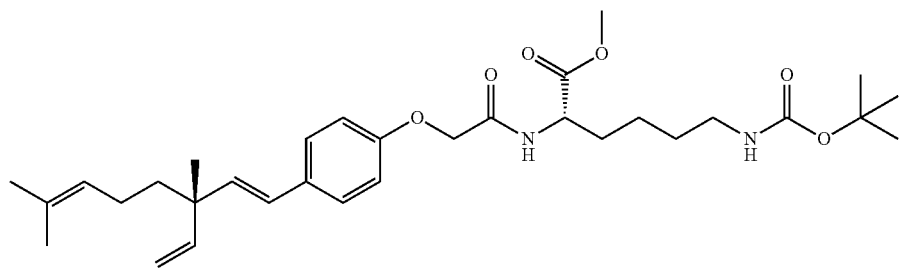
Compound 42
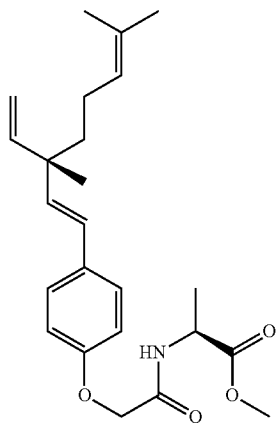
Compound 43
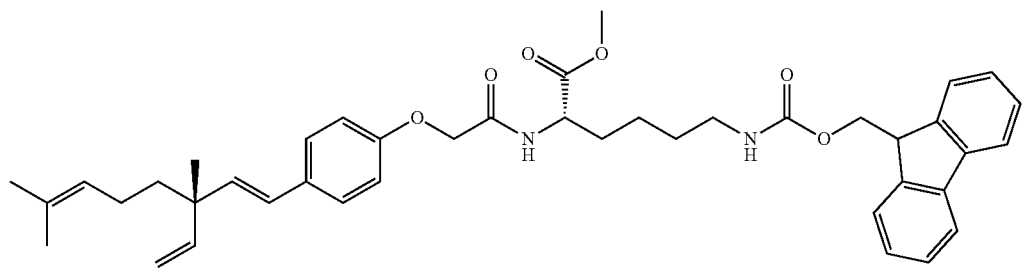

Compound 44
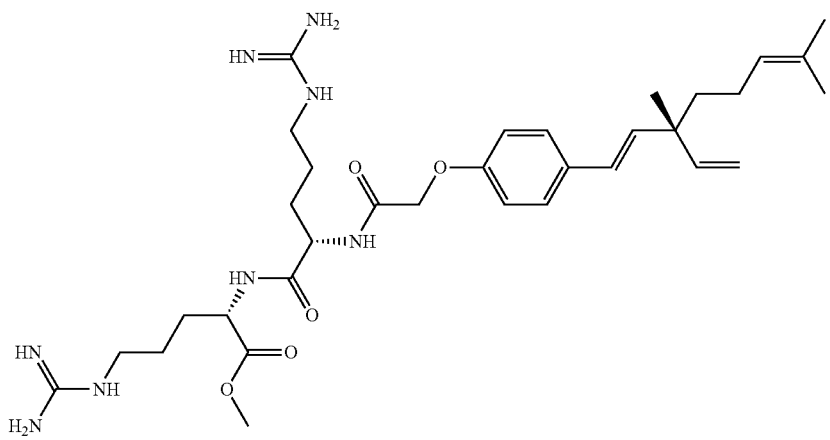
Compound 45
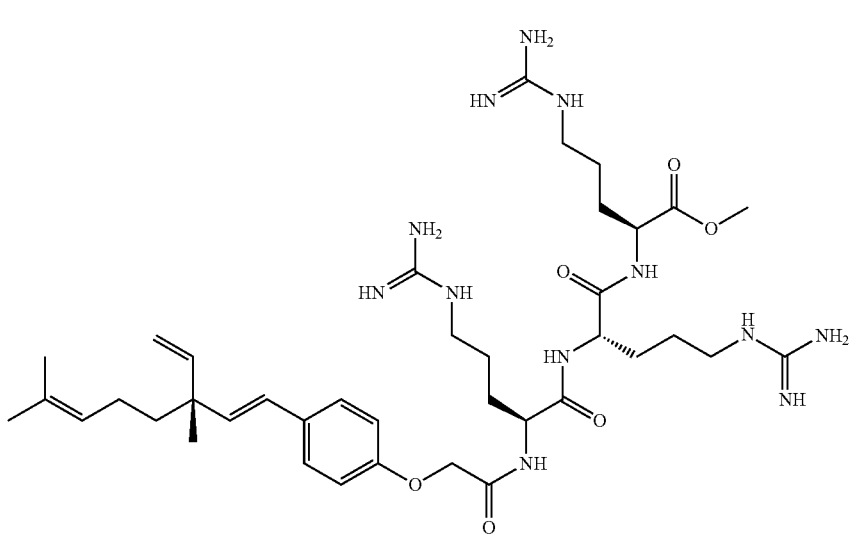
Compound 46
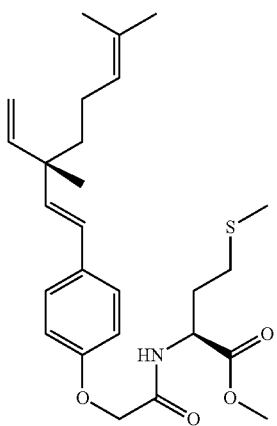
Compound 47
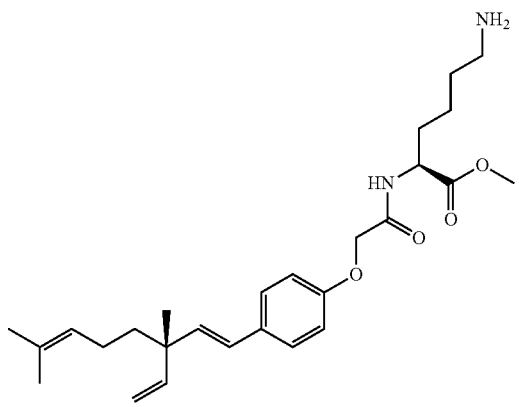

Compound 49
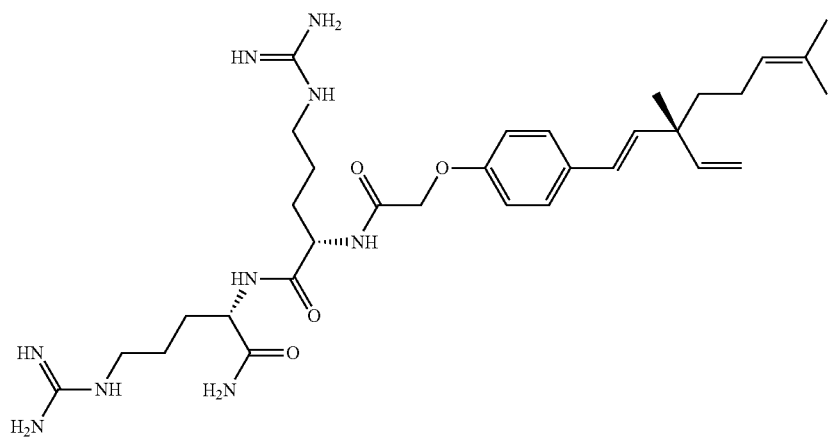
Compound 50
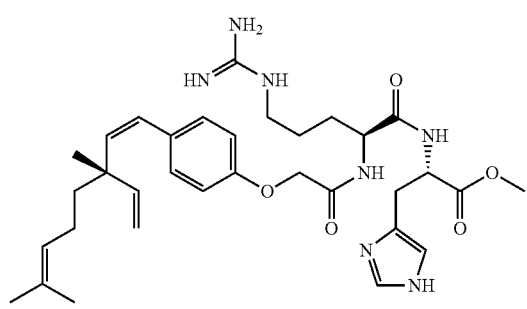
Compound 51
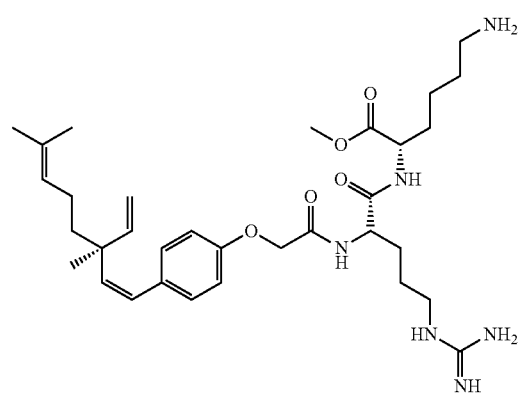
Compound 52
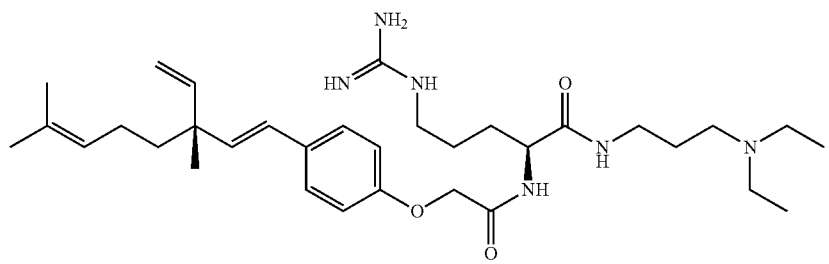
Compound 53
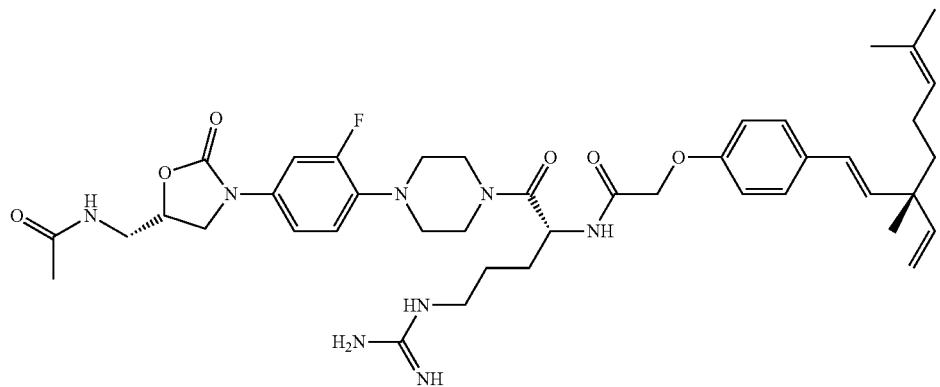

-continued
Compound 55
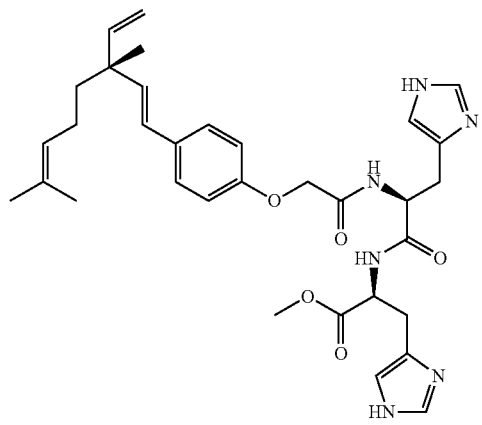
Compound 56
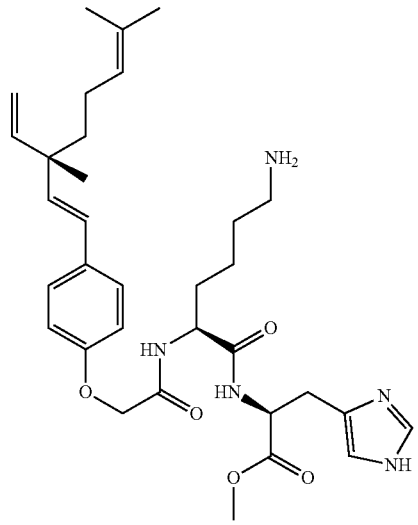
Compound 58
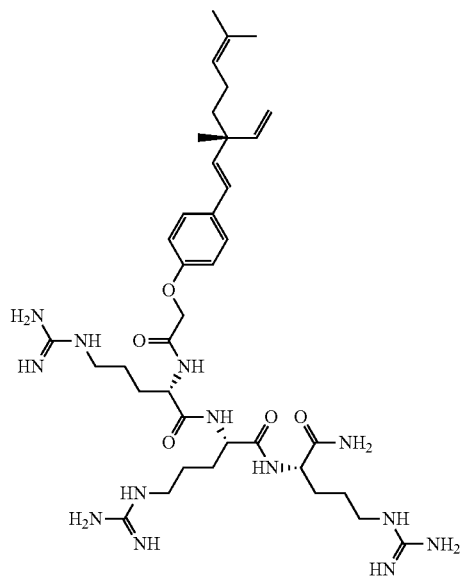
Compound 59
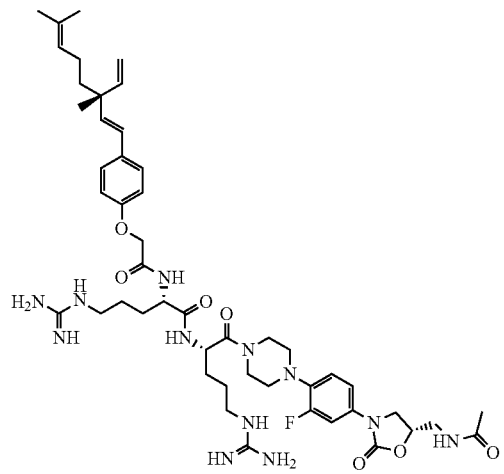

-continued
Compound 60
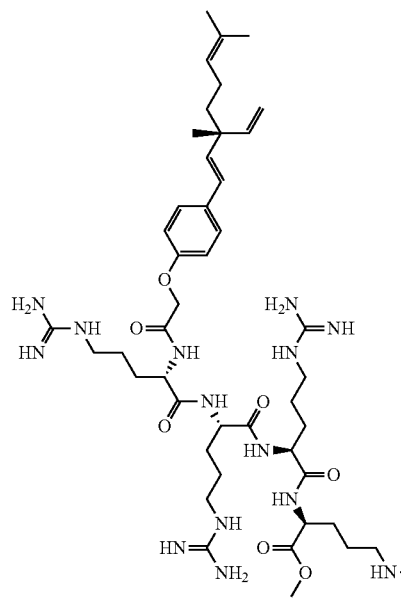
Compound 61
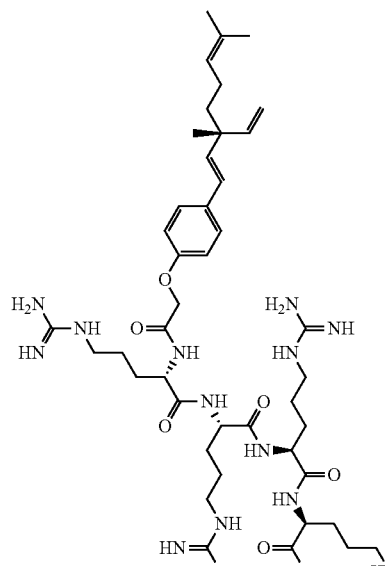
Compound 63
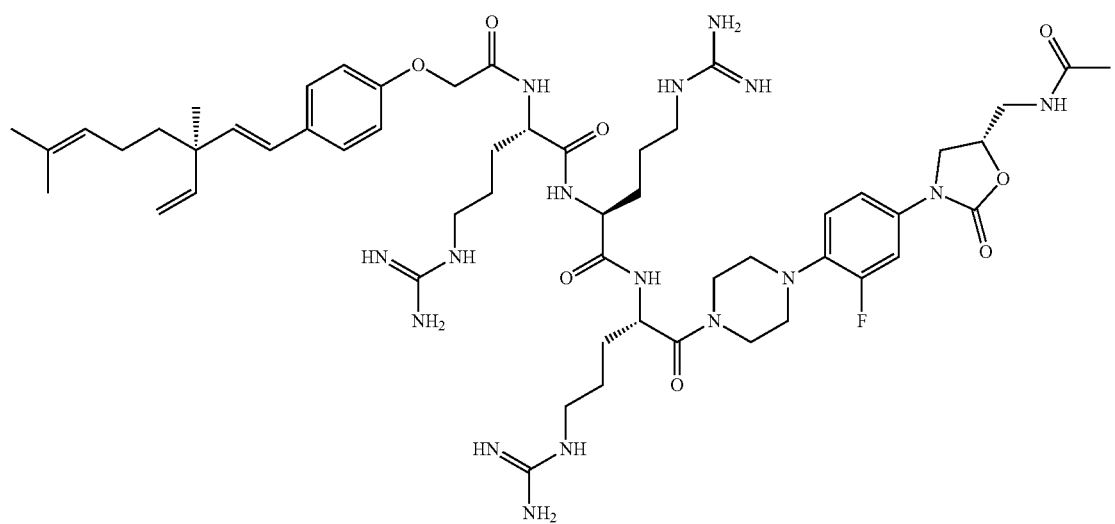
Compound 64
Compound 65
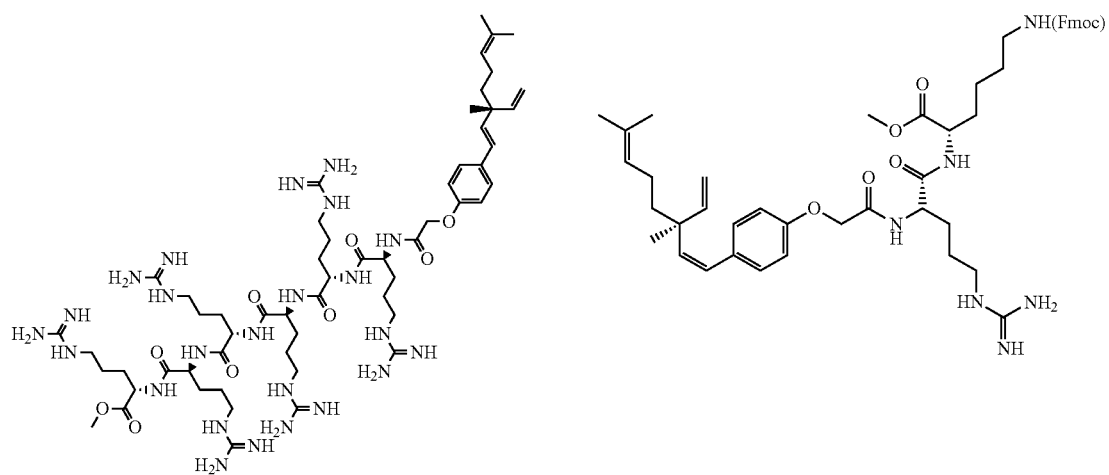

Compound 66
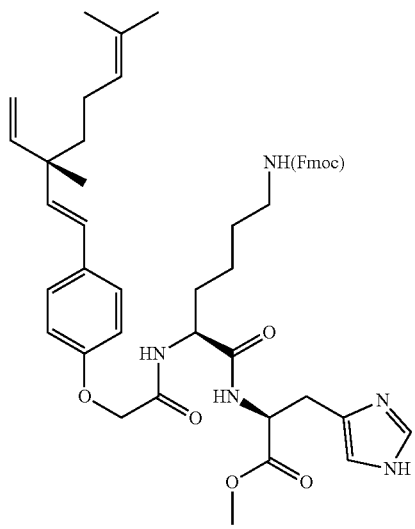
Compound 37
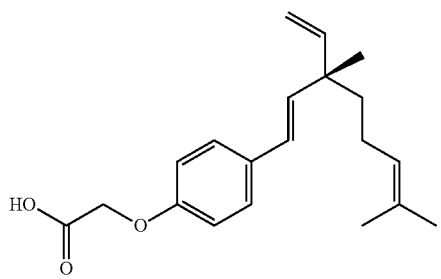
Compound 48
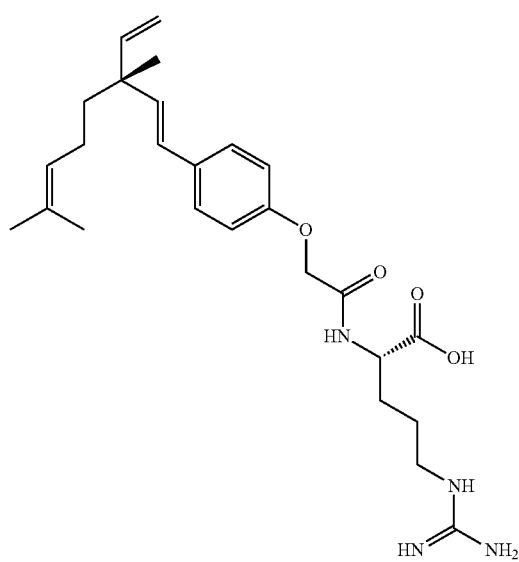
Compound 54
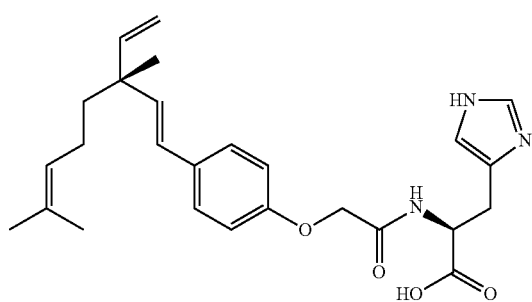

Compound 57

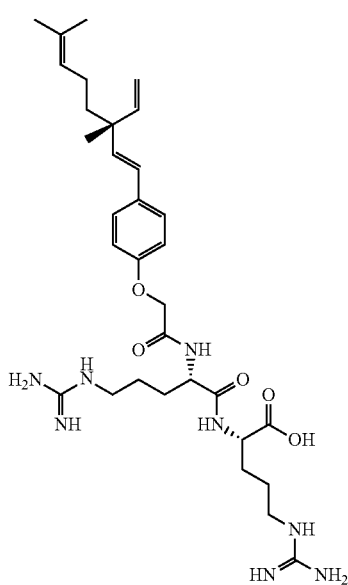

Compound 62

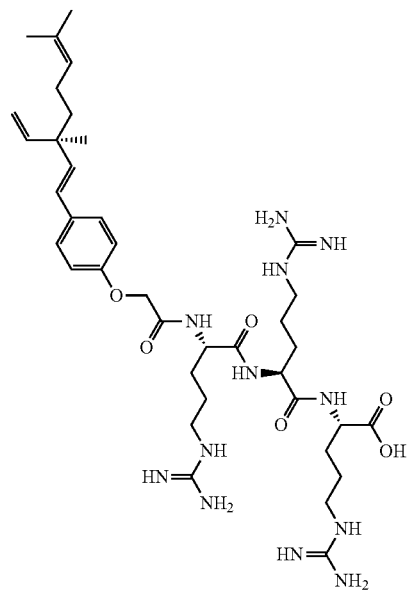

An embodiment of the disclosure also provides a preparation method of the above bakuchiol derivative.

(1) When R is a halogen, the preparation method includes the following step:

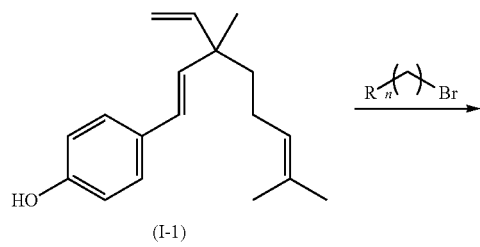

S101: a compound shown in formula (I-1) is reacted with

to obtain a compound shown in formula (I-1) with R being a halogen;

(2) when R is $NR_4R_5$,

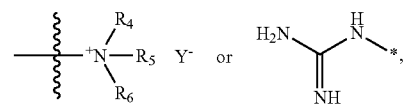

the preparation method includes the following steps:

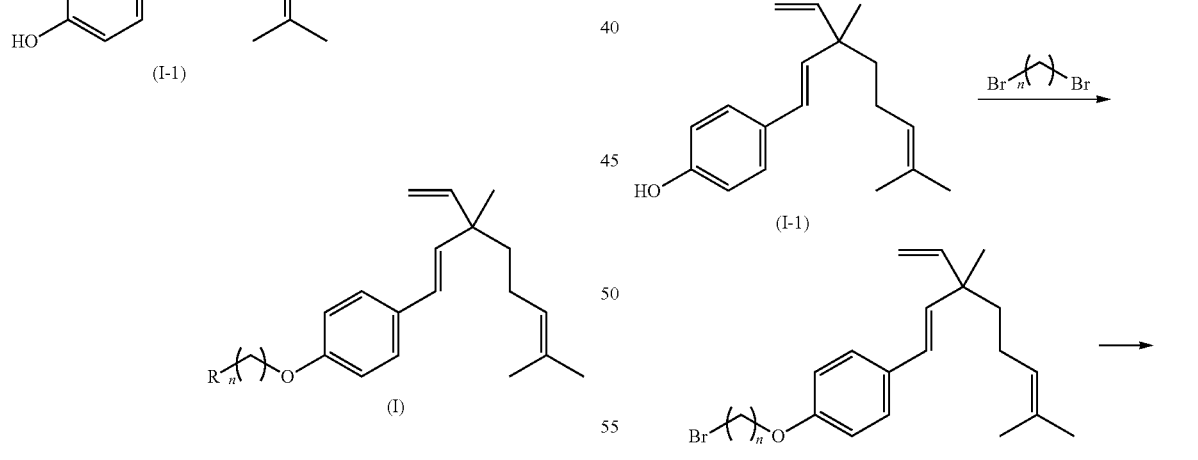

S201: a compound shown in formula (I-1) is reacted with

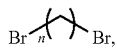

to obtain a compound shown in formula (I) with R being Br;

S202: the compound shown in formula (I) with R being Br is reacted with $HNR_4R_5$, to obtain a compound shown in formula (I) with R being $NR_4R_5$;

S203: the compound shown in formula (I) with R being $NR_4R_5$ is reacted with haloalkyl, to obtain a compound shown in formula (I) with R being

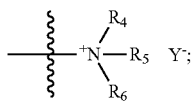

and

S204: a compound shown in formula (I) with R being $NH_2$ is reacted with

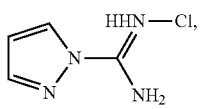

to obtain a compound shown in formula (I) with R being

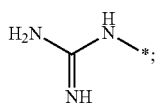

and (3) when R is selected from $CONR_1R_2$ and $—COOR_3$, the preparation method includes the following steps:

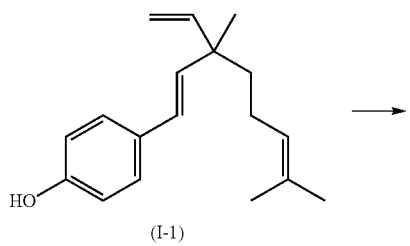
(I-1)

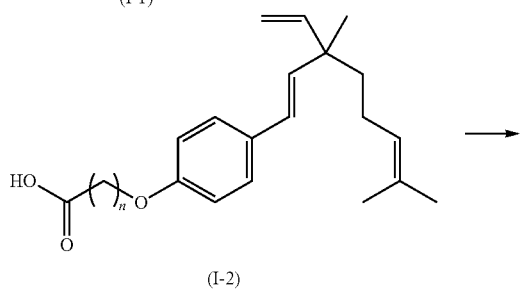
(I-2)

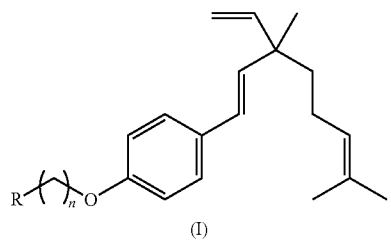
(I)

S301: a condensation reaction is performed on a compound shown in formula (I-1) and alkyl ester of bromoalkyl acid, to obtain a compound shown in formula (I) with R being $—COOR_3$;

further, alkyl ester of bromoalkyl acid is $C_{1-6}$ alkyl bromoacetate;

S302: a condensation reaction is performed on the compound shown in formula (I-2) and

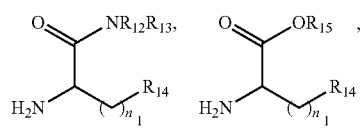

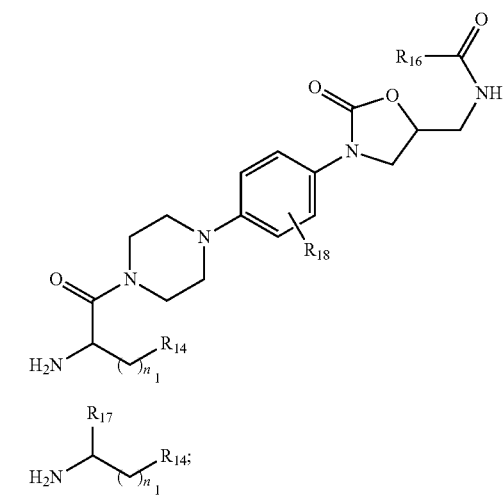

to obtain a compound shown in formula (II);

S303: a hydrolysis reaction is performed on a compound shown in formula (II-1), to obtain a compound shown in formula (II-2);

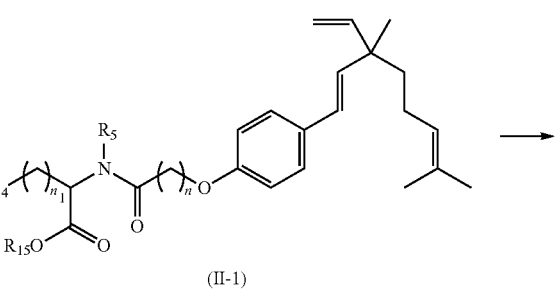
(II-1)

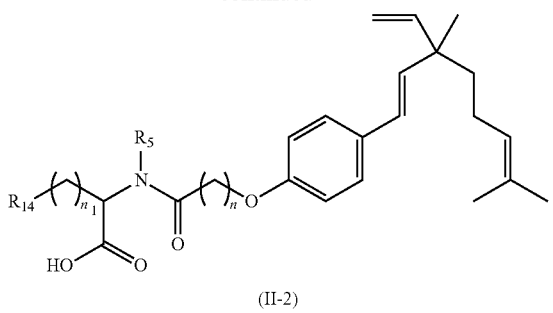

(II-2)

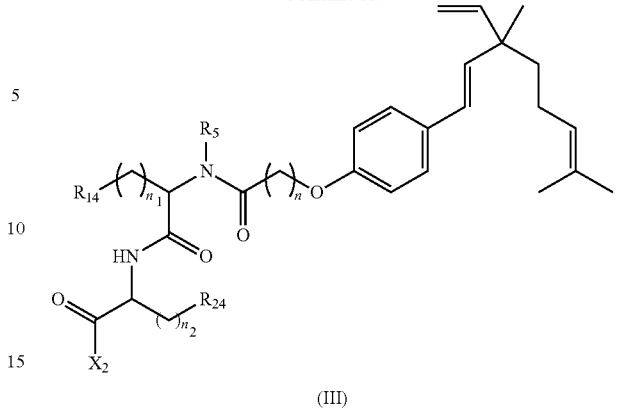

(III)

S304: a condensation reaction is performed on the compound shown in formula (II-2) and

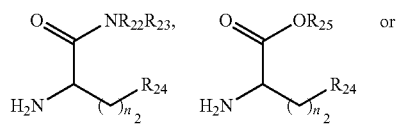

to obtain a compound shown in formula (III); and

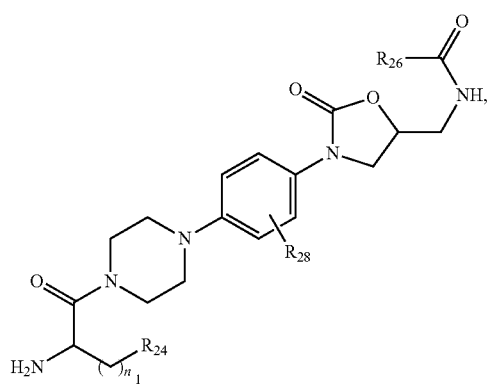

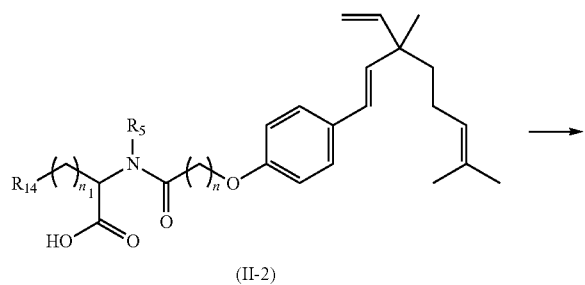

(II-2)

S305: optionally, according to this cycle, a compound containing an ester group is hydrolyzed, and a condensation reaction with corresponding amine is then performed to obtain compounds shown in formula (IV), (V), (VI) or (VII). The structure and definition of each general formula are as mentioned above, and will not be repeated here.

It could be understood that a step of ester hydrolysis is the same as S303, and a step of condensation reaction is the same as S304. The difference lies in that reaction substrates are different. For example, a compound shown in formula (III) with $X_2$ being $OR_{35}$ is used as the substrate to perform a hydrolysis reaction to obtain carboxylic acid, and the carboxylic acid based compound is then used as the substrate to perform a condensation reaction with a corresponding substance. The conditions of the hydrolysis and condensation reactions are not particularly limited, and the existing hydrolysis and condensation reaction conditions may be adopted. These should be understood to be within the protection scope of the disclosure.

An embodiment of the disclosure also provides a pharmaceutical composition including the above bakuchiol derivative and a pharmaceutically acceptable salt thereof, and a pharmaceutically acceptable excipient.

An embodiment of the disclosure provides use of the above bakuchiol derivative and a pharmaceutically acceptable salt thereof or the above pharmaceutical composition in preparation of antibacterial agents.

An embodiment of the disclosure provides use of the above bakuchiol derivative and a pharmaceutically acceptable salt thereof or the above pharmaceutical composition in preparation of drugs for treating and preventing diseases caused by bacterial infection.

An embodiment of the disclosure provides a method for treating or preventing bacterial infection, including administration of an effective amount of the above bakuchiol derivative and a pharmaceutically acceptable salt thereof or the above pharmaceutical composition.

Specific Examples are Given Below to Illustrate the Disclosure

Preparation of Compound 1

Bakuchiol (162 mg, 0.632 mmol) was dissolved in acetone (10 mL). Then, potassium carbonate (436.6 mg, 3.16 mmol) and 1,3-dibromopropane (480.8 µL, 4.74 mmol) were added. The mixture was stirred under reflux for 6 hours. After the reaction, the reaction mixture was diluted with ethyl acetate and extracted twice with water. The organic phase was concentrated under reduced pressure. The crude product was purified by silica gel column chromatography (petroleum ether/ethyl acetate, 8:1, v/v), to afford compound 1 as a colorless clear oil (190.2 mg, 80%). $^1$H NMR (400 MHz, CDCl$_3$) δ 7.29 (d, J=8.7 Hz, 2H), 6.84 (d, J=8.7 Hz, 2H), 6.27 (d, J=16.3 Hz, 1H), 6.07 (d, J=16.2 Hz, 1H), 5.89 (dd, J=17.4, 10.8 Hz, 1H), 5.15-5.08 (m, 1H), 5.06-4.99 (m, 2H), 4.10 (t, J=5.8 Hz, 2H), 3.60 (t, J=6.5 Hz, 2H), 2.36-2.25 (m, 2H), 2.00-1.91 (m, 2H), 1.68 (s, 3H), 1.59 (s, 3H), 1.52-1.47 (m, 2H), 1.20 (s, 3H). $^{13}$C NMR (100 MHz, CDCl$_3$) δ 157.91, 146.05, 136.06, 131.38, 131.07, 127.27 (2×CH), 126.57, 124.89, 114.64 (2×CH), 111.96, 65.45, 42.62, 41.38, 32.48, 30.11, 25.79, 23.44, 23.32, 17.73. HRMS (ESI+): calculated for $C_{21}H_{29}BrO$ [M+H]$^+$ 377.1480, found 377.1475.

Preparation of Compound 2

According to the method for synthesis of compound 1, bakuchiol (162 mg, 0.632 mmol), potassium carbonate (436.6 mg, 3.16 mmol) and 1,4-dibromobutane (565.3 μL, 4.74 mmol) used as starting materials were prepared into compound 2 as a yellow oil (207.6 mg, 84%). $^1$H NMR (400 MHz, CDCl$_3$) δ 7.28 (d, J=8.7 Hz, 2H), 6.82 (d, J=8.7 Hz, 2H), 6.26 (d, J=16.3 Hz, 1H), 6.06 (d, J=16.2 Hz, 1H), 5.88 (dd, J=17.4, 10.8 Hz, 1H), 5.15-5.08 (m, 1H), 5.06-4.98 (m, 2H), 3.99 (t, J=6.1 Hz, 2H), 3.49 (t, J=6.6 Hz, 2H), 2.11-2.03 (m, 2H), 1.99-1.91 (m, 4H), 1.68 (s, 3H), 1.58 (s, 3H), 1.52-1.47 (m, 2H), 1.20 (s, 3H). $^{13}$C NMR (100 MHz, CDCl$_3$) δ 158.09, 146.06, 135.94, 131.37, 130.87, 127.25 (2×CH), 126.59, 124.90, 114.56 (2×CH), 111.94, 66.94, 42.62, 41.38, 33.56, 29.55, 27.99, 25.78, 23.44, 23.31, 17.72. HRMS (ESI+): calculated for $C_{22}H_{31}BrO$ [M+H]$^+$ 391.1637 found 391.1632.

Preparation of Compound 3

According to the method for synthesis of compound 1, bakuchiol (48.2 mg, 0.301 mmol), potassium carbonate (129.9 mg, 0.94 mmol) and 1,8-dibromooctane (259 μL, 1.41 mmol) used as starting materials were prepared into compound 3 as a white oil (40.5 mg, 48%). $^1$H NMR (400 MHz, CDCl$_3$) δ 7.28 (d, J=8.8 Hz, 2H), 6.83 (d, J=8.7 Hz, 2H), 6.26 (d, J=16.3 Hz, 1H), 6.06 (d, J=16.2 Hz, 1H), 5.89 (dd, J=17.4, 10.8 Hz, 1H), 5.11 (t, J=7.1 Hz, 1H), 5.06-4.98 (m, 2H), 3.95 (t, J=6.5 Hz, 2H), 3.41 (t, J=6.8 Hz, 2H), 2.00-1.91 (m, 2H), 1.90-1.73 (m, 4H), 1.68 (s, 3H), 1.59 (s, 3H), 1.52-1.42 (m, 6H), 1.38-1.34 (m, 4H), 1.20 (s, 3H). $^{13}$C NMR (100 MHz, CDCl$_3$) δ 158.34, 146.10, 135.73, 131.39, 130.59, 127.21 (2×CH), 126.65, 124.90, 114.58 (2×CH), 111.93, 68.02, 42.62, 41.39, 34.13, 32.87, 29.32, 29.28, 28.78, 28.19, 26.04, 25.81, 23.44, 23.32, 17.74. HRMS (ESI+): calculated for $C_{26}H_{39}BrO$ [M+H]$^+$ 447.2263, found 447.2258.

Preparation of Compound 4

According to the method for synthesis of compound 1, bakuchiol (49.5 mg, 0.193 mmol), potassium carbonate (133.4 mg, 0.965 mmol) and 1,10-dibromodecane (325 μL, 1.45 mmol) used as starting materials were prepared into compound 4 as a yellow oil (46.9 mg, 52%). $^1$H NMR (400 MHz, CDCl$_3$) δ 7.27 (d, J=8.6 Hz, 2H), 6.82 (d, J=8.8 Hz, 2H), 6.25 (d, J=16.3 Hz, 1H), 6.05 (d, J=16.2 Hz, 1H), 5.87 (dd, J=17.4, 10.8 Hz, 1H), 5.13-5.07 (m, 1H), 5.04-4.97 (m, 2H), 3.93 (t, J=6.6 Hz, 2H), 3.40 (t, J=6.9 Hz, 2H), 1.99-1.89 (m, 2H), 1.89-1.70 (m, 4H), 1.67 (s, 3H), 1.57 (s, 3H), 1.52-1.39 (m, 6H), 1.37-1.29 (m, 8H), 1.19 (s, 3H). $^{13}$C NMR (100 MHz, CDCl$_3$) δ 158.37, 146.10, 135.71, 131.39, 130.56, 127.21 (2×CH), 126.66, 124.91, 114.58 (2×CH), 111.93, 68.08, 42.62, 41.39, 34.18, 32.91, 29.54, 29.45, 29.43, 29.35, 28.84, 28.25, 26.11, 25.81, 23.44, 23.32, 17.75. HRMS (ESI+): calculated for $C_{28}H_{43}BrO$ [M+H]$^+$ 475.2576, found 475.3253.

Preparation of Compound 5

Compound 2 (35 mg, 0.089 mmol) was dissolved in an anhydrous DMF (4 mL) solution. Then, dimethylamine (1 mL) was added. The mixture was stirred at 50° C. for 24 hours. After the reaction, the reaction mixture was diluted with ethyl acetate and extracted twice with water. The organic phase was concentrated under reduced pressure. The crude product was purified by RP-HPLC, to afford compound 5 as a yellow oil (23 mg, 74%). $^1$H NMR (400 MHz, CDCl$_3$) δ 7.27 (d, J=9.9 Hz, 2H), 6.82 (d, J=8.7 Hz, 2H), 6.26 (d, J=16.3 Hz, 1H), 6.05 (d, J=16.2 Hz, 1H), 5.88 (dd, J=17.4, 10.8 Hz, 1H), 5.14-5.07 (m, 1H), 5.05-4.98 (m, 2H), 3.97 (t, J=6.4 Hz, 2H), 2.36-2.30 (m, 2H), 2.23 (s, 6H), 1.99-1.92 (m, 2H), 1.85-1.76 (m, 4H), 1.67 (s, 3H), 1.58 (s, 3H), 1.52-1.47 (m, 2H), 1.19 (s, 3H). $^{13}$C NMR (100 MHz, CDCl$_3$) δ 158.30, 146.10, 135.76, 131.36, 130.65, 127.20 (2×CH), 126.65, 124.91, 114.61, 111.91, 100.00, 67.83, 59.47, 45.50 (2×CH$_3$), 42.60, 41.39, 27.25, 25.78, 24.29, 23.45, 23.31, 17.72·HRMS (ESI+): calculated for $C_{24}H_{37}NO$ [M+H]$^+$ 356.2953, found 356.2947.

Preparation of Compound 6

According to the method for synthesis of compound 5, compound 2 (35 mg, 0.089 mmol) and diethylamine (1 mL) used as starting materials were prepared into compound 6 as a yellow oil (22.3 mg, 66%). $^1$H NMR (400 MHz, CDCl$_3$) δ 7.27 (d, J=9.9 Hz, 2H), 6.82 (d, J=8.7 Hz, 2H), 6.26 (d, J=16.3 Hz, 1H), 6.05 (d, J=16.2 Hz, 1H), 5.88 (dd, J=17.4, 10.8 Hz, 1H), 5.14-5.08 (m, 1H), 5.05-4.97 (m, 2H), 3.97 (t, J=6.4 Hz, 2H), 2.61-2.46 (m, 6H), 2.00-1.92 (m, 2H), 1.82-1.74 (m, 4H), 1.67 (s, 3H), 1.58 (s, 3H), 1.52-1.46 (m, 2H), 1.19 (s, 3H), 1.03 (t, J=7.2 Hz, 6H). $^{13}$C NMR (100 MHz, CDCl$_3$) δ 158.27, 146.09, 135.79, 131.36, 130.68, 127.21 (2×CH), 126.64, 124.90, 114.60 (2×CH), 111.91, 67.85, 52.48, 46.85 (2×CH$_2$), 42.60, 41.39, 27.40, 25.78 (2×CH$_2$), 23.45, 23.31, 17.72, 11.46 (2×CH$_3$). HRMS (ESI+): calculated for $C_{26}H_{41}NO$ [M+H]$^+$ 384.3266, found 384.3260.

Preparation of Compound 7

According to the method for synthesis of compound 9, compound 2 (62.1 mg, 0.159 mmol) and dibutylamine (1 mL) used as starting materials were prepared into compound 7 as a yellow oil (59.1 mg, 88%). $^1$H NMR (400 MHz, CDCl$_3$) δ 7.28 (d, J=8.7 Hz, 2H), 6.83 (d, J=8.7 Hz, 2H), 6.26 (d, J=16.3 Hz, 1H), 6.05 (d, J=16.2 Hz, 1H), 5.88 (dd, J=17.4, 10.8 Hz, 1H), 5.14-5.07 (m, 1H), 5.06-4.97 (m, 2H), 3.96 (t, J=6.5 Hz, 2H), 2.51-2.44 (m, 2H), 2.43-2.37 (m, 4H), 1.99-1.91 (m, 2H), 1.83-1.69 (m, 4H), 1.67 (s, 3H), 1.58 (s, 3H), 1.52-1.46 (m, 2H), 1.45-1.37 (m, 4H), 1.35-1.28 (m, 4H), 1.19 (s, 3H), 0.91 (t, J=7.3 Hz, 6H). $^{13}$C NMR (100 MHz,) δ 158.31, 146.10, 135.76, 131.36, 130.64, 127.20 (2×CH), 126.66, 124.91, 114.61 (2×CH), 111.91, 67.93, 53.81 (2×CH$_2$), 53.76, 42.60, 41.39, 29.79, 29.03, 27.36, 25.78 (2×CH$_2$), 23.45, 23.31, 20.82 (2×CH$_2$), 17.72, 14.16 (2×CH₃). HRMS (ESI+): calculated for C₃₀H₄₉NO [M+H]⁺ 440.3892, found 440.3892.

Preparation of Compound 8

According to the method for synthesis of compound 5, compound 1 (49 mg, 0.130 mmol) and diethylamine (1 mL) used as starting materials were prepared into compound 8. The crude product was purified by silica gel column chromatography (ethyl acetate/ethanol, 1:1, v/v) as a yellow oil (38.6 mg, 87%). ¹H NMR (400 MHz, CDCl₃) δ 7.25 (d, J=8.7 Hz, 2H), 6.81 (d, J=8.6 Hz, 2H), 6.23 (d, J=16.2 Hz, 1H), 6.03 (d, J=16.2 Hz, 1H), 5.86 (dd, J=17.4, 10.8 Hz, 1H), 5.08 (t, J=6.6 Hz, 1H), 5.05-4.95 (m, 2H), 3.98 (t, J=6.4 Hz, 2H), 2.47-2.41 (m, 2H), 2.24 (s, 6H), 1.98-1.89 (m, 4H), 1.65 (s, 3H), 1.56 (s, 3H), 1.50-1.43 (m, 2H), 1.17 (s, 3H). ¹³C NMR (100 MHz, CDCl₃) δ 158.24, 146.09, 135.80, 131.36, 130.71, 127.21 (2×CH), 126.64, 124.91, 114.60 (2×CH), 111.91, 66.32, 56.49, 45.53 (2×CH₃), 42.60, 41.39, 27.57, 25.78, 23.44, 23.31, 17.72. HRMS (ESI+): calculated for C₂₃H₃₅NO [M+H]⁺ 342.2797, found 342.2791.

Preparation of Compound 9

According to the method for synthesis of compound 5, compound 1 (59.6 mg, 0.158 mmol) and diethylamine (1 mL) used as starting materials were prepared into compound 9 as a yellow oil (48.9 mg, 91%). ¹H NMR (400 MHz, CDCl₃) δ 7.28 (d, J=8.7 Hz, 2H), 6.83 (d, J=8.7 Hz, 2H), 6.26 (d, J=16.3 Hz, 1H), 6.06 (d, J=16.2 Hz, 1H), 5.88 (dd, J=17.4, 10.8 Hz, 1H), 5.15-5.08 (m, 1H), 5.06-4.97 (m, 2H), 4.00 (t, J=6.3 Hz, 2H), 2.64-2.51 (m, 6H), 2.00-1.88 (m, 4H), 1.67 (s, 3H), 1.58 (s, 3H), 1.52-1.46 (m, 2H), 1.20 (s, 3H), 1.04 (t, J=7.1 Hz, 6H). ¹³C NMR (100 MHz, CDCl₃) δ 158.33, 146.10, 135.74, 131.35, 130.63, 127.19 (2×CH), 126.67, 124.91, 114.61 (2×CH), 111.91, 66.49, 49.46, 47.09 (2×CH₂), 42.60, 41.39, 27.06, 25.78, 23.45, 23.32, 17.72, 11.84 (2×CH₃). HRMS (ESI+): calculated for C₂₅H₃₉NO [M+H]⁺ 370.3110, found 370.3103.

Preparation of Compound 10

According to the method for synthesis of compound 5, compound 1 (59.5 mg, 0.158 mmol) and dibutylamine (1 mL) used as starting materials were prepared into compound 10 as a colorless clear oil (56 mg, 86%). ¹H NMR (400 MHz, CDCl₃) δ 7.28 (d, J=8.7 Hz, 2H), 6.83 (d, J=8.7 Hz, 2H), 6.26 (d, J=16.3 Hz, 1H), 6.06 (d, J=16.2 Hz, 1H), 5.89 (dd, J=17.4, 10.8 Hz, 1H), 5.15-5.08 (m, 1H), 5.06-4.98 (m, 2H), 4.00 (t, J=6.4 Hz, 2H), 2.61-2.54 (m, 2H), 2.44-2.38 (m, 4H), 1.97-1.87 (m, 4H), 1.68 (s, 3H), 1.59 (s, 3H), 1.52-1.46 (m, 2H), 1.44-1.38 (m, 4H), 1.33-1.28 (m, 4H), 1.20 (s, 3H), 0.90 (t, J=7.3 Hz, 6H). ¹³C NMR (100 MHz, CDCl₃) δ 158.36, 146.11, 135.70, 131.35, 130.59, 127.18 (2×CH), 126.69, 124.92, 114.61 (2×CH), 111.90, 66.45, 54.06 (2×CH₂), 50.63, 42.60, 41.40, 29.38, 27.17, 25.78 (2×CH₂), 23.46, 23.32, 20.81 (2×CH₂), 17.72, 14.18 (2×CH₃). HRMS (ESI+): calculated for C₂₉H₄₇NO [M+H]⁺ 426.3736, found 426.3728.

Preparation of Compound 11

According to the method for synthesis of compound 5, compound 3 (40.5 mg, 0.091 mmol) and diethylamine (1 mL) used as starting materials were prepared into compound 11 as a yellow oil (32.3 mg, 81%). ¹H NMR (400 MHz, CD₃OD) δ 7.27 (d, J=8.7 Hz, 2H), 6.82 (d, J=8.7 Hz, 2H), 6.26 (d, J=16.3 Hz, 1H), 6.07 (d, J=16.3 Hz, 1H), 5.90 (dd, J=17.4, 10.8 Hz, 1H), 5.15-5.08 (m, 1H), 5.05-4.98 (m, 2H), 3.95 (t, J=6.4 Hz, 2H), 2.89 (q, J=7.3 Hz, 4H), 2.81-2.75 (m, 2H), 2.00-1.92 (m, 2H), 1.81-1.72 (m, 2H), 1.66 (s, 3H), 1.62-1.55 (m, 5H), 1.51-1.45 (m, 4H), 1.42-1.34 (m, 6H), 1.20-1.15 (m, 9H). ¹³C NMR (100 MHz, CD₃OD) δ 159.78, 147.33, 136.40, 131.99, 131.82, 128.15 (2×CH), 128.01, 125.94, 115.50 (2×CH), 112.28, 68.86, 53.35, 47.95 (2×CH₂), 43.54, 42.57, 30.36 (2×CH₂), 30.30, 28.09, 27.07, 25.90 (2×CH₂), 24.36, 23.86, 17.69, 10.06 (2×CH₃). HRMS (ESI+): calculated for C₃₀H₄₉NO [M+H]⁺ 440.3892, found 440.3875.

Preparation of Compound 12

According to the method for synthesis of compound 5, compound 4 (46.9 mg, 0.099 mmol) and diethylamine (1 mL) used as starting materials were prepared into compound 12 as an orange oil (34.8 mg, 76%). ¹H NMR (400 MHz, CD₃OD) δ 7.26 (d, J=8.7 Hz, 2H), 6.82 (d, J=8.7 Hz, 2H), 6.26 (d, J=16.3 Hz, 1H), 6.07 (d, J=16.3 Hz, 1H), 5.90 (dd, J=17.4, 10.8 Hz, 1H), 5.15-5.08 (m, 1H), 5.06-4.97 (m, 2H), 3.94 (t, J=6.4 Hz, 2H), 3.18 (q, J=7.3 Hz, 4H), 3.11-3.02 (m, 2H), 2.02-1.91 (m, 2H), 1.82-1.60 (m, 7H), 1.57 (s, 3H), 1.52-1.42 (m, 4H), 1.42-1.33 (m, 10H), 1.29 (t, J=7.3 Hz, 6H), 1.19 (s, 3H). ¹³C NMR (100 MHz, CD₃OD) δ 159.78, 147.31, 136.39, 131.98, 131.79, 128.15 (2×CH), 128.00, 125.94, 115.49 (2×CH), 112.29, 68.91, 52.95, 48.15 (2×CH₂), 43.54, 42.56, 30.55, 30.44 (2×CH₂), 30.41, 30.20, 27.64, 27.15, 25.92, 24.91, 24.35, 23.85, 17.70, 9.08 (2×CH₃). HRMS (ESI+): calculated for C₃₂H₅₃NO [M+H]⁺ 468.4205, found 468.4199.

Preparation of Compound 13

According to the method for synthesis of compound 24, compound 2 (69.3 mg, 0.177 mmol) and ammonia water (3 mL) used as starting materials were prepared into compound 13 as a yellow foam (44.8 mg, 77%). ¹H NMR (400 MHz, CD₃OD) δ 7.28 (d, J=8.7 Hz, 2H), 6.88-6.83 (m, 2H), 6.26 (d, J=16.3 Hz, 1H), 6.08 (d, J=16.3 Hz, 1H), 5.90 (dd, J=17.5, 10.8 Hz, 1H), 5.14-5.09 (m, 1H), 5.05-4.99 (m, 2H), 4.03 (t, J=5.3 Hz, 2H), 3.13-3.06 (m, 2H), 2.00-1.84 (m, 6H), 1.66 (s, 3H), 1.57 (s, 3H), 1.50-1.45 (m, 2H), 1.19 (s, 3H). ¹³C NMR (100 MHz, CD₃OD) δ 159.44, 147.28, 136.63, 132.14, 131.98, 128.18 (2×CH), 127.92, 125.93, 115.51 (2×CH), 112.29, 68.17, 43.54, 42.54, 40.52, 27.29, 25.89, 25.69, 24.35, 23.86, 17.68. HRMS (ESI+): calculated for C₂₂H₃₃NO [M+H]⁺ 328.2640, found 328.2632.

Preparation of Compound 14

According to the method for synthesis of compound 5, compound 2 (38.9 mg, 0.099 mmol) and ethylamine (1 mL) used as starting materials were prepared into compound 14 as a yellow oil (30.1 mg, 85%). ¹H NMR (400 MHz, CD₃OD) δ 7.28 (d, J=8.7 Hz, 2H), 6.85 (d, J=8.7 Hz, 2H), 6.26 (d, J=16.3 Hz, 1H), 6.08 (d, J=16.3 Hz, 1H), 5.90 (dd, J=17.5, 10.8 Hz, 1H), 5.12 (t, J=7.2 Hz, 1H), 5.05-4.97 (m, 2H), 4.02 (t, J=5.3 Hz, 2H), 3.11-2.98 (m, 4H), 2.00-1.92 (m, 2H), 1.91-1.81 (m, 4H), 1.66 (s, 3H), 1.57 (s, 3H), 1.51-1.44 (m, 2H), 1.31 (t, J=7.3 Hz, 3H), 1.19 (s, 3H). ¹³C NMR (100 MHz, CD₃OD) δ 159.44, 147.31, 136.69, 132.20, 132.00, 128.21 (2×CH), 127.93, 125.95, 115.54 (2×CH), 112.31, 68.12, 48.22, 43.94, 43.56, 42.56, 27.38, 25.90, 24.44, 24.36, 23.87, 17.69, 11.56. HRMS (ESI+): calculated for $C_{24}H_{37}NO$ [M+H]$^+$ 356.2953, found 356.2949.

Preparation of Compound 15

According to the method for synthesis of compound 5, compound 2 (43 mg, 0.11 mmol) and n-butylamine (1 mL) used as starting materials were prepared into compound 15 as a yellow oil (35.5 mg, 84%). $^1$H NMR (400 MHz, CD$_3$OD) δ 7.28 (d, J=7.3 Hz, 2H), 6.85 (d, J=8.4 Hz, 2H), 6.26 (d, J=15.8 Hz, 1H), 6.12-6.03 (m, 1H), 5.96-5.84 (m, 1H), 5.11 (t, J=7.8 Hz, 1H), 5.05-4.98 (m, 2H), 4.06-3.99 (m, 2H), 3.08-3.00 (m, 2H), 3.00-2.93 (m, 2H), 2.00-1.91 (m, 2H), 1.90-1.80 (m, 4H), 1.70-1.61 (m, 5H), 1.57 (s, 3H), 1.50-1.37 (m, 4H), 1.20-1.17 (m, 3H), 1.01-0.95 (m, 3H). $^{13}$C NMR (100 MHz, CD$_3$OD) δ 159.41, 147.28, 136.67, 132.16, 132.00, 128.19 (2×CH), 127.90, 125.92, 115.54 (2×CH), 112.30, 68.14, 48.74 (2×CH$_2$), 43.53, 42.53, 29.44, 27.41, 25.89, 24.48, 24.33, 23.85, 20.84, 17.68, 13.92. HRMS (ESI+): calculated for $C_{26}H_{41}NO$ [M+H]$^+$ 384.3266, found 384.3261.

Preparation of Compound 16

According to the method for synthesis of compound 5, compound 2 (65.8 mg, 0.168 mmol) and n-hexylamine (1 mL) used as starting materials were prepared into compound 16 as a yellow oil (46.7 mg, 68%). $^1$H NMR (400 MHz, CDCl$_3$) δ 7.24 (d, J=8.1 Hz, 2H), 6.76 (d, J=8.7 Hz, 2H), 6.23 (d, J=16.3 Hz, 1H), 6.03 (d, J=16.2 Hz, 1H), 5.86 (dd, J=17.4, 10.8 Hz, 1H), 5.13-5.06 (m, 1H), 5.04-4.96 (m, 2H), 3.89 (t, J=5.9 Hz, 2H), 2.98-2.80 (m, 4H), 1.98-1.86 (m, 4H), 1.82-1.65 (m, 7H), 1.56 (s, 3H), 1.50-1.44 (m, 2H), 1.31-1.21 (m, 6H), 1.17 (s, 3H), 0.84 (t, J=6.8 Hz, 3H). $^{13}$C NMR (100 MHz, CDCl$_3$) δ 168.26, 157.88, 146.03, 135.96, 131.36, 130.96, 127.25, 126.56, 124.88, 114.54 (2×CH), 111.95, 67.04, 47.65, 47.28, 42.60, 41.37, 31.28, 26.58, 26.51, 25.99, 25.78, 23.41, 23.30, 23.10, 22.50, 17.71, 14.00. HRMS (ESI+): calculated for $C_{28}H_{45}NO$ [M+H]$^+$ 412.3579, found 412.3573.

Preparation of Compound 17

According to the method for synthesis of compound 5, compound 2 (34.7 mg, 0.089 mmol) and n-octylamine (1 mL) used as starting materials were prepared into compound 17 as a yellow oil (28.4 mg, 72%). $^1$H NMR (400 MHz, CD$_3$OD) δ 7.25 (d, J=8.8 Hz, 2H), 6.82 (d, J=8.8 Hz, 2H), 6.24 (d, J=16.3 Hz, 1H), 6.05 (d, J=16.3 Hz, 1H), 5.88 (dd, J=17.4, 10.8 Hz, 1H), 5.12-5.06 (m, 1H), 5.04-4.95 (m, 2H), 4.07-3.92 (m, 2H), 3.08-2.76 (m, 4H), 1.99-1.78 (m, 6H), 1.63 (s, 5H), 1.55 (s, 3H), 1.48-1.42 (m, 2H), 1.36-1.26 (m, 10H), 1.17 (s, 3H), 0.88 (t, J=6.9 Hz, 3H). $^{13}$C NMR (100 MHz, CD$_3$OD) δ 159.44, 147.30, 136.67, 132.18, 131.99, 128.20, 127.93, 125.94, 115.54 (2×CH), 112.29, 101.33, 68.17, 48.55, 48.54, 43.55, 42.55, 32.90, 30.24, 30.20, 30.19, 27.68, 27.45, 25.88, 24.35, 23.87, 23.68, 23.67, 17.67, 14.41.
HRMS (ESI+): calculated for $C_{30}H_{49}NO$ [M+H]$^+$ 440.3892, found 440.3886.

Preparation of Compound 18

According to the method for synthesis of compound 5, compound 2 (66.7 mg, 0.170 mmol) and n-decylamine (1 mL) used as starting materials were prepared into compound 18 as a yellow oil (64.8 mg, 81%). $^1$H NMR (400 MHz, CDCl$_3$) δ 7.26-7.23 (m, 2H), 6.77 (d, J=8.8 Hz, 2H), 6.24 (d, J=16.2 Hz, 1H), 6.04 (d, J=16.2 Hz, 1H), 5.87 (dd, J=17.4, 10.7 Hz, 1H), 5.13-5.07 (m, 1H), 5.04-4.97 (m, 2H), 3.90 (t, J=5.9 Hz, 2H), 2.99-2.90 (m, 2H), 2.89-2.81 (m, 2H), 1.99-1.85 (m, 4H), 1.84-1.60 (m, 7H), 1.57 (s, 3H), 1.51-1.45 (m, 2H), 1.29-1.18 (m, 17H), 0.86 (t, J=6.9 Hz, 3H). $^{13}$C NMR (100 MHz, CDCl$_3$) δ 167.98, 157.87, 146.01, 135.97, 131.35, 130.96, 127.25, 126.56, 124.88, 114.54 (2×CH), 111.95, 67.04, 47.68, 47.32, 42.60, 41.36, 31.95, 29.56, 29.52, 29.35, 29.18, 26.87, 26.57, 26.05, 25.78, 23.41, 23.30, 23.11, 22.74, 17.71, 14.19. HRMS (ESI+): calculated for $C_{32}H_{53}NO$ [M+H]$^+$ 468.4205, found 468.4197.

Preparation of Compound 19

According to the method for synthesis of compound 8, compound 2 (47.3 mg, 0.121 mmol) and thiomorpholine (1 mL) used as starting materials were prepared into compound 19 as a yellow oil (39.5 mg, 81%). $^1$H NMR (400 MHz, CDCl$_3$) δ 7.28 (d, J=8.7 Hz, 2H), 6.82 (d, J=8.7 Hz, 2H), 6.26 (d, J=16.3 Hz, 1H), 6.06 (d, J=16.2 Hz, 1H), 5.88 (dd, J=17.4, 10.8 Hz, 1H), 5.15-5.07 (m, 1H), 5.06-4.96 (m, 2H), 3.96 (t, J=6.3 Hz, 2H), 2.75-2.61 (m, 8H), 2.46-2.38 (m, 2H), 2.00-1.91 (m, 2H), 1.81-1.73 (m, 2H), 1.70-1.62 (m, 5H), 1.58 (s, 3H), 1.52-1.45 (m, 2H), 1.20 (s, 3H). $^{13}$C NMR (100 MHz, CDCl$_3$) δ 158.24, 146.08, 135.82, 131.36, 130.70, 127.22 (2×CH), 126.63, 124.90, 114.58 (2×CH), 111.93, 67.77, 58.99, 55.08 (2×CH$_2$), 42.61, 41.39, 28.07 (2×CH$_2$), 27.31, 25.79, 23.45, 23.32, 23.13, 17.73. HRMS (ESI+): calculated for $C_{26}H_{39}NOS$ [M+H]$^+$ 414.2831, found 414.2822.

Preparation of Compound 20

According to the method for synthesis of compound 5, compound 2 (47.3 mg, 0.121 mmol) and tetrahydropyrrole (1 mL) used as starting materials were prepared into compound 20 as a colorless clear oil (40.5 mg, 88%). $^1$H NMR (400 MHz, CDCl$_3$) δ 7.27 (d, J=8.7 Hz, 2H), 6.84 (d, J=8.7 Hz, 2H), 6.26 (d, J=16.3 Hz, 1H), 6.07 (d, J=16.3 Hz, 1H), 5.90 (dd, J=17.4, 10.8 Hz, 1H), 5.15-5.07 (m, 1H), 5.05-4.97 (m, 2H), 4.00 (t, J=5.6 Hz, 2H), 2.88 (dt, J=15.1, 6.7 Hz, 6H), 1.99-1.88 (m, 6H), 1.83-1.76 (m, 4H), 1.66 (s, 3H), 1.57 (s, 3H), 1.50-1.44 (m, 2H), 1.19 (s, 3H). $^{13}$C NMR (100 MHz, CDCl$_3$) δ 159.55, 147.30, 136.57, 132.04, 131.97, 128.18 (2×CH), 127.96, 125.95, 115.55 (2×CH), 112.30, 68.38, 56.69, 54.98 (2×CH$_2$), 43.54, 42.55, 28.00, 25.90, 25.32, 24.35, 24.06 (2×CH$_2$), 23.88, 17.70. HRMS (ESI+): calculated for $C_{26}H_{39}NO$ [M+H]$^+$ 382.3110, found 382.3101.

Preparation of Compound 21

According to the method for synthesis of compound 5, compound 2 (66.3 mg, 0.169 mmol) and 1-methylpiperazine (1 mL) used as starting materials were prepared into compound 21 as a brown oil (48.7 mg, 71%). $^1$H NMR (400 MHz, CDCl$_3$) δ 7.28-7.25 (m, 2H), 6.79 (d, J=8.7 Hz, 2H), 6.24 (d, J=16.3 Hz, 1H), 6.04 (d, J=16.2 Hz, 1H), 5.86 (dd, J=17.4, 10.8 Hz, 1H), 5.12-5.05 (m, 1H), 5.03-4.96 (m, 2H), 3.94 (t, J=6.1 Hz, 2H), 2.88-2.45 (m, 10H), 2.43 (s, 3H), 1.98-1.88 (m, 2H), 1.82-1.67 (m, 4H), 1.65 (s, 3H), 1.56 (s, 3H), 1.50-1.44 (m, 2H), 1.17 (s, 3H). $^{13}$C NMR (100 MHz, CDCl$_3$) δ 167.96, 158.13, 146.05, 135.88, 131.37, 130.76, 127.23, 126.58, 124.88, 114.55 (2×CH), 111.94, 67.53, 57.50, 53.62 (2×CH$_2$), 51.37 (2×CH$_2$), 44.64, 42.61, 41.37, 27.14, 25.79, 23.42, 23.30, 22.91, 17.72. HRMS (ESI+): calculated for $C_{27}H_{42}N_2O$ [M+H]$^+$ 411.3375, found 411.3365.

Preparation of Compound 22

According to the method for synthesis of compound 5, compound 2 (66.3 mg, 0.169 mmol) and dimethylpyridinamine (1 mL) used as starting materials were prepared into compound 22 as a brown gel (71.4 mg, 83%). $^1$H NMR (400 MHz, CDCl$_3$) δ 8.53-8.48 (m, 2H), 7.65-7.58 (m, 2H), 7.51 (d, J=7.8 Hz, 2H), 7.26-7.22 (m, 2H), 7.15-7.08 (m, 2H), 6.75 (d, J=8.7 Hz, 2H), 6.24 (d, J=16.3 Hz, 1H), 6.04 (d, J=16.2 Hz, 1H), 5.87 (dd, J=17.4, 10.8 Hz, 1H), 5.13-5.06 (m, 1H), 5.04-4.96 (m, 2H), 3.85 (t, J=6.2 Hz, 2H), 3.81 (s, 4H), 2.59 (t, J=6.9 Hz, 2H), 1.99-1.89 (m, 2H), 1.80-1.62 (m, 7H), 1.56 (s, 3H), 1.51-1.44 (m, 2H), 1.18 (s, 3H). $^{13}$C NMR (100 MHz, CDCl$_3$) δ 159.94, 158.24 (2×C), 149.02 (2×CH), 146.08, 136.51 (2×CH), 135.75, 131.36, 130.61, 127.18 (2×CH), 126.65, 124.90, 123.01 (2×CH), 122.02 (2×CH), 114.58 (2×CH), 111.93, 67.74, 60.50 (2×CH$_2$), 53.96, 42.61, 41.38, 27.04, 25.79, 23.70, 23.44, 23.31, 17.73. HRMS ((ESI+): calculated for $C_{34}H_{43}N_3O$ [M+H]$^+$ 510.3484, found 510.3478.

Preparation of Compound 23

According to the method for synthesis of compound 5, compound 2 (67.6 mg, 0.173 mmol) and 1-(3-dimethylaminopropyl)piperazine (1 mL) used as starting materials were prepared into compound 23 as a brown gel (68.4 mg, 83%). $^1$H NMR (400 MHz, CDCl$_3$) δ 7.27-7.23 (m, 2H), 6.79 (d, J=8.5 Hz, 2H), 6.23 (d, J=16.2 Hz, 1H), 6.03 (d, J=16.2 Hz, 1H), 5.85 (dd, J=17.4, 10.8 Hz, 1H), 5.11-5.05 (m, 1H), 5.03-4.94 (m, 2H), 3.93 (t, J=6.1 Hz, 2H), 2.63-2.39 (m, 20H), 1.97-1.88 (m, 2H), 1.82-1.73 (m, 4H), 1.69-1.62 (m, 5H), 1.55 (s, 3H), 1.49-1.42 (m, 2H), 1.17 (s, 3H). $^{13}$C NMR (100 MHz, CDCl$_3$) δ 168.54, 158.19, 146.06, 135.80, 131.36, 130.68, 127.21, 126.61, 124.88, 114.56 (2×CH), 111.92, 67.67, 57.96, 56.62, 55.66, 52.62 (2×CH$_2$), 43.90 (2×CH$_3$), 42.60, 41.37, 27.28, 25.78, 23.43, 23.30, 23.16, 23.07, 17.72. HRMS (ESI+): calculated for $C_{31}H_{51}N_3O$ [M+H]$^+$ 482.4110, found 482.4101.

Preparation of Compound 24

According to the method for synthesis of compound 5, compound 2 (63.6 mg, 0.163 mmol) and N,N'-dimethyl-1,3-propanediamine (203 μL, 1.62 mmol) used as starting materials were prepared into compound 24 as a yellow oil (56.5 mg, 87%). $^1$H NMR (400 MHz, CD$_3$OD) δ 7.27 (dd, J=8.7, 1.9 Hz, 2H), 6.84 (d, J=8.8 Hz, 2H), 6.26 (d, J=16.3 Hz, 1H), 6.07 (d, J=16.3 Hz, 1H), 5.90 (dd, J=17.4, 10.8 Hz, 1H), 5.15-5.09 (m, 1H), 5.06-4.98 (m, 2H), 4.03-3.95 (m, 2H), 3.37-3.31 (m, 2H), 2.98-2.84 (m, 2H), 2.60-2.36 (m, 5H), 2.33-2.24 (m, 3H), 2.00-1.92 (m, 2H), 1.85-1.67 (m, 6H), 1.66 (s, 3H), 1.57 (s, 3H), 1.51-1.45 (m, 2H), 1.19 (s, 3H). $^{13}$C NMR (100 MHz, CDCl$_3$) δ 157.84, 145.92, 136.05, 131.38, 130.90, 127.30 (2×CH), 126.43, 124.83, 114.54 (2×CH), 112.03, 67.10, 55.01, 47.70, 45.12, 43.16, 42.98, 42.60, 41.31, 26.45, 25.82 (2×CH$_2$), 23.29, 23.17, 21.76, 17.75. HRMS ((ESI+): calculated for $C_{27}H_{44}N_2O$ [M+H]$^+$ 413.3532, found 413.3523.

Preparation of Compound 25

According to the method for synthesis of compound 24, compound 2 (47 mg, 0.12 mmol) and 2-(methylthio)ethylamine (55.8 μL, 0.600 mmol) used as starting materials were prepared into compound 25 as a yellow oil (23.2 mg, 60%). $^1$H NMR (400 MHz, CDCl$_3$) δ 7.27 (d, J=8.8 Hz, 2H), 6.82 (d, J=8.8 Hz, 2H), 6.25 (d, J=16.3 Hz, 1H), 6.05 (d, J=16.2 Hz, 1H), 5.88 (dd, J=17.4, 10.8 Hz, 1H), 5.13-5.07 (m, 1H), 5.05-4.98 (m, 2H), 3.96 (t, J=6.3 Hz, 2H), 2.85 (t, J=6.5 Hz, 2H), 2.73-2.61 (m, 4H), 2.23 (s, 3H), 2.10-2.10 (m, 2H), 1.98-1.91 (m, 2H), 1.86-1.77 (m, 2H), 1.73-1.69 (m, 1H), 1.67 (s, 3H), 1.57 (s, 3H), 1.51-1.46 (m, 2H), 1.19 (s, 3H). $^{13}$C NMR (100 MHz, CDCl$_3$) δ 158.20, 146.07, 135.81, 131.38, 130.70, 127.22 (2×CH), 126.62, 124.89, 114.58 (2×CH), 111.93, 67.75, 49.10, 47.65, 42.61, 41.38, 34.12, 27.11, 26.51, 25.79, 23.43, 23.31, 17.73, 15.36. HRMS (ESI+): calculated for $C_{25}H_{39}NOS$ [M+H]$^+$ 402.2831, found 402.2822.

Preparation of Compound 26

According to the method for synthesis of compound 24, compound 2 (60.65 mg, 0.155 mmol) and N,N,N'-trimethyl-1,3-propanediamine (113.5 μL, 0.775 mmol) used as starting materials were prepared into compound 26 as a yellow oil (46.3 mg, 70%). $^1$H NMR (400 MHz, CD$_3$OD) δ 7.29 (d, J=8.7 Hz, 2H), 6.86 (d, J=8.8 Hz, 2H), 6.26 (d, J=16.3 Hz, 1H), 6.08 (d, J=16.3 Hz, 1H), 5.90 (dd, J=17.4, 10.8 Hz, 1H), 5.15-5.09 (m, 1H), 5.06-4.98 (m, 2H), 4.03 (t, J=5.5 Hz, 2H), 3.07-2.97 (m, 6H), 2.73-2.69 (m, 9H), 2.07-1.92 (m, 4H), 1.90-1.81 (m, 4H), 1.66 (s, 3H), 1.57 (s, 3H), 1.51-1.44 (m, 2H), 1.19 (s, 3H). $^{13}$C NMR (100 MHz, CD$_3$OD) δ 159.47, 147.29, 136.65, 132.13, 131.99, 128.20 (2×CH), 127.92, 125.94, 115.55 (2×CH), 112.30, 68.20, 57.45, 43.87, 43.81, 43.55 (3×CH$_3$), 42.54, 40.78, 27.58, 25.89, 24.35, 23.84, 22.92, 21.62, 17.69. HRMS (ESI+): calculated for $C_{28}H_{46}N_2O$ [M+H]$^+$ 427.3688, found 427.3679.

Preparation of Compound 27

According to the method for synthesis of compound 5, compound 2 (67.1 mg, 0.171 mmol) and N,N',N''-trimethyldipropylenetriamine (208 μL, 1.03 mmol) used as starting materials were prepared into compound 27 as a yellow oil (58.3 mg, 72%). $^1$H NMR (400 MHz, CD$_3$OD) δ 7.28 (d, J=8.7 Hz, 2H), 6.85 (d, J=8.7 Hz, 2H), 6.26 (d, J=16.3 Hz, 1H), 6.08 (d, J=16.3 Hz, 1H), 5.90 (dd, J=17.4, 10.8 Hz, 1H), 5.16-5.09 (m, 1H), 5.06-4.98 (m, 2H), 4.01 (t, J=5.2 Hz, 2H), 3.38-3.31 (m, 2H), 2.99-2.84 (m, 2H), 2.82-2.61 (m, 5H), 2.56-2.36 (m, 7H), 2.34-2.23 (m, 3H), 2.00-1.90 (m, 2H), 1.85-1.72 (m, 8H), 1.66 (s, 3H), 1.57 (s, 3H), 1.51-1.45 (m, 2H), 1.19 (s, 3H). $^{13}$C NMR (100 MHz, CDCl$_3$) δ 157.79, 145.96, 136.06, 131.41, 130.97, 127.29 (2×CH), 126.44, 124.82, 114.48 (2×CH), 112.00, 66.92, 55.61, 54.00, 53.58, 53.38, 47.60, 42.61 (2×CH$_3$), 41.32, 40.89, 39.50, 33.14, 26.52, 25.81, 23.32, 23.28, 22.09, 20.99, 17.73. HRMS (ESI+): calculated for $C_{31}H_{53}N_3O$ [M+H]$^+$ 484.4267, found 484.4258.

Preparation of Compound 28

According to the method for synthesis of compound 24, compound 2 (56 mg, 0.143 mmol) and N'-[3-(dimethylamino)propyl]-N,N-dimethyl-1,3-propanediamine (159 μL, 0.715 mmol) used as starting materials were prepared into compound 28 as a yellow gel (67.1 mg, 94%). $^1$H NMR (400 MHz, CD$_3$OD) δ 7.32-7.27 (m, 2H), 6.91-6.83 (m, 2H), 6.27 (d, J=16.2 Hz, 1H), 6.14-6.05 (m, 1H), 5.90 (dd, J=17.5, 10.8 Hz, 1H), 5.16-5.08 (m, 1H), 5.06-4.98 (m, 2H), 4.12-

3.98 (m, 2H), 3.50-3.38 (m, 3H), 3.21-2.97 (m, 9H), 2.87-2.72 (m, 10H), 2.24-1.73 (m, 10H), 1.66 (s, 3H), 1.57 (s, 3H), 1.50-1.45 (m, 2H), 1.19 (s, 3H). $^{13}$C NMR (100 MHz, CD$_3$OD) δ 159.57, 159.37, 147.28, 136.63, 131.99, 128.21, 127.90, 127.88, 125.92, 115.56, 115.54, 112.30, 68.53, 67.96, 51.59, 51.37, 51.32, 43.55 (2×CH$_3$), 43.41, 43.40, 43.35 (2×CH$_3$), 42.53, 27.13, 25.89, 25.87, 24.34, 23.83, 20.73, 17.68, 17.66. HRMS (ESI+): calculated for C$_{32}$H$_{55}$N$_3$O [M+H]$^+$ 498.4423, found 498.4411.

Preparation of Compound 29

According to the method for synthesis of compound 24, compound 2 (50 mg, 0.128 mmol) and tris(2-aminoethyl)amine (96 μL, 0.639 mmol) used as starting materials were prepared into compound 29 as a yellow gel (37.4 mg, 64%). $^1$H NMR (400 MHz, CD$_3$OD) δ 7.28 (d, J=8.6 Hz, 2H), 6.85 (d, J=8.7 Hz, 2H), 6.26 (d, J=16.2 Hz, 1H), 6.08 (d, J=16.2 Hz, 1H), 5.90 (dd, J=17.5, 10.7 Hz, 1H), 5.12 (t, J=7.2 Hz, 1H), 5.05-5.01 (m, 2H), 4.02 (t, J=5.5 Hz, 2H), 3.18-3.01 (m, 8H), 2.87-2.72 (m, 6H), 2.00-1.82 (m, 6H), 1.66 (s, 3H), 1.57 (s, 3H), 1.51-1.44 (m, 2H), 1.19 (s, 3H). $^{13}$C NMR (100 MHz, CD$_3$OD) δ 159.44, 147.28, 136.62, 132.11, 132.00, 128.18 (2×CH), 127.91, 125.92, 115.53 (2×CH), 112.29, 68.13, 52.53 (2×CH$_2$), 51.52, 46.28, 43.54 (3×CH$_2$), 42.53, 38.07, 27.52, 25.89, 24.42, 24.34, 23.84, 17.67. HRMS (ESI+): calculated for C$_{28}$H$_{48}$N$_4$O [M+H]$^+$ 457.3906, found 457.3890.

Preparation of Compound 30

According to the method for synthesis of compound 24, compound 2 (36.7 mg, 0.094 mmol) and 1,4,8,11-tetraazacyclotetradecane (147 μL, 0.75 mmol) used as starting materials were prepared into compound 30 as a yellow gel (29.8 mg, 62%). $^1$H NMR (400 MHz, CD$_3$OD) δ 7.29 (d, J=8.7 Hz, 2H), 6.87 (d, J=8.8 Hz, 2H), 6.27 (d, J=16.3 Hz, 1H), 6.09 (d, J=16.3 Hz, 1H), 5.91 (dd, J=17.5, 10.8 Hz, 1H), 5.15-5.10 (m, 1H), 5.05-4.99 (m, 2H), 4.08-3.98 (m, 2H), 3.58-3.35 (m, 2H), 3.24-3.09 (m, 6H), 2.99-2.50 (m, 10H), 2.00-1.64 (m, 13H), 1.57 (s, 3H), 1.50-1.44 (m, 2H), 1.20 (s, 3H). $^{13}$C NMR (100 MHz,) δ 159.55, 147.28, 136.67, 132.09, 132.00, 128.22 (2×CH), 127.89, 125.92, 115.56 (2×CH), 112.30, 68.42, 54.07, 51.98, 51.76, 50.65, 50.44, 47.44 (2×CH$_2$), 45.94, 45.76, 43.55, 42.54, 28.04, 25.89, 25.47, 24.35, 23.84, 23.36, 21.34, 17.68. HRMS ((ESI+): calculated for C$_{32}$H$_{54}$N$_4$O [M+H]$^+$ 511.4376, found 511.4367.

Preparation of Compound 31

According to the method for synthesis of compound 24, compound 2 (56 mg, 0.143 mmol) and 1,4,7,10,13-pentazacyclopentadecane (176.3 μL, 0.715 mmol) used as starting materials were prepared into compound 31 as a yellow gel (68.8 mg, 92%). $^1$H NMR (400 MHz, CD$_3$OD) δ 7.26 (dd, J=8.5, 3.4 Hz, 2H), 6.84 (dd, J=8.7, 5.0 Hz, 2H), 6.24 (d, J=16.3 Hz, 1H), 6.06 (dd, J=16.3, 2.1 Hz, 1H), 5.88 (dd, J=17.5, 10.8 Hz, 1H), 5.12-5.06 (m, 1H), 5.03-4.95 (m, 2H), 4.07-3.39 (m, 10H), 3.15-2.60 (m, 14H), 1.97-1.89 (m, 2H), 1.80-1.60 (m, 7H), 1.55 (s, 3H), 1.48-1.42 (m, 2H), 1.17 (s, 3H). $^{13}$C NMR (100 MHz, CD$_3$OD) δ 159.55, 147.27, 136.70, 136.60, 132.00, 128.25, 128.20, 127.91, 127.87, 125.91, 115.52, 112.31, 68.66, 52.22, 51.95, 51.22, 48.04, 47.79, 46.85, 46.72, 46.22, 45.54, 45.09, 44.88, 43.55, 42.53, 28.23, 25.90, 24.34, 23.83, 22.49, 17.69. HRMS (ESI+): calculated for C$_{32}$H$_{55}$N$_5$O [M+H]$^+$ 526.4485, found 526.4476.

Preparation of Compound 32

Compound 5 (31.7 mg, 0.089 mmol) was dissolved in methanol (8 mL). Then, iodomethane (1 mL) was added. The reaction mixture was stirred at room temperature overnight. After the reaction, the reaction mixture was diluted with n-butanol and extracted twice with water. The organic phase was concentrated under reduced pressure. The crude product was purified by RP-HPLC, to afford compound 32 as a yellow gel (31.6 mg, 72%). $^1$H NMR (400 MHz, CD$_3$OD) δ 7.29 (d, J=8.7 Hz, 2H), 6.87 (d, J=8.7 Hz, 2H), 6.27 (d, J=16.3 Hz, 1H), 6.08 (d, J=16.3 Hz, 1H), 5.90 (dd, J=17.5, 10.8 Hz, 1H), 5.15-5.09 (m, 1H), 5.06-4.97 (m, 2H), 4.06 (t, J=5.9 Hz, 2H), 3.46-3.38 (m, 2H), 3.14 (s, 9H), 2.04-1.82 (m, 6H), 1.66 (s, 3H), 1.57 (s, 3H), 1.51-1.45 (m, 2H), 1.19 (s, 3H). $^{13}$C NMR (100 MHz, CD$_3$OD) δ 159.38, 147.29, 136.72, 132.23, 131.99, 128.21 (2×CH), 127.90, 125.94, 115.56 (2×CH), 112.30, 67.93, 67.54, 53.54, 53.50, 53.46, 43.55, 42.54, 27.17, 25.88, 24.35, 23.84, 21.10, 17.67·HRMS (ESI+): calculated for C$_{25}$H$_{40}$INO [M-I]$^+$ 370.3104, found 370.3105.

Preparation of Compound 33

According to the method for synthesis of compound 32, compound 6 (31.3 mg, 0.082 mmol) and iodomethane (1 mL) used as starting materials were prepared into compound 33 as a yellow gel (34.7 mg, 83%). $^1$H NMR (400 MHz, CD$_3$OD) δ 7.29 (d, J=8.7 Hz, 2H), 6.88 (d, J=8.8 Hz, 2H), 6.27 (d, J=16.3 Hz, 1H), 6.09 (d, J=16.3 Hz, 1H), 5.90 (dd, J=17.5, 10.8 Hz, 1H), 5.15-5.08 (m, 1H), 5.06-4.98 (m, 2H), 4.06 (t, J=5.7 Hz, 2H), 3.41-3.31 (m, 6H), 3.00 (s, 3H), 1.99-1.83 (m, 6H), 1.66 (s, 3H), 1.57 (s, 3H), 1.51-1.45 (m, 2H), 1.36-1.31 (m, 6H), 1.19 (s, 3H). $^{13}$C NMR (100 MHz, CD$_3$OD) δ 159.34, 147.29, 136.76, 132.28, 131.99, 128.22 (2×CH), 127.89, 125.94, 115.56 (2×CH), 112.30, 67.89, 61.22, 57.61, 57.58, 57.54, 43.55, 42.54, 27.08, 25.88, 24.35, 23.85, 20.16, 17.67, 9.12, 8.01. HRMS (ESI+): calculated for C$_{27}$H$_{44}$INO [M-I]$^+$ 398.3417, found 398.3418.

Preparation of Compound 34

According to the method for synthesis of compound 32, compound 7 (34.5 mg, 0.078 mmol) and iodomethane (1 mL) used as starting materials were prepared into compound 34 as a yellow oil (37 mg, 81%). $^1$H NMR (400 MHz, CD$_3$OD) δ 7.27 (d, J=8.8 Hz, 2H), 6.85 (d, J=8.8 Hz, 2H), 6.24 (d, J=16.3 Hz, 1H), 6.06 (d, J=16.3 Hz, 1H), 5.88 (dd, J=17.5, 10.8 Hz, 1H), 5.13-5.06 (m, 1H), 5.03-4.95 (m, 2H), 4.04 (t, J=5.7 Hz, 2H), 3.36-3.30 (m, 2H), 3.28-3.21 (m, 4H), 3.00 (s, 3H), 1.98-1.78 (m, 6H), 1.73-1.61 (m, 7H), 1.54 (s, 3H), 1.49-1.34 (m, 6H), 1.18-1.15 (m, 3H), 0.97 (t, J=7.4 Hz, 6H). $^{13}$C NMR (100 MHz, CD$_3$OD) δ 159.30, 147.28, 136.76, 132.29, 131.98, 128.24 (2×CH), 127.88, 125.94, 115.56 (2×CH), 112.30, 67.71, 62.71, 62.68, 62.65, 62.07, 43.55, 42.54, 26.96, 25.89, 25.12 (2×CH$_2$), 24.35, 23.86, 20.74, 20.72, 20.14, 17.68, 13.93 (2×CH$_3$). HRMS (ESI+): calculated for C$_{31}$H$_{52}$INO [M-I]$^+$454.4043, found 454.4043.

Preparation of Compound 35

According to the method for synthesis of compound 38, 13 (45.6 mg, 0.139 mmol), 1H-pyrazole-1-carboxamidine hydrochloride (61.2 mg, 0.418 mmol) and DIPEA (138 µL, 0.835 mmol) used as starting materials were prepared into compound 35 as a yellow gel (30.6 mg, 55%). $^1$H NMR (400 MHz, CD$_3$OD) δ 7.28 (d, J=8.6 Hz, 2H), 6.85 (d, J=8.8 Hz, 2H), 6.26 (d, J=16.3 Hz, 1H), 6.07 (d, J=16.3 Hz, 1H), 5.90 (dd, J=17.5, 10.8 Hz, 1H), 5.16-5.09 (m, 1H), 5.05-4.98 (m, 2H), 4.00 (t, J=5.9 Hz, 2H), 3.25 (t, J=6.9 Hz, 2H), 2.00-1.92 (m, 2H), 1.88-1.74 (m, 4H), 1.66 (s, 3H), 1.57 (s, 3H), 1.50-1.45 (m, 2H), 1.19 (s, 3H). $^{13}$C NMR (100 MHz, CD$_3$OD) δ 159.54, 158.70, 147.28, 136.55, 132.03, 131.97, 128.15 (2×CH), 127.94, 125.92, 115.51 (2×CH), 112.28, 68.36, 43.53, 42.53, 42.17, 27.46, 26.76, 25.88, 24.33, 23.84, 17.67. HRMS (ESI+): calculated for C$_{23}$H$_{35}$N$_3$O [M+H]$^+$ 370.2858, found 370.2849.

Preparation of Compound 36

Bakuchiol (93.5 mg, 0.357 mmol) was dissolved in acetone (10 mL). Then, potassium carbonate (123.5 mg, 0.893 mmol) and ethyl bromoacetate (81 µL, 0.081 mmol) were added. The reaction mixture was stirred under reflux for 3 h. After the reaction, the resulting mixture was diluted with ethyl acetate and extracted twice with water. The organic phase was concentrated under reduced pressure. The crude product was purified by silica gel column chromatography (petroleum ether/ethyl acetate, 6:1, v/v), to afford compound 36 as a pale yellow oil (114.1 mg, 93%). $^1$H NMR (400 MHz, CDCl$_3$) δ 7.29 (d, J=8.7 Hz, 2H), 6.85 (d, J=8.8 Hz, 2H), 6.26 (d, J=16.3 Hz, 1H), 6.08 (d, J=16.3 Hz, 1H), 5.88 (dd, J=17.4, 10.7 Hz, 1H), 5.14-5.07 (m, 1H), 5.06-4.98 (m, 2H), 4.61 (s, 2H), 4.27 (q, J=7.1 Hz, 2H), 1.99-1.91 (m, 2H), 1.67 (s, 3H), 1.58 (s, 3H), 1.52-1.47 (m, 2H), 1.30 (t, J=7.1 Hz, 3H), 1.19 (s, 3H). $^{13}$C NMR (100 MHz, CDCl$_3$) δ 169.03, 157.02, 145.96, 136.51, 131.85, 131.40, 127.31 (2×CH), 126.43, 124.86, 114.80 (2×CH), 112.02, 65.64, 61.46, 42.64, 41.35, 25.78, 23.42, 23.31, 17.72, 14.25. HRMS (ESI+): calculated for C$_{22}$H$_{30}$O$_3$[M+H]$^+$ 343.2273, found 343.2265.

Preparation of Compound 38

Compound 36 (121.8 mg, 0.356 mmol) was dissolved in tetrahydrofuran (10 mL). Then, a solution of LiGH (34.1 mg, 1.42 mmol) in water (5 mL) was added. The reaction mixture was stirred at room temperature for 0.5 hour. Then, the resulting mixture was acidified with acetic acid and extracted twice with n-butanol and water. The combined organic phase was concentrated under reduced pressure, to afford a crude product 37. Compound 37 was directly used in the next reaction without further purification. Compound 37 was dissolved in anhydrous DMF (8 mL). Then, HATU (405.6 mg, 1.07 mmol), H-Arg-OMe·2HCl (278.6 mg, 1.07 mmol), HOBt (144.1 mg, 1.07 mmol), EDC·HCl (204.5 mg, 1.07 mmol) and DIPEA (470.1 µL, 2.84 mmol) were added. The reaction mixture was stirred at room temperature for 48 hours. After the reaction, the reaction mixture was extracted twice with n-butanol and water. The organic phase was concentrated under reduced pressure. The resulting crude product was purified by RP-HPLC, to afford compound 38 as a yellow gel (122.4 mg, 71%). $^1$H NMR (400 MHz, CDCl$_3$) δ 8.15 (s, 1H), 7.59 (d, J=8.0 Hz, 1H), 7.29 (d, J=8.7 Hz, 2H), 7.07 (br, 3H), 6.86 (d, J=8.7 Hz, 2H), 6.24 (d, J=16.2 Hz, 1H), 6.07 (d, J=16.2 Hz, 1H), 5.86 (dd, J=17.5, 10.7 Hz, 1H), 5.09 (t, J=7.1 Hz, 1H), 5.06-4.96 (m, 2H), 4.64-4.42 (m, 3H), 3.72 (s, 3H), 3.20 (d, J=55.2 Hz, 2H), 2.01-1.91 (m, 6H), 1.66 (s, 3H), 1.57 (s, 3H), 1.51-1.45 (m, 2H), 1.18 (s, 3H). $^{13}$C NMR (100 MHz, CD$_3$OD) δ 173.31, 171.43, 158.65, 158.29, 147.19, 137.37, 133.23, 132.02, 128.28 (2×CH), 127.71, 125.90, 115.96 (2×CH), 112.37, 68.17, 52.94, 52.84, 43.59, 42.51, 41.77, 29.49, 26.23, 25.88, 24.34, 23.79, 17.67. HRMS (ESI+): calculated for C$_{27}$H$_{40}$N$_4$O$_4$ [M+H]$^+$ 485.3128, found 485.3125.

Preparation of Compound 39

According to the method for synthesis of compound 38, 36 (40.9 mg, 0.119 mmol), HATU (136 mg, 0.358 mmol), H-Arg-NH$_2$·2HCl (93.9 mg, 0.358 mmol), HOBt (48.2 mg, 0.358 mmol), EDC·HCl (68.4 mg, 0.358 mmol) and DIPEA (157.9 µL, 0.955 mmol) used as starting materials were prepared into compound 39 as a yellow gel (30.6 mg, 55%). $^1$H NMR (400 MHz, CD$_3$OD) δ 7.33 (d, J=8.7 Hz, 2H), 6.94 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.16-5.08 (m, 1H), 5.06-4.98 (m, 2H), 4.60-4.56 (m, 2H), 4.52-4.48 (m, 1H), 3.21-3.14 (m, 2H), 1.99-1.72 (m, 4H), 1.66 (s, 3H), 1.63-1.55 (m, 5H), 1.51-1.45 (m, 2H), 1.20 (s, 3H). $^{13}$C NMR (100 MHz, CD$_3$OD) δ 171.14, 158.63, 158.20, 147.19, 137.43, 133.29, 132.03, 128.33 (2×CH), 127.70, 125.91, 115.93, 112.38, 101.33, 68.22, 53.31, 43.60, 42.51, 41.88, 30.52, 26.13, 25.87, 24.34, 23.80, 17.67. HRMS (ESI+): calculated for C$_{26}$H$_{39}$N$_5$O$_3$ [M+H]$^+$ 470.3131, found 470.3127.

Preparation of Compound 40

According to the method for synthesis of compound 38, 36 (99.6 mg, 0.291 mmol), HATU (221.2 mg, 0.582 mmol), H-His-OMe·2HCl (140.8 mg, 0.582 mmol), HOBt (78.4 mg, 0.582 mmol), EDC·HCl (111.2 mg, 0.582 mmol) and DIPEA (288 µL, 1.74 mmol) used as starting materials were prepared into compound 40 as a yellow gel (87.4 mg, 64%). $^1$H NMR (400 MHz, CD$_3$OD) δ 7.94 (s, 1H), 7.31 (d, J=8.7 Hz, 2H), 6.98-6.84 (m, 3H), 6.28 (d, J=16.3 Hz, 1H), 6.12 (d, J=16.3 Hz, 1H), 5.91 (dd, J=17.5, 10.8 Hz, 1H), 5.15-5.08 (m, 1H), 5.07-4.98 (m, 2H), 4.83-4.79 (m, 1H), 4.54-4.46 (m, 2H), 3.72 (s, 3H), 3.26-3.09 (m, 2H), 2.00-1.92 (m, 2H), 1.66 (s, 3H), 1.57 (s, 3H), 1.51-1.46 (m, 2H), 1.20 (s, 3H). $^{13}$C NMR (100 MHz, CD$_3$OD) δ 171.02, 169.03, 156.31, 145.80, 136.84, 134.51, 132.11, 131.46, 130.82, 127.41 (2×CH), 126.20, 124.78, 116.80, 114.87 (2×CH), 112.14, 67.23, 52.96, 51.77, 42.66, 41.28, 28.11, 25.83, 23.28, 23.24, 17.76. HRMS ((ESI+): calculated for C$_{27}$H$_{35}$N$_3$O$_4$ [M+H]$^+$ 466.2706, found 466.2698.

Preparation of Compound 41

According to the method for synthesis of compound 38, 36 (50 mg, 0.146 mmol), HATU (111 mg, 0.292 mmol), H-Lys(Boc)-OMe HCl (108.3 mg, 0.365 mmol), HOBt (39.3 mg, 0.292 mmol), EDC·HCl (55.8 mg, 0.292 mmol) and DIPEA (144.8 µL, 0.876 mmol) used as starting materials were prepared into compound 41 as a yellow gel (72.5 mg, 82%). $^1$H NMR (400 MHz, CDCl$_3$) δ 7.30 (d, J=8.8 Hz, 2H), 7.04 (d, J=8.3 Hz, 1H), 6.87 (d, J=8.8 Hz, 2H), 6.25 (d, J=16.3 Hz, 1H), 6.08 (d, J=16.2 Hz, 1H), 5.86 (dd, J=17.5, 10.7 Hz, 1H), 5.13-4.94 (m, 3H), 4.72-4.60 (m, 1H), 4.57-4.44 (m, 3H), 3.73 (s, 3H), 3.10-2.98 (m, 2H), 1.96-1.71 (m, 4H), 1.65 (s, 3H), 1.56 (s, 3H), 1.50-1.43 (m, 4H), 1.41 (s, 9H), 1.31-1.23 (m, 2H), 1.18 (s, 3H). HRMS (ESI+): calculated for C$_{32}$H$_{48}$N$_2$O$_6$ [M+Na]$^+$ 579.3410, found 579.3398.

Preparation of Compound 42

According to the method for synthesis of compound 44, 36 (48 mg, 0.14 mmol), HATU (133.9 mg, 0.352 mmol), H-Ala-OMe HCl (59 mg, 0.423 mmol) and DIPEA (186 μL, 1.13 mmol) used as starting materials were prepared into a crude product which is compound 42. After the reaction, the resulting mixture was diluted with ethyl acetate and extracted twice with water. The organic phase was concentrated under reduced pressure. The crude product was purified by silica gel column chromatography (petroleum ether/ethyl acetate, 2:1, v/v), to afford compound 42 as a colorless clear gel (45.2 mg, 81%). $^1$H NMR (400 MHz, CDCl$_3$) δ 7.32 (d, J=8.8 Hz, 2H), 7.13 (d, J=7.6 Hz, 1H), 6.88 (d, J=8.8 Hz, 2H), 6.26 (d, J=16.3 Hz, 1H), 6.09 (d, J=16.3 Hz, 1H), 5.87 (dd, J=17.4, 10.7 Hz, 1H), 5.15-5.07 (m, 1H), 5.06-4.96 (m, 2H), 4.76-4.63 (m, 1H), 4.49 (s, 2H), 3.76 (s, 3H), 1.99-1.90 (m, 2H), 1.67 (s, 3H), 1.58 (s, 3H), 1.51-1.45 (m, 5H), 1.19 (s, 3H). $^{13}$C NMR (100 MHz, CDCl$_3$) δ 173.07, 167.93, 156.28, 145.85, 136.84, 132.22, 131.47, 127.47 (2×CH), 126.26, 124.81, 114.87 (2×CH), 112.12, 67.41, 52.71, 47.70, 42.68, 41.32, 25.82, 23.33, 23.30, 18.48, 17.75. HRMS (ESI+): calculated for $C_{24}H_{33}NO_4$ [M+H]$^+$ 400.2488, found 400.2471.

Preparation of Compound 43

According to the method for synthesis of compound 44, 36 (79.5 mg, 0.232 mmol), HATU (176.5 mg, 0.464 mmol), H-Lys(Fmoc)-OH·HCl (243.1 mg, 0.58 mmol) and DIPEA (230 μL, 1.39 mmol) used as starting materials were prepared into compound 43 as a colorless clear gel (155.5 mg, 98%). HRMS (ESI+): calculated for $C_{42}H_{50}N_2O_6$[M+H]$^+$ 679.3747, found 679.3727.

Preparation of Compound 44

According to the method for synthesis of compound 38, 36 (89.3 mg, 0.261 mmol), HATU (198.3 mg, 0.522 mmol), H-Arg-Arg-OMe·2HCl (217.7 mg, 0.522 mmol) and DIPEA (174 μL, 1.04 mmol) used as starting materials were prepared into compound 44 as a while colloidal solid (166 mg, 98%). $^1$H NMR (400 MHz, CD$_3$OD) δ 7.33 (d, J=8.8 Hz, 2H), 6.93 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.07-4.98 (m, 2H), 4.58 (s, 2H), 4.52-4.44 (m, 2H), 3.73 (s, 3H), 3.25-3.12 (m, 4H), 2.01-1.86 (m, 4H), 1.83-1.62 (m, 9H), 1.57 (s, 3H), 1.52-1.45 (m, 2H), 1.20 (s, 3H). $^{13}$C NMR (100 MHz, CD$_3$OD) δ 173.80, 173.51, 171.21, 158.69, 158.24 (2×C), 147.19, 137.46, 133.28, 132.05, 128.33 (2×CH), 127.68, 125.90, 115.91 (2×CH), 112.39, 68.08, 53.94, 53.17, 52.90, 43.60, 42.51, 41.93, 41.78, 30.28, 29.49, 26.17, 26.08, 25.87, 24.34, 23.79, 17.67. HRMS (ESI+): calculated for $C_{33}H_{52}N_8O_5$ [M+H]$^+$ 641.4139, found 641.4130.

Preparation of Compound 45

According to the method for synthesis of compound 44, 36 (54.7 mg, 0.160 mmol), HATU (121.7 mg, 0.32 mmol), H-Arg-Arg-Arg-OMe·2HCl (160.2 mg, 0.32 mmol) and DIPEA (158.4 μL, 0.96 mmol) used as starting materials were prepared into compound 45 as a white gel (118.5 mg, 93%). $^1$H NMR (400 MHz, CD$_3$OD) δ 7.33 (d, J=8.8 Hz, 2H), 6.93 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.06-4.98 (m, 2H), 4.59 (s, 2H), 4.49-4.36 (m, 3H), 3.72 (s, 3H), 3.22-3.16 (m, 6H), 1.98-1.63 (m, 17H), 1.57 (s, 3H), 1.52-1.45 (m, 2H), 1.20 (s, 3H). $^{13}$C NMR (100 MHz, CD$_3$OD) δ 174.00, 173.78, 173.58, 171.42, 158.65, 158.22 (3×C), 147.16, 137.41, 133.20, 132.03, 128.33, 127.66, 125.88, 115.86 (2×CH), 112.40, 101.32, 68.02, 54.23, 54.12, 53.30, 52.87, 43.59, 42.49, 41.90, 41.85, 41.80, 30.11, 30.06, 29.41, 26.21, 26.15, 26.11, 25.88, 24.33, 23.75, 17.67. HRMS (ESI+): calculated for $C_{39}H_{64}N_{12}O_6$ [M+H]$^+$ 797.5150, found 797.5121.

Preparation of Compound 46

According to the method for synthesis of compound 42, 36 (48 mg, 0.14 mmol), HATU (160.7 mg, 0.423 mmol), H-Met-OMe HCl (84.4 mg, 0.423 mmol) and DIPEA (186 μL, 1.13 mmol) used as starting materials were prepared into compound 46 as a colorless clear gel (50.4 mg, 78%). $^1$H NMR (400 MHz, CDCl$_3$) δ 7.30 (d, J=8.8 Hz, 2H), 7.23 (d, J=8.2 Hz, 1H), 6.86 (d, J=8.8 Hz, 2H), 6.25 (d, J=16.3 Hz, 1H), 6.08 (d, J=16.2 Hz, 1H), 5.86 (dd, J=17.5, 10.7 Hz, 1H), 5.13-5.05 (m, 1H), 5.04-4.97 (m, 2H), 4.84-4.74 (m, 1H), 4.50 (s, 2H), 3.75 (s, 3H), 2.53-2.43 (m, 2H), 2.25-1.89 (m, 7H), 1.66 (s, 3H), 1.56 (s, 3H), 1.51-1.45 (m, 2H), 1.18 (s, 3H). $^{13}$C NMR (100 MHz, CDCl$_3$) δ 172.01, 168.32, 156.23, 145.84, 136.89, 132.28, 131.47, 127.49 (2×CH), 126.23, 124.80, 114.83 (2×CH), 112.13, 67.39, 52.78, 51.12, 42.68, 41.32, 31.54, 29.95, 25.82, 23.33, 23.30, 17.75, 15.54. HRMS (ESI+): calculated for $C_{26}H_{37}NO_4S$ [M+H]$^+$ 460.2522, found 460.2507.

Preparation of Compound 47

43 (76 mg, 0.112 mmol) was dissolved in anhydrous DMF (4 mL). Then, piperidine (1 mL) was added. The reaction mixture was stirred at room temperature for 0.5 h. After the reaction, the resulting mixture was diluted with n-butanol and extracted twice with water. The organic phase was concentrated under reduced pressure. The crude product was purified by RP-HPLC, to afford compound 47 as a yellow gel (38.2 mg, 75%). $^1$H NMR (400 MHz, CDCl$_3$) δ 7.32 (dd, J=19.6, 8.5 Hz, 3H), 6.86 (d, J=8.7 Hz, 2H), 6.24 (d, J=16.2 Hz, 1H), 6.08 (d, J=16.2 Hz, 1H), 5.86 (dd, J=17.4, 10.8 Hz, 1H), 5.09 (t, J=7.1 Hz, 1H), 5.06-4.97 (m, 2H), 4.70-4.59 (m, 1H), 4.57-4.40 (m, 2H), 3.77-3.67 (m, 3H), 2.88 (s, 2H), 1.98-1.62 (m, 9H), 1.57 (s, 3H), 1.52-1.34 (m, 4H), 1.18 (s, 3H). $^{13}$C NMR (100 MHz, CDCl$_3$) δ 172.28, 168.63, 156.25, 145.82, 136.86, 132.22, 131.46, 127.46 (2×CH), 126.23, 124.79, 114.94 (2×CH), 112.13, 67.32, 52.76, 51.48, 42.67, 41.30, 39.19, 31.97, 27.08, 25.83 (2×CH$_2$), 23.29, 22.46, 17.76. HRMS (ESI+): calculated for $C_{27}H_{40}N_2O_4$ [M+H]$^+$ 457.3066, found 457.3050.

Preparation of Compound 49

According to the method for synthesis of compound 38, 38 (43.2 mg, 0.092 mmol), HATU (69.9 mg, 0.184 mmol), H-Arg-NH$_2$·2HCl (45.2 mg, 0.184 mmol), HOBt (24.8 mg, 0.184 mmol), EDC·HCl (35.2 mg, 0.184 mmol) and DIPEA (91.9 μL, 0.551 mmol) used as starting materials were prepared into compound 49 as a yellow gel (26.6 mg, 47%). $^1$H NMR (400 MHz, CD$_3$OD) δ 7.33 (d, J=8.8 Hz, 2H), 6.93 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.06-4.99 (m, 2H), 4.58 (s, 2H), 4.50-4.45 (m, 1H), 4.42-4.36 (m, 1H), 3.21-3.15 (m, 4H), 2.01-1.74 (m, 6H), 1.69-1.61 (m, 7H), 1.57 (s, 3H), 1.52-1.45 (m, 2H), 1.20 (s, 3H). $^{13}$C NMR (100 MHz, CD$_3$OD) δ 176.28, 173.66, 171.35, 158.70, 158.25 (2×C), 147.18, 137.44, 133.25, 132.04, 128.33 (2×CH), 127.68, 125.90, 115.92 (2×CH), 112.39, 68.11, 54.06, 53.89, 43.60, 42.51, 41.88, 41.86, 30.36, 30.10, 26.23, 26.03, 25.87, 24.34, 23.80, 17.67. HRMS (ESI+): calculated for $C_{32}H_{51}N_9O_4$ [M+H]$^+$ 626.4142, found 626.4135.

Preparation of Compound 50

According to the method for synthesis of compound 49, 38 (93 mg, 0.192 mmol), HATU (218.9 mg, 0.576 mmol), H-His-OMe·2HCl (139.4 mg, 0.576 mmol), HOBt (77.6 mg, 0.576 mmol), EDC·HCl (110.1 mg, 0.576 mmol) and DIPEA (190.3 µL, 1.15 mmol) used as starting materials were prepared into compound 50 as a yellow gel (60.6 mg, 51%). $^1$H NMR (400 MHz, CD$_3$OD) δ 7.72 (s, 1H), 7.33 (d, J=8.8 Hz, 2H), 6.93 (d, J=8.7 Hz, 3H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.06-4.99 (m, 2H), 4.73-4.67 (m, 1H), 4.56 (s, 2H), 4.53-4.48 (m, 1H), 3.71 (s, 3H), 3.20-3.02 (m, 4H), 2.01-1.70 (m, 4H), 1.66 (s, 3H), 1.63-1.56 (m, 5H), 1.51-1.46 (m, 2H), 1.20 (s, 3H). $^{13}$C NMR (100 MHz, CD$_3$OD) δ 173.51, 172.65, 171.12, 168.75, 158.60, 158.20, 158.17, 147.16, 137.36, 135.88, 133.19, 133.01, 132.04, 128.33, 127.66, 125.88, 118.33, 115.88, 112.40, 68.06, 53.68, 53.02, 43.60, 42.49, 41.83, 38.88, 30.22, 28.99, 26.02, 25.90, 24.33, 23.73, 17.68. HRMS (ESI+): calculated for $C_{33}H_{47}N_7O_5$ [M+H]$^+$ 622.3717, found 622.3692.

Preparation of Compounds 65 and 51

Compound 38 (63.7 mg, 0.131 mmol) was dissolved in anhydrous DMF (8 mL). Then, HATU (124.9 mg, 0.329 mmol), H-Lys(Fmoc)-OH·HCl (137.7 mg, 0.329 mmol) and DIPEA (130 µL, 0.789 mmol) were added. According to the method for synthesis of compound 43, compound 65 was prepared. After the reaction, the reaction mixture was extracted twice with n-butanol and water. The organic phase was concentrated under reduced pressure. Compound 65 was used in the next reaction without further purification. Subsequently, the crude product 65 was dissolved in anhydrous DMF (4 mL). Piperidine (1 mL) was added. According to the method for synthesis of 47, 51 was prepared as an orange gel (44.5 mg, 55%). $^1$H NMR (400 MHz, CD$_3$OD) δ 7.33 (d, J=8.8 Hz, 2H), 6.93 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.14-5.09 (m, 1H), 5.07-5.00 (m, 2H), 4.58 (s, 2H), 4.50-4.42 (m, 2H), 3.72 (s, 3H), 3.25-3.17 (m, 2H), 2.92-2.82 (m, 2H), 2.01-1.89 (m, 4H), 1.78-1.62 (m, 9H), 1.57 (s, 3H), 1.52-1.45 (m, 4H), 1.20 (s, 3H). $^{13}$C NMR (100 MHz, CD$_3$OD) δ 173.89, 173.75, 171.25, 158.66, 158.24 (2×C), 147.17, 137.38, 133.18, 132.04, 128.34 (2×CH), 127.66, 125.88, 115.87 (2×CH), 112.40, 67.97, 54.04, 53.17, 52.86, 43.60, 42.50, 41.87, 40.40, 31.67, 30.19, 27.78, 26.08, 25.90, 24.34, 23.73, 23.69, 17.68. HRMS (ESI+): calculated for $C_{33}H_{52}N_6O_5$ [M+H]$^+$ 613.4077, found 613.4056.

Preparation of Compound 52

According to the method for synthesis of compound 38, 38 (40 mg, 0.083 mmol), HATU (62.8 mg, 0.165 mmol), N,N-diethyl-1,3-propanediamine (78.1 µL, 0.495 mmol) and DIPEA (68.2 µL, 0.413 mmol) used as starting materials were prepared into compound 52 as a yellow gel (43.2 mg, 89%). $^1$H NMR (400 MHz, CDCl$_3$) δ 7.29 (d, J=8.5 Hz, 2H), 6.90 (d, J=8.4 Hz, 2H), 6.25 (d, J=16.3 Hz, 1H), 6.09 (d, J=16.3 Hz, 1H), 5.87 (dd, J=17.5, 10.8 Hz, 1H), 5.08 (t, J=7.2 Hz, 1H), 5.02-4.95 (m, 2H), 4.56 (s, 2H), 4.32-4.26 (m, 1H), 3.28-3.26 (m, 2H), 3.17-3.02 (m, 8H), 1.97-1.69 (m, 6H), 1.68-1.55 (m, 5H), 1.54 (s, 3H), 1.48-1.42 (m, 2H), 1.23 (t, J=7.3 Hz, 6H), 1.16 (s, 3H). $^{13}$C NMR (100 MHz, CDCl$_3$) δ 172.59 (2×C), 156.81, 156.48, 145.79, 136.69, 131.87, 131.42, 127.40, 126.23, 124.78, 114.94, 114.91, 112.10, 100.00, 60.53, 58.51, 58.44, 50.85 (2×CH$_2$), 46.34, 42.63 (2×CH$_2$), 41.27, 25.81 (2×CH$_2$), 23.28, 23.21, 21.18, 17.75, 14.29, 8.43 (2×CH$_3$). HRMS (ESI+): calculated for $C_{33}H_{54}N_6O_3$ [M+H]$^+$ 583.4336, found 583.4327.

Preparation of Compound 53

According to the method for synthesis of compound 38, 38 (48 mg, 0.101 mmol), HATU (115.3 mg, 0.303 mmol), (S)—N-((3-(3-fluoro-4-piperazin-1-ylphenyl)-2-oxooxazolidin-5-yl)methyl)-acetamide (85.0 mg, 0.253 mmol), HOBt (46.4 mg, 0.303 mmol), EDC·HCl (58.3 mg, 0.303 mmol) and DIPEA (133.7 µL, 0.809 mmol) used as starting materials were prepared into compound 53 as a yellow gel (32.4 mg, 41%). $^1$H NMR (400 MHz, CD$_3$OD) δ 7.50 (dd, J=14.5, 2.5 Hz, 1H), 7.32 (d, J=8.7 Hz, 2H), 7.17 (d, J=8.7 Hz, 1H), 7.03 (t, J=9.1 Hz, 1H), 6.94 (d, J=8.8 Hz, 2H), 6.27 (d, J=16.3 Hz, 1H), 6.11 (d, J=16.3 Hz, 1H), 5.89 (dd, J=17.5, 10.8 Hz, 1H), 5.14-5.09 (m, 1H), 5.05-4.97 (m, 3H), 4.83-4.74 (m, 2H), 4.61-4.56 (m, 2H), 4.11 (t, J=9.0 Hz, 1H), 3.92-3.75 (m, 3H), 3.73-3.61 (m, 2H), 3.55 (d, J=5.0 Hz, 2H), 3.28-3.14 (m, 2H), 3.10-2.93 (m, 4H), 1.99-1.74 (m, 7H), 1.67-1.60 (m, 5H), 1.57 (s, 3H), 1.50-1.45 (m, 2H), 1.19 (s, 3H). $^{13}$C NMR (100 MHz, CD$_3$OD) δ 174.06, 171.20, 170.77, 158.61, 158.17, 158.03, 156.56, 155.59, 147.17, 137.45, 137.00, 135.38, 133.30, 132.03, 128.35, 127.66, 125.90, 120.85, 115.97, 115.49, 112.40, 108.55, 108.29, 73.46, 68.16, 49.85, 48.34 (2×CH$_2$), 46.95, 43.59 (2×CH$_2$), 43.52, 43.14, 42.49, 41.96, 30.28, 25.89 (2×CH$_3$), 24.34, 23.78, 22.46, 17.69.

Preparation of Compound 55

According to the method for synthesis of compound 40, 40 (66.4 mg, 0.143 mmol), HATU (108.5 mg, 0.285 mmol), H-His-OMe·2HCl (86.3 mg, 0.357 mmol), HOBt (38.4 mg, 0.285 mmol), EDC·HCl (54.5 mg, 0.285 mmol) and DIPEA (141.4 µL, 0.856 mmol) used as starting materials were prepared into compound 55 as a yellow gel (41.2 mg, 48%). $^1$H NMR (400 MHz, CD$_3$OD) δ 8.28 (d, J=9.4 Hz, 2H), 8.11 (d, J=40.2 Hz, 2H), 7.28 (d, J=8.8 Hz, 2H), 7.07 (d, J=25.4 Hz, 2H), 6.85 (d, J=8.7 Hz, 2H), 6.17 (dd, J=64.9, 16.3 Hz, 2H), 5.88 (dd, J=17.5, 10.8 Hz, 1H), 5.12-4.94 (m, 4H), 4.74-4.64 (m, 2H), 4.55-4.41 (m, 2H), 3.70 (s, 3H), 3.19-3.06 (m, 2H), 2.78 (s, 2H), 1.98-1.89 (m, 2H), 1.63 (s, 3H), 1.54 (s, 3H), 1.49-1.41 (m, 2H), 1.17 (s, 3H). $^{13}$C NMR (100 MHz, CD$_3$OD) δ 172.47, 172.35, 171.08, 158.18, 147.18, 137.45, 135.76, 135.63, 133.24, 132.74, 132.03, 132.00, 128.31, 127.68, 125.90, 118.32, 118.16, 115.90, 115.87, 112.38, 97.37, 68.14, 53.66, 53.09, 43.60, 42.50, 38.88, 29.25, 28.52, 25.87, 24.34, 23.78, 17.67. HRMS (ESI+): calculated for $C_{33}H_{42}N_6O_5$ [M+H]$^+$ 603.3295, found 603.3278.

Preparation of Compounds 66 and 56

According to the method for synthesis of compound 51, 40 (89.9 mg, 0.193 mmol), HATU (220.1 mg, 0.597 mmol), H-Lys(Fmoc)-OH·HCl (242.7 mg, 0.597 mmol) and DIPEA (255 µL, 1.54 mmol) used as starting materials were prepared into compound 56 as a yellow gel (39.5 mg, 35%). $^1$H NMR (400 MHz, CD$_3$OD) δ 7.82 (s, 1H), 7.31 (d, J=8.7 Hz, 2H), 6.98 (s, 1H), 6.88 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.08-5.02 (m, 2H), 4.70-4.63 (m, 1H), 4.55-4.43 (m, 3H), 3.74-3.69 (m, 3H), 3.19-3.03 (m, 2H), 2.91-2.83 (m, 2H), 1.98-1.92 (m, 2H), 1.77-1.55 (m, 10H), 1.52-1.42 (m, 4H), 1.20 (s, 3H). $^{13}$C NMR (100 MHz, CD$_3$OD) δ 173.64, 173.24, 171.21, 158.21, 147.17, 137.35, 136.19, 133.14, 132.04, 128.31 (2×CH), 127.69, 125.88, 117.97, 115.86 (2×CH), 112.40, 101.32, 67.99, 54.49, 53.11, 52.86, 43.60, 42.50, 40.41, 31.79, 29.93, 27.77, 25.90, 24.34, 23.74, 23.57, 17.69. HRMS ((ESI+): calculated for C$_{33}$H$_{47}$N$_5$O$_5$ [M+H]$^+$ 594.3655, found 594.3637.

Preparation of Compound 58

According to the method for synthesis of compound 38, 44 (74.7 mg, 0.119 mmol), HATU (135.9 mg, 0.358 mmol), H-Arg-NH$_2$·2HCl (93.7 mg, 0.358 mmol), HOBt (47.6 mg, 0.358 mmol), EDC·HCl (68.5 mg, 0.358 mmol) and DIPEA (157.6 μL, 0.953 mmol) used as starting materials were prepared into compound 58 as a yellow gel (66.6 mg, 70%). $^1$H NMR (400 MHz, CD$_3$OD) δ 7.33 (d, J=8.7 Hz, 2H), 6.93 (d, J=8.7 Hz, 2H), 6.28 (d, J=16.3 Hz, 1H), 6.12 (d, J=16.3 Hz, 1H), 5.91 (dd, J=17.4, 10.8 Hz, 1H), 5.12 (t, J=7.2 Hz, 1H), 5.07-4.92 (m, 3H), 4.59 (s, 2H), 4.49-4.32 (m, 3H), 3.22-3.15 (m, 6H), 2.00-1.73 (m, 8H), 1.66 (s, 9H), 1.57 (s, 3H), 1.51-1.46 (m, 2H), 1.20 (s, 3H). $^{13}$C NMR (100 MHz, CD$_3$OD) δ 176.33, 173.84, 171.47, 169.92, 158.69, 158.24 (3×C), 147.17, 137.43, 133.22, 132.04, 128.33, 127.67, 125.89, 115.89 (2×CH), 112.40, 101.33, 68.08, 54.48, 54.25, 53.93, 43.60 (3×CH$_2$), 42.50, 41.84, 30.42, 30.07, 29.87, 26.24, 26.14, 25.88, 24.34 (2×CH$_2$), 23.77, 17.68. HRMS (ESI+): calculated for C$_{38}$H$_{63}$N$_{13}$O$_5$[M+H]$^+$ 782.5153, found 782.5142.

Preparation of Compound 59

According to the method for synthesis of compound 38, 44 (38.9 mg, 0.061 mmol), HATU (69.3 mg, 0.182 mmol), (S)—N-((3-(3-fluoro-4-piperazin-1-ylphenyl)-2-oxooxazolidin-5-yl)methyl)-acetamide (40.9 mg, 0.122 mmol), HOBt (27.9 mg, 0.182 mmol), EDC·HCl (35.7 mg, 0.182 mmol) and DIPEA (80.3 μL, 0.486 mmol) used as starting materials were prepared into compound 59 as a yellow gel (23.2 mg, 41%). $^1$H NMR (400 MHz, CD$_3$OD) δ 7.51 (d, J=14.6 Hz, 1H), 7.33 (d, J=8.6 Hz, 2H), 7.18 (d, J=8.9 Hz, 1H), 7.09-7.01 (m, 1H), 6.93 (d, J=6.6 Hz, 2H), 6.28 (d, J=16.4 Hz, 1H), 6.13 (d, J=16.3 Hz, 1H), 5.97-5.82 (m, 1H), 5.16-5.09 (m, 1H), 5.08-4.95 (m, 3H), 4.79-4.46 (m, 3H), 4.11 (t, J=9.2 Hz, 1H), 3.88-3.50 (m, 6H), 3.30-2.84 (m, 10H), 2.05-1.72 (m, 8H), 1.72-1.53 (m, 11H), 1.51-1.43 (m, 2H), 1.20 (s, 3H). $^{13}$C NMR (100 MHz, CD$_3$OD) δ 174.10, 173.42, 171.61, 171.26, 169.98, 158.68, 158.25, 158.24, 156.61, 147.17 (2×CH), 137.43, 137.04, 134.99, 133.22, 132.05, 128.34 (2×CH), 127.67, 125.89 (2×CH), 115.89 (2×CH), 113.39, 112.40, 73.50, 53.95, 50.16, 49.71, 48.34 (2×CH$_2$), 48.33 (2×CH$_2$), 48.32 (2×CH$_2$), 43.60, 43.13, 42.50, 41.91, 41.84, 30.22, 29.92, 25.96, 25.88 (2×CH$_2$), 24.34, 23.78, 22.44, 17.68. HRMS (ESI+): calculated for C$_{48}$H$_{69}$FN$_{12}$O$_7$ [M+H]$^+$ 945.5474, found 945.5457.

Preparation of Compound 60

According to the method for synthesis of compound 44, 44 (52.6 mg, 0.084 mmol), HATU (63.8 mg, 0.168 mmol), H-Arg-Arg-OMe·2HCl (70.1 mg, 0.168 mmol) and DIPEA (55.5 μL, 0.336 mmol) used as starting materials were prepared into compound 60 as a white foam (43.3 mg, 55%). $^1$H NMR (400 MHz, CD$_3$OD) δ 7.32 (d, J=8.7 Hz, 2H), 6.93 (d, J=8.7 Hz, 2H), 6.28 (d, J=16.3 Hz, 1H), 6.12 (d, J=16.3 Hz, 1H), 5.91 (dd, J=17.5, 10.8 Hz, 1H), 5.12 (t, J=7.2 Hz, 1H), 5.06-4.98 (m, 2H), 4.60 (s, 2H), 4.45-4.34 (m, 4H), 3.72 (s, 3H), 3.23-3.15 (m, 8H), 1.99-1.86 (m, 6H), 1.83-1.70 (m, 6H), 1.69-1.61 (m, 9H), 1.57 (s, 3H), 1.51-1.46 (m, 2H), 1.20 (s, 3H). $^{13}$C NMR (100 MHz, CD$_3$OD) δ 174.08, 173.97, 173.86, 173.59, 171.51, 158.68 (2×C), 158.67 (2×C), 158.22, 147.15, 137.40, 133.19, 132.03, 128.32 (2×CH), 127.65, 125.88, 115.87 (2×CH), 112.39, 68.04, 54.39, 54.28, 54.25, 53.36, 52.88, 43.59 (2×CH$_2$), 42.48, 41.92, 41.85, 41.80, 30.16, 29.98, 29.89, 29.40, 26.28, 26.17, 26.15, 26.13, 25.88, 24.33, 23.74, 17.67. HRMS (ESI+): calculated for C$_{45}$H$_{76}$N$_{16}$O$_7$[M+2H]$^2$+477.3120, found 477.3114.

Preparation of Compound 61

According to the method for synthesis of compound 60, 44 (67.2 mg, 0.107 mmol), HATU (101.9 mg, 0.268 mmol), H-Arg-Arg-NH$_2$·2HCl (107.8 mg, 0.268 mmol) and DIPEA (141.8 μL, 0.858 mmol) used as starting materials were prepared into compound 61 as a yellow gel (56.8 mg, 57%). $^1$H NMR (400 MHz, CD$_3$OD) δ 7.33 (d, J=8.8 Hz, 2H), 6.93 (d, J=8.8 Hz, 2H), 6.28 (d, J=16.3 Hz, 1H), 6.12 (d, J=16.3 Hz, 1H), 5.91 (dd, J=17.5, 10.8 Hz, 1H), 5.15-5.09 (m, 1H), 5.06-4.99 (m, 2H), 4.60 (s, 2H), 4.47-4.41 (m, 1H), 4.38-4.31 (m, 3H), 3.22-3.16 (m, 8H), 2.00-1.85 (m, 6H), 1.82-1.72 (m, 4H), 1.70-1.62 (m, 11H), 1.57 (s, 3H), 1.51-1.46 (m, 2H), 1.20 (s, 3H). $^{13}$C NMR (100 MHz, CD$_3$OD) δ 176.35, 174.12, 174.09, 173.89, 171.56, 169.99, 158.69 (4×C), 158.24, 147.16, 137.45, 133.23, 132.04, 128.33 (2×CH), 127.66, 125.89, 115.88 (2×CH), 112.40, 68.08, 54.57, 54.50, 54.39, 54.00, 43.60 (3×CH$_2$), 42.50, 41.89, 41.84, 30.41, 29.99, 29.96, 29.85, 26.31, 26.23, 26.18, 26.12, 25.88, 24.34, 23.76, 17.67. HRMS (ESI+): calculated for C$_{44}$H$_{75}$N$_{17}$O$_6$ [M+2H]$^2$+469.8122, found 469.8108.

Preparation of Compound 63

According to the method for synthesis of compound 38, 45 (47 mg, 0.059 mmol), HATU (67.3 mg, 0.177 mmol), (S)—N-((3-(3-fluoro-4-piperazin-1-ylphenyl)-2-oxooxazolidin-5-yl)methyl)-acetamide (49.6 mg, 0.147 mmol), HOBt (27.1 mg, 0.177 mmol), EDC·HCl (33.8 mg, 0.177 mmol) and DIPEA (78 μL, 0.472 mmol) used as starting materials were prepared into compound 63 as a yellow gel (18.5 mg, 28%). $^1$H NMR (400 MHz, CD$_3$OD) δ 7.53-7.43 (m, 1H), 7.30 (d, J=8.8 Hz, 2H), 7.15 (d, J=8.2 Hz, 1H), 7.03 (t, J=9.1 Hz, 1H), 6.90 (d, J=8.7 Hz, 2H), 6.25 (d, J=16.3 Hz, 1H), 6.09 (d, J=16.3 Hz, 1H), 5.88 (dd, J=17.5, 10.8 Hz, 1H), 5.09 (t, J=7.2 Hz, 1H), 5.03-4.96 (m, 2H), 4.82-4.70 (m, 2H), 4.61-4.53 (m, 2H), 4.47-4.34 (m, 2H), 4.12-4.02 (m, 1H), 3.84-3.64 (m, 4H), 3.55-3.48 (m, 2H), 3.25-3.12 (m, 6H), 3.10-2.82 (m, 5H), 1.97-1.57 (m, 20H), 1.54 (s, 3H), 1.49-1.42 (m, 2H), 1.17 (s, 3H). $^{13}$C NMR (100 MHz, CD$_3$OD) δ 174.08, 173.86, 173.56, 171.62, 171.40, 170.11, 158.71, 158.23, 158.22, 156.60, 155.61, 147.15, 137.45, 133.21, 132.04, 128.33, 127.65, 125.88, 120.91, 115.93, 115.91, 115.57, 115.53, 112.41, 108.60, 108.34, 101.31, 73.47, 68.09, 54.34, 54.14, 52.48, 52.21, 51.13, 51.10, 50.16 (2×CH$_2$), 43.59 (2×CH$_2$), 43.13, 42.48, 41.93, 41.84, 30.12, 30.02, 29.96, 26.19, 26.13, 25.98, 25.88, 24.33, 23.77, 22.46, 17.68.

Preparation of Compound 64

According to the method for synthesis of compound 60, 45 (53.9 mg, 0.068 mmol), HATU (51.4 mg, 0.135 mmol), H-Arg-Arg-Arg-OMe·2HCl (67.7 mg, 0.135 mmol) and DIPEA (67.1 µL, 0.407 mmol) used as starting materials were prepared into compound 64 as a yellow gel (12.9 mg, 16%). $^1$H NMR (400 MHz, CD$_3$OD) δ 7.30 (d, J=8.7 Hz, 2H), 6.90 (d, J=8.7 Hz, 2H), 6.26 (d, J=16.3 Hz, 1H), 6.10 (d, J=16.3 Hz, 1H), 5.88 (dd, J=17.5, 10.8 Hz, 1H), 5.13-5.06 (m, 1H), 5.05-4.95 (m, 2H), 4.58 (s, 2H), 4.42-4.29 (m, 6H), 3.69 (s, 3H), 3.21-3.14 (m, 12H), 1.96-1.82 (m, 8H), 1.80-1.60 (m, 21H), 1.55 (s, 3H), 1.49-1.42 (m, 2H), 1.17 (s, 3H). $^{13}$C NMR (100 MHz, CD$_3$OD) δ 174.26, 174.14, 173.97, 173.60, 173.01, 171.69, 170.23, 158.67 (6×C), 158.22, 147.14, 137.39, 133.16, 132.05, 128.35, 128.33, 127.64, 125.87, 115.84 (2×CH), 112.42, 68.01, 61.55 (5×CH), 53.40, 52.89, 43.60 (5×CH$_2$), 42.48, 41.88, 41.80, 30.17, 30.00, 29.88, 29.68, 29.38, 26.29, 26.18, 25.90 (4×CH$_2$), 24.33, 23.71, 20.88, 17.68, 14.47. HRMS (ESI+): calculated for C$_{57}$H$_{100}$N$_{24}$O$_9$[M+2H]$^{2+}$ 633.4131, found 633.4116.

Evaluation Methods of Biological Experiments

Antibacterial activity assay. The antibacterial activities of all the compounds were determined according to a broth dilution method specified in Clinical and Laboratory Standards Institute (CLSI) guidelines. Bacterial cells were inoculated on a Mueller-Hinton agar (MHA) plate for overnight culture, and the concentration of the bacterial cells was adjusted to about 1×10$^6$ colony-forming units (CFU)/mL with phosphate buffered saline (PBS). First, a 1000 µg/mL stock solution (a final concentration of dimethyl sulfoxide (DMSO) was ≤2%) was prepared by dissolving a sample in DMSO/H$_2$O. Then, the stock solution was diluted with Mueller-Hinton Broth (MHB) to an initial concentration of 100 µg/mL, and the sample solution (100 µL) was subjected to two-fold gradient dilution with MHB in a 96-well plate, to obtain 100 µg/mL to 0.78 µg/mL serial dilutions. Then, a bacterial suspension (100 µL) was added to each well of the 96-well plate and mixed with the test sample solution (100 µL). Among them, test systems for compounds 38, 44-45, 58-61 and 63-64 contained 0.05% of Tween 80. Finally, the 96-well plate was incubated at 37° C. for 24 hours. Absorbances at 600 nm at 0 and 24 h were measured. An minimum inhibitory concentration (MIC) value was defined as the lowest concentration where no visible bacterial growth occurred. All experiments were carried out in at least two duplicates, and biological repeatability could be achieved.

Hemolytic activity assay. Rabbit red blood cells were centrifuged at 2500 rpm for 3 minutes and then washed twice with PBS. Subsequently, a 8% (v/v) cell suspension was prepared by resuspending the rabbit red blood cells with PBS. A sample was first dissolved in DMSO or PBS (a final concentration of DMSO was ≤0.5%), and then diluted with PBS to prepare two-fold gradient dilutions (400 µg/mL to 3.125 µg/mL). The rabbit red blood cell suspension (100 L) was mixed with the two-fold gradient dilutions (100 L) of the sample. Then, the mixture was added to a sterile 96-well plate, incubated at 37° C. for 1 hour, and then centrifuged at 2500 rpm for 5 minutes. Among them, test systems for compounds 38, 44-45, 58-61 and 63-64 contained 0.05% of Tween 80. The supernatant (100 µL) was transferred to a new 96-well plate. Absorbance at 576 nm was measured using a Biotek multifunctional microplate reader. The positive control group was treated with a 2% Triton X-100 solution, and the negative control group was treated with PBS or 0.5% DMSO. The hemolytic activity was calculated by the following equation: % hemolytic activity= [(Abs$_{sample}$−Abs$_{negative\ control}$)/(Abs$_{positive\ control}$−Abs$_{negative\ control}$)]×100. All experiments were carried out in at least two duplicates, and biological repeatability could be achieved.

Assay of toxicity to mammalian cells. The cytotoxicities of a compound to be tested to mouse fibroblasts NCTC clone 929, mouse corneal cells CM120 and human hepatocellular carcinoma cells Hep-G2 were evaluated by a CCK-8 method. Cells were inoculated to a 96-well plate according to the cell amount described in a CCK-8 kit (Beyotime, PRC) specification, and cultured at 37° C. with 5% CO$_2$ for 24 h. Then, a specific concentration of the sample to be tested was added to each well. Inoculation was further performed at 37° C. in an incubator for 24 h. Finally, a CCK-8 solution having a final concentration of 10% was added to each well. Incubation was further performed in the incubator for 1.0 h before absorbance at 450 nm (OD$_{450}$) of the solution was measured by a microplate reader. According to formula (2), the cytotoxicity of the sample to be tested could be obtained:

$$\% \text{ cytotoxicity} = \frac{A_{sample} - A_{blank}}{A_{no\ sample} - A_{blank}} \times 100 \tag{2}$$

A$_{sample}$: absorbance of a well with cells, a CCK8 solution and a sample solution to be tested;

A$_{blank}$: absorbance of a well with a culture medium and a CCK8 solution but without cells; and A$_{no\ sample}$: absorbance of a well with cells and a CCK8 solution but without a sample solution to be tested.

Evaluation of development tendency of drug resistance. Initial MIC values of compound 60, norfloxacin and gatifloxacin against S. aureus ATCC29213 were obtained by the above MIC determination method. Bacterial cells in a 96-well plate with a concentration of 0.5×MIC were taken out to prepare a bacterial suspension (about 1×10$^6$ CFU/mL) for the next MIC value determination. After incubating the sample at 37° C. for 24 hours, the change in the MIC value of each compound was measured. This experiment was carried out consecutively for 15 days.

Evaluation of in vivo efficacy. The experiment for evaluating in vivo antibacterial efficacy of animals had been approved by the Laboratory Animal Center of South China Agricultural University and was carried out according to the policy of the Ministry of Health of the People's Republic of China. Female C57BL6 mice (6-8 weeks, with an average weight of 20 g) were used as a bacterial keratitis model. In order to establish an immunosuppressive mouse model, cyclophosphamide (100 mg/kg) was injected intraperitoneally to mice three times 5 days before infection. Bacterial cells (S. aureus ATCC 29213) inoculated onto a Mueller Hinton agar (MHA) plate were suspended with PBS, and the concentration of the bacterial cells was adjusted to about 5×10$^7$ CFU/mL for corneal infection in mice. First, the mice were anesthetized. Then, the cornea of the left eye of the mouse was scratched with a sterile needle, and 15 µL of bacterial suspension was dropped on the injured cornea. One day after infection, the mice were randomized into three groups (5 mice per group). Three compounds (0.5% 60, 5% glucose solution and 5% vancomycin) were applied topically four times a day for consecutive three days, respectively. Finally, the mice were euthanized, and their corneas were collected. Viable bacteria were counted by an MHA plate counting method. the P value was calculated using SPSS 22.0 software and P≤0.05 was considered as being statistically significant.

CD-1 mice (6-8 weeks, with an average weight of 25 g) were used as an abdominal infection model. First, the mice were injected with S. aureus ATCC29213 ($OD_{600} \approx 1.0$) intraperitoneally, and the mice were randomized into three groups (5 mice per group). After 1 hour of infection, one group was dosed with 58 (5 mg/kg) intravenously for treatment, once every 4 hours; and meanwhile, one group dosed with vancomycin (20 mg/kg, IP) was used as a positive control group, and the other group dosed with a 0.9% sodium chloride injection was used as a blank control group. After two days of treatment, the survival rate of the mice was investigated.

Experimental Results

Results of in vitro antibacterial activities of the bakuchiol derivatives are shown in tables 1 and 2.

Among them, compounds 5, 6, 9, 11-16, 23-35, 38, 39, 44, 45, 49, 51-53 and 58-64 show excellent antibacterial activities against Gram-positive bacteria, with the minimum inhibitory concentration (MIC) being 0.39-3.125 μg/mL. Compounds 23, 24, 26-30, 44, 59 and 63 exhibit broad-spectrum antibacterial activities and also show excellent antibacterial activities against Gram-negative bacteria, with the MIC value being 1.56-3.125 μg/mL.

TABLE 1

In vitro antibacterial activities of bakuchiol derivatives 5-29 (μg/mL)

| | MIC (μg/mL) | | | |
|---|---|---|---|---|
| Compd | S. aureus ATCC29213 | E. coli ATCC25922 | MRSA N315 | MRSA NCTC10442 |
| 5 | 1.56 | >50 | 1.56 | 3.125 |
| 6 | 3.125 | >100 | 3.125 | 3.125 |
| 8 | 6.25 | >100 | 6.25 | 6.25 |
| 9 | 3.125 | >100 | 3.125 | 3.125 |
| 11 | 3.125 | >100 | 1.56 | 1.56 |
| 12 | 12.5 | >100 | 3.125 | 3.125 |
| 13 | 1.56 | 12.5 | 0.78 | 1.56 |
| 14 | 1.56 | 12.5 | 0.78 | 1.56 |
| 15 | 1.56 | 12.5 | 1.56 | 1.56 |
| 16 | 1.56 | 100 | 0.78 | 1.56 |
| 17 | 6.25 | >100 | 1.56 | 3.125 |
| 18 | 50 | >100 | 12.5 | 50 |
| 20 | 1.56 | >100 | 1.56 | 1.56 |
| 21 | 1.56 | >100 | 3.125 | 3.125 |
| 22 | 3.125 | >100 | 1.56 | 1.56 |
| 23 | 1.56 | 3.125 | 0.78 | 3.125 |
| 24 | 1.56 | 1.56 | 0.78 | 1.56 |
| 25 | 0.78 | 50 | 0.78 | 1.56 |
| 26 | 1.56 | 3.125 | 1.56 | 3.125 |
| 27 | 1.56 | 1.56 | 0.78 | 1.56 |
| 28 | 1.56 | 3.125 | 1.56 | 1.56 |
| 29 | 0.78 | 3.125 | 0.78 | 0.78 |
| 30 | 0.78 | 3.125 | 0.78 | 0.78 |

TABLE 2

In vitro antibacterial activities of bakuchiol derivatives 30-64 (μg/mL)

| | MIC (μg/mL) | | | |
|---|---|---|---|---|
| Compd | S. aureus ATCC29213 | E. coli ATCC25922 | MRSA N315 | MRSA NCTC10442 |
| 31 | 1.56 | 6.25 | 0.78 | 1.56 |
| 32 | 0.78 | 6.25 | 0.78 | 0.78 |
| 33 | 1.56 | 12.5 | 0.39 | 0.78 |
| 34 | 1.56 | 6.25 | 0.78 | 0.39 |
| 35 | 3.125 | 25 | 1.56 | 3.125 |
| 38 | 0.78 | 6.25 | 1.56 | 0.78 |
| 39 | 3.125 | 12.5 | 3.125 | 3.125 |
| 40 | 6.25 | >100 | 6.25 | 6.25 |

TABLE 2-continued

In vitro antibacterial activities of bakuchiol derivatives 30-64 (μg/mL)

| | MIC (μg/mL) | | | |
|---|---|---|---|---|
| Compd | S. aureus ATCC29213 | E. coli ATCC25922 | MRSA N315 | MRSA NCTC10442 |
| 44 | 0.78 | 3.125 | 0.78 | 1.56 |
| 45 | 0.39 | 6.25 | 0.78 | 1.56 |
| 47 | 6.25 | 12.5 | 6.25 | 6.25 |
| 49 | 1.56 | 12.5 | 3.125 | 1.56 |
| 50 | 6.25 | 12.5 | 6.25 | 6.25 |
| 51 | 1.56 | 6.25 | 1.56 | 3.125 |
| 52 | 1.56 | 25 | 0.78 | 0.78 |
| 53 | 0.78 | 6.25 | 0.78 | 0.78 |
| 55 | 12.5 | >100 | 12.5 | 12.5 |
| 56 | 6.25 | 25 | 6.25 | 6.25 |
| 58 | 0.39 | 12.5 | 0.39 | 0.39 |
| 59 | 0.78 | 1.56 | 0.78 | 0.78 |
| 60 | 0.39 | 12.5 | 0.39 | 0.78 |
| 61 | 0.78 | 25 | 0.39 | 0.78 |
| 63 | 0.78 | 3.125 | 0.78 | 0.78 |
| 64 | 1.56 | 25 | 1.56 | 1.56 |

Research Results of In Vitro Cytotoxicity and Hemolytic Activity

Active compounds 44 and 60 at 100 μg/mL show no obvious cytotoxicity to mouse corneal cells, with the cell survival rate being still kept at more than 900%. Active compounds 58 and 60 at 100 μg/mL show no obvious cytotoxicity to mouse fibroblasts NCTC clone 929, with the cell survival rate being still kept at 89.3±0.600 and 93.7±0.700, respectively.

The hemolytic toxicities of active compounds 45, 53, 58, 60, 61, 64 and 63 are very low, with the HC50 values (the concentration of a compound necessary to lyse 50% rabbit red blood cells) being all more than 400 μg/mL. The hemolytic toxicity of active compound 28 is also relatively low, with the HC50 value being 112.9±5.0 μg/mL. The above results show that these bakuchiol compounds have comparatively high safety.

Research Results of Drug Resistance

Overcoming the generation of drug resistance of bacteria has become one of the most important indicators for evaluating new antibacterial compounds. As shown in FIG. 1, after 15 days of continuous passage, the MIC value of compound 60 does not change significantly. However, obvious drug resistance to norfloxacin is produced, and there is a 16-fold increase in the MIC value after 15 days of continuous passage. These results show that compound 60 can effectively overcome the generation of drug resistance of bacteria.

Evaluation Results of In Vivo Antibacterial Activity

Figure 2:
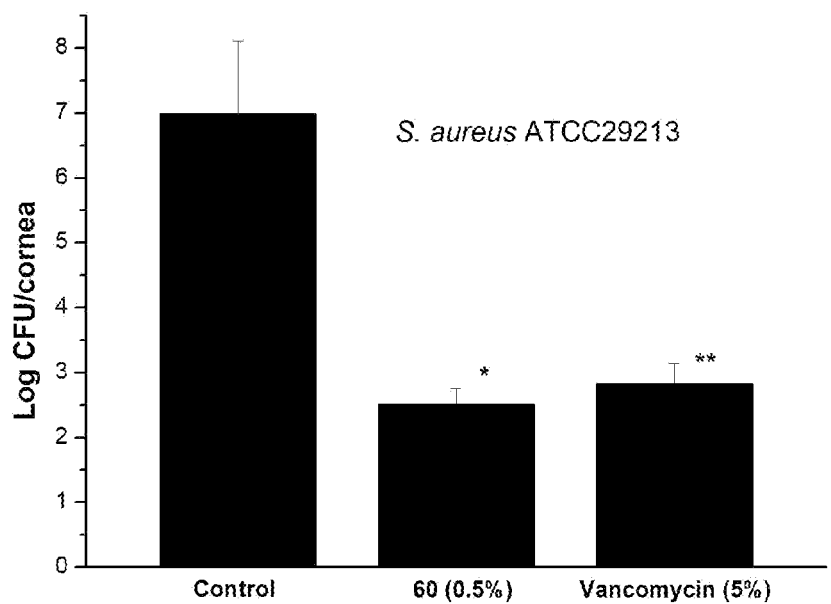
FIG. 2 is a bar graph showing in vivo antibacterial efficacy of the compound 60 in a mouse model of cornea infection caused by S. aureus ATCC29213.

Compounds 58 and 60 show excellent in vitro antibacterial activities against Gram-positive bacteria as well as very low hemolytic activities and cytotoxicities. In a mouse model of bacterial keratitis caused by S. aureus ATCC29213, as shown in FIG. 2, the topical use of 0.5% compound 60 and 5% vancomycin reduces the number of bacteria in the infected mouse cornea by 4.48 log (P<0.01) and 4.16 log (P<0.01), respectively. In a mouse model of bacterial peritonitis caused by S. aureus ATCC29213, after two days of treatment, all five mice in the negative control group die. However, all five mice in each of the compound 58 treatment group and the vancomycin positive control group survive, with the survival rate being 100%. Compounds 58 and 60 show excellent in vivo antibacterial efficacy, which is comparable to vancomycin. These results show that compounds 58 and 60 can cure the bacterial infection caused by S. aureus.

It can be seen that compound 60 shows an excellent antibacterial effect in the mouse model of corneal infection caused by *S. aureus* ATCC29213 (administrated topically); and 58 shows excellent pharmacokinetic characteristics in mice, and shows excellent antibacterial efficacy in the mouse model of abdominal infection (administrated subcutaneously, intraperitoneally and intravenously, respectively). Such bakuchiol derivatives based on new molecular entities and new antibacterial mechanisms can effectively fight against drug-resistant bacterial infections, providing a new solution to the current antibiotic resistance crisis.

The technical features of the above embodiments may be arbitrarily combined. For brevity of description, all possible combinations of the technical features in the above embodiments are not described. However, as long as there is no contradiction between the combinations of these technical features, all these combinations should be considered as the scope of this specification.

The above embodiments are only used to express several implementations of the disclosure and are specifically described in details, but they cannot be understood therefore as limiting the patent scope of the disclosure. It should be pointed out that for those skilled in the art, without departing from the concept of the disclosure, a number of variations and improvements could be made, which are all within the scope of protection of the disclosure. Therefore, the scope of patent protection of the disclosure shall be on the basis of the appended claims.

The invention claimed is:

1. A bakuchiol derivative and a pharmaceutically acceptable salt thereof, selected from a compound of any of the following general formulae:

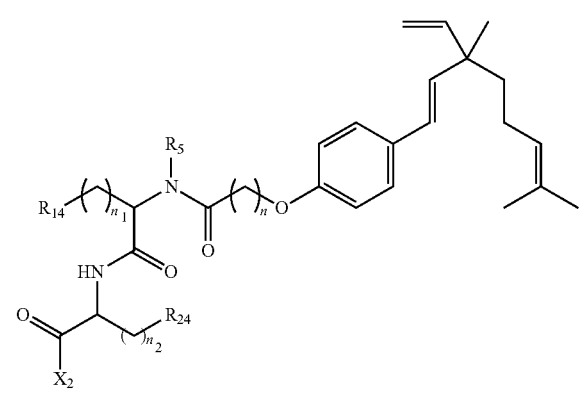

(III)

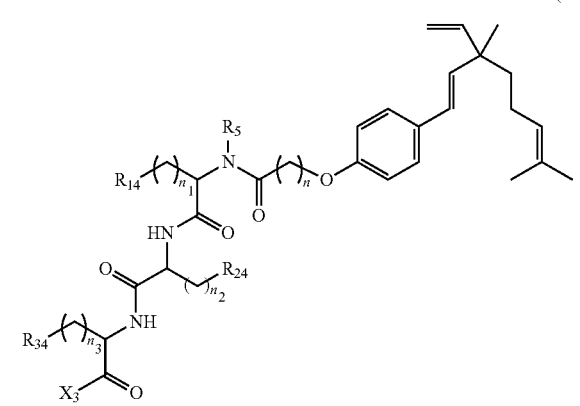

(IV)

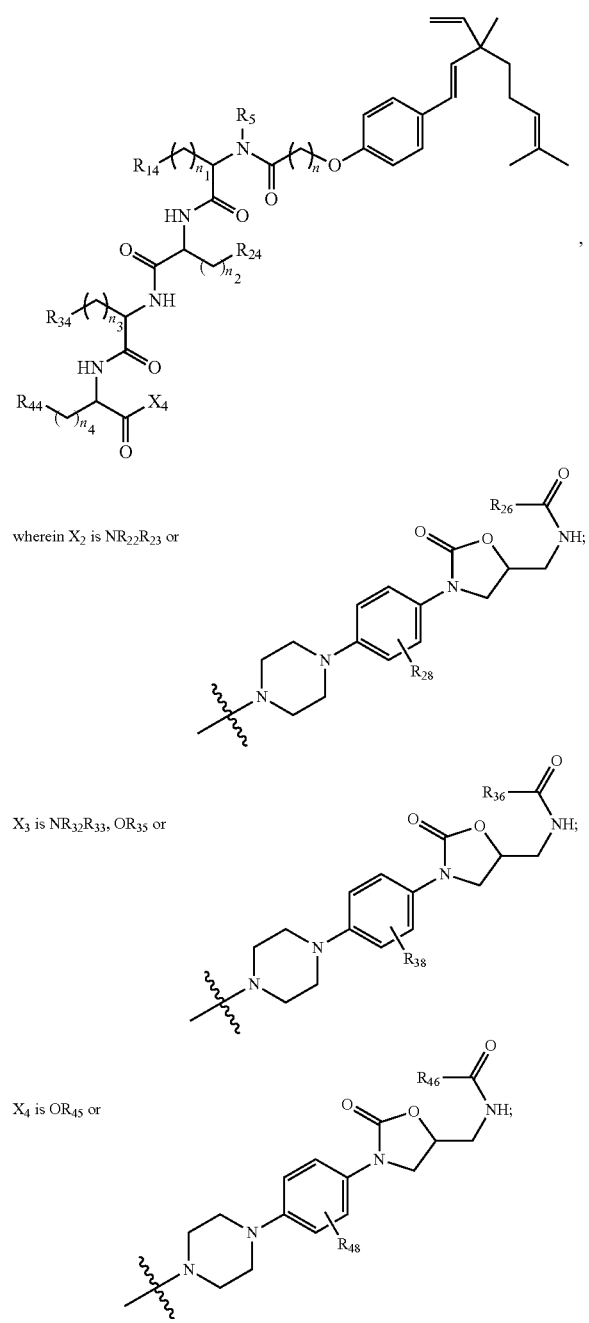

(V)

wherein $X_2$ is $NR_{22}R_{23}$ or $X_3$ is $NR_{32}R_{33}$, $OR_{35}$ or $X_4$ is $OR_{45}$ or $R_{22}$ and $R_{23}$ are each independently selected from: —H;

$R_{32}$ and $R_{33}$ are each independently selected from: —H;

wherein $R_{14}$, $R_{24}$, $R_{34}$ and $R_{44}$ are each independently selected from: guanidyl, —$NR_4R_5$ or 5- to 20-membered nitrogen-containing heteroaryl;

$R_4$ and $R_5$ are each independently selected from: —H;

$R_{26}$, $R_{35}$, $R_{36}$, $R_{45}$ and $R_{46}$ are each independently selected from: $C_{1-6}$ alkyl;

$R_{28}$, $R_{38}$ and $R_{48}$ are each independently selected from: —H or halogen;

each of $n_1$, $n_2$, $n_3$ and $n_4$ is independently 0, 1, 2, 3 or 4;

n is an integer from 1 to 10.

2. The bakuchiol derivative and a pharmaceutically acceptable salt thereof according to claim 1, selected from a compound of any of the following general formulae:

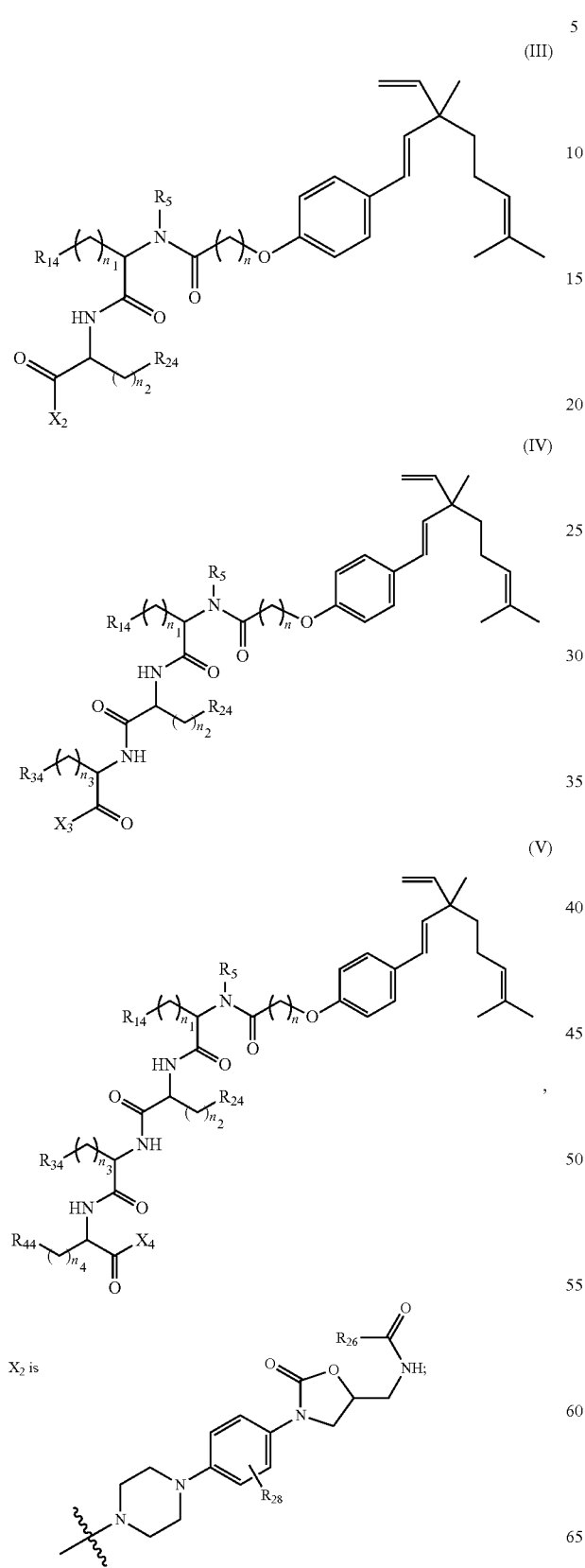

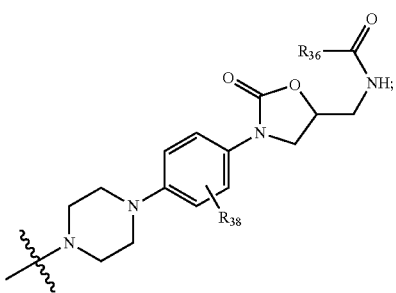

$X_3$ is

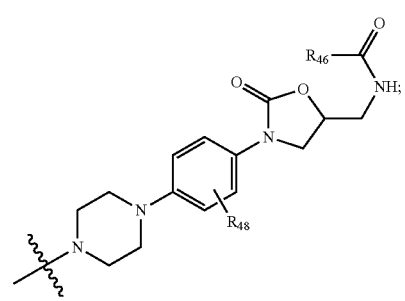

$X_4$ is

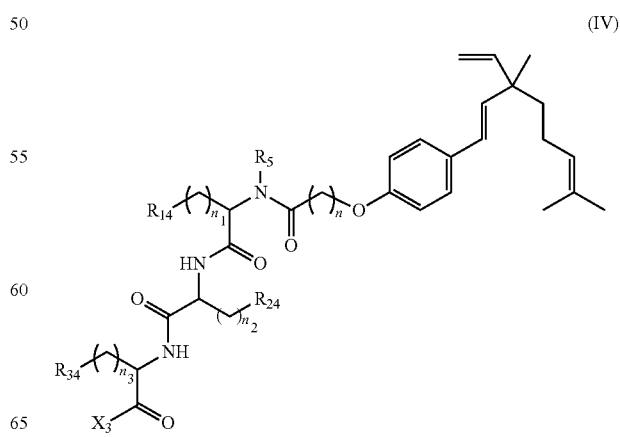

wherein $R_{14}$, $R_{24}$, $R_{34}$ and $R_{44}$ are each independently selected from: guanidyl, —$NR_4R_5$ or 5- to 20-membered nitrogen-containing heteroaryl;

$R_4$ and $R_5$ are each independently selected from: —H;

$R_{26}$, $R_{36}$ and $R_{46}$ are each independently selected from: $C_{1-6}$ alkyl;

$R_{28}$, $R_{38}$ and $R_{48}$ are each independently selected from: —H or halogen;

each of $n_1$, $n_2$, $n_3$ and $n_4$ is independently 0, 1, 2, 3 or 4;

n is an integer from 1 to 10.

3. The bakuchiol derivative and a pharmaceutically acceptable salt thereof according to claim 1, selected from a compound of any of the following general formulae:

-continued

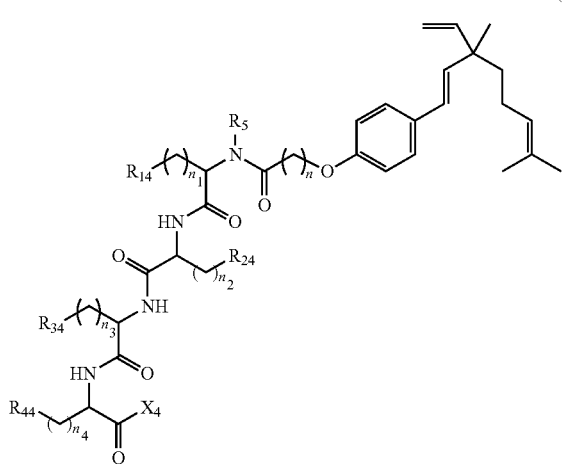

(V)

$X_3$ is $OR_{35}$; $X_4$ is $OR_{45}$;
wherein $R_{14}$, $R_{24}$, $R_{34}$ and $R_{44}$ are each independently selected from: guanidyl, —$NR_4R_5$ or 5- to 20-membered nitrogen-containing heteroaryl;
$R_{35}$ and $R_{45}$ are each independently selected from: $C_{1-6}$ alkyl;
each of $n_1$, $n_2$, $n_3$ and $n_4$ is independently 0, 1, 2, 3 or 4;
n is an integer from 1 to 10.

4. The bakuchiol derivative and a pharmaceutically acceptable salt thereof according to claim 1, selected from a compound of any of the following general formulae:

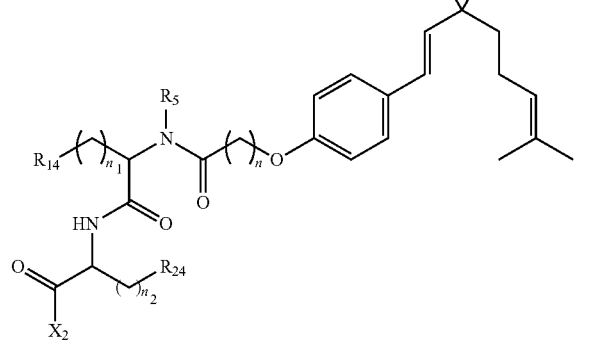

(III)

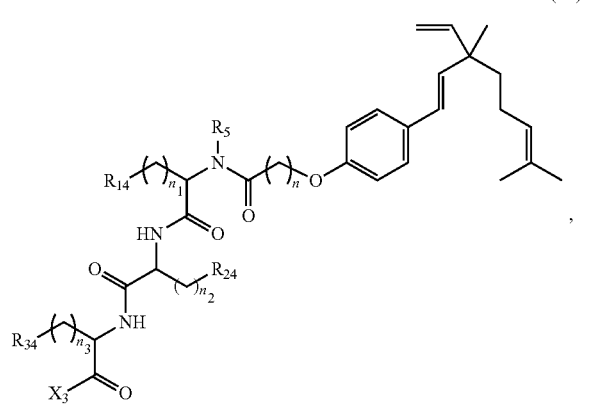

(IV)

wherein $X_2$ is $NR_{22}R_{23}$; $X_3$ is $NR_{32}R_{33}$;
$R_{22}$ and $R_{23}$ are each independently selected from: —H;
$R_{32}$ and $R_{33}$ are each independently selected from: —H;
wherein $R_{14}$, $R_{24}$ and $R_{34}$ are each independently selected from: guanidyl, —$NR_4R_5$ or 5- to 20-membered nitrogen-containing heteroaryl;
$R_4$ and $R_5$ are each independently selected from: —H;
each of $n_1$, $n_2$, $n_3$ and $n_4$ is independently 0, 1, 2, 3 or 4;
n is an integer from 1 to 10.

5. The bakuchiol derivative and a pharmaceutically acceptable salt thereof according to claim 1, wherein $R_{14}$, $R_{24}$, $R_{34}$ and $R_{44}$ are each independently selected from: guanidyl, —$NR_4R_5$, —$SR_4$, 5-membered nitrogen-containing heteroaryl.

6. The bakuchiol derivative and a pharmaceutically acceptable salt thereof according to claim 1, selected from a compound of the following general formula:

(II')

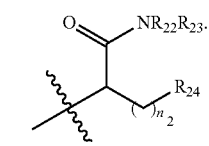

wherein X is $NR_{12}R_{13}$;
one of $R_{12}$ and $R_{13}$ is H, and another one is selected from

7. The bakuchiol derivative and a pharmaceutically acceptable salt thereof according to claim 1, selected from the following compounds:

compound 45
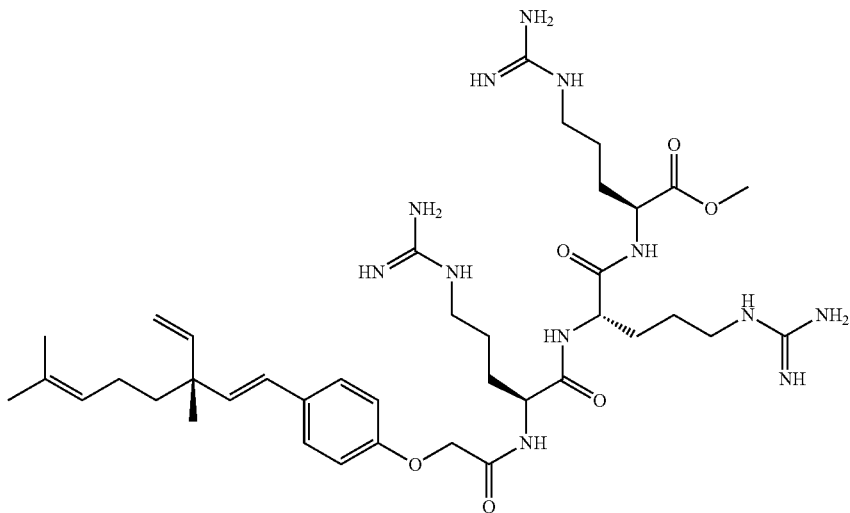
compound 49
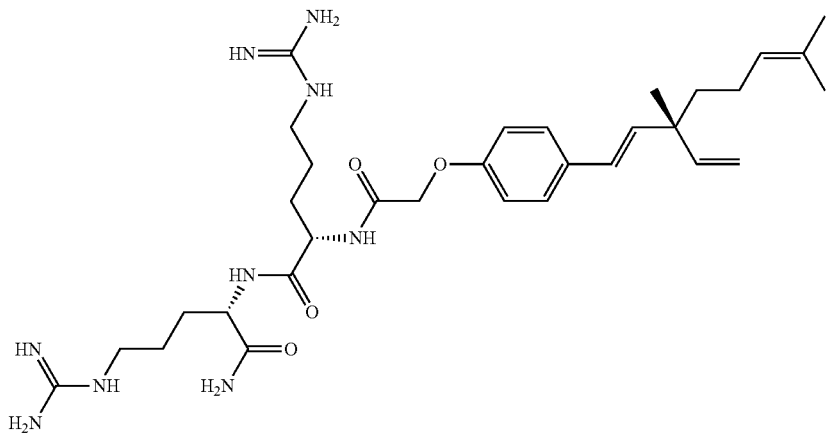
compound 58
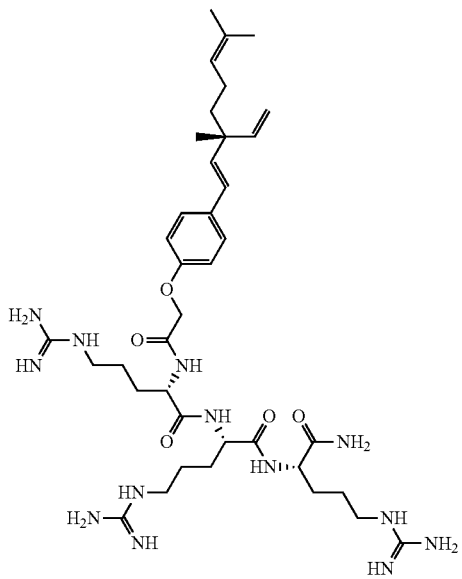
compound 59
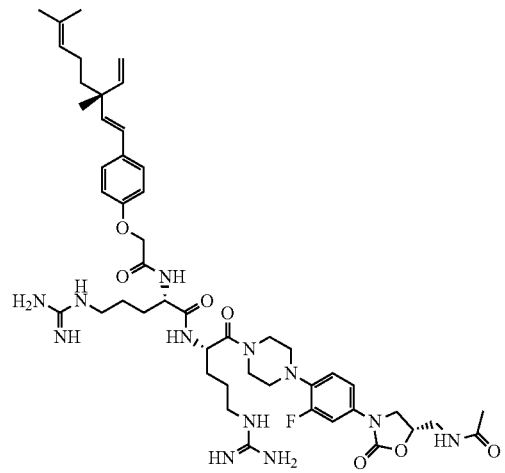

-continued
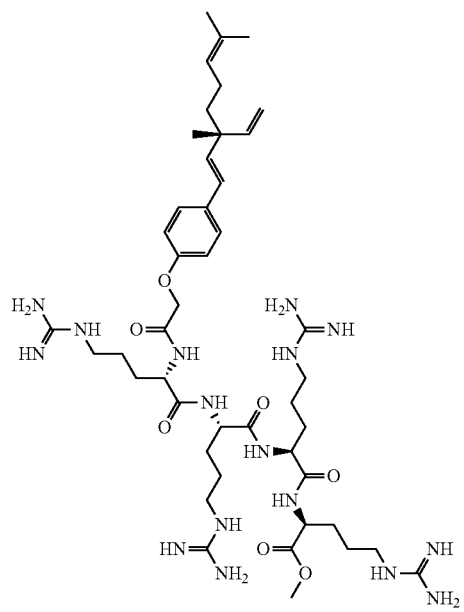
compound 60
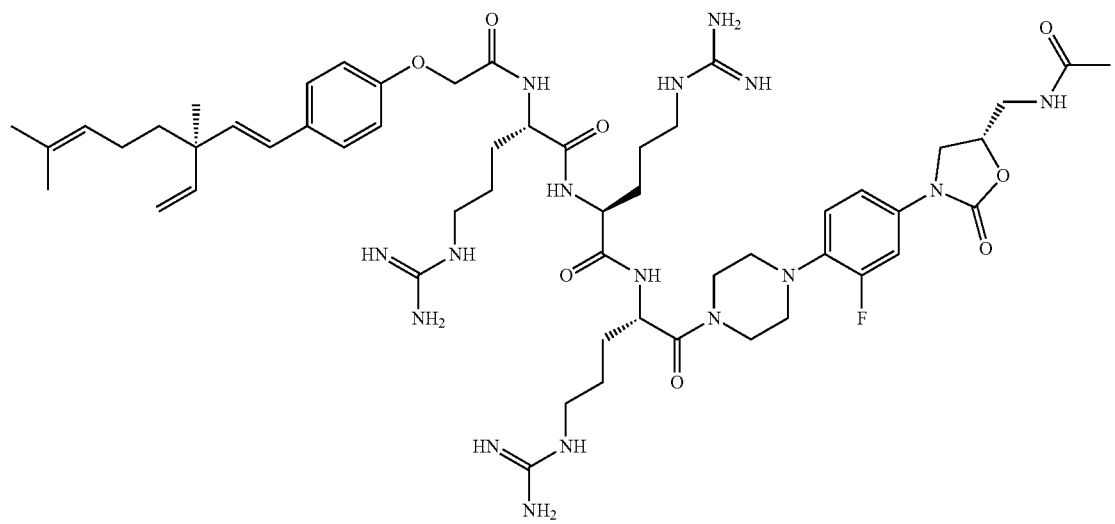
compound 63
8. A preparation method of the bakuchiol derivative and a pharmaceutically acceptable salt thereof of claim 1, wherein the preparation method comprises the following step:
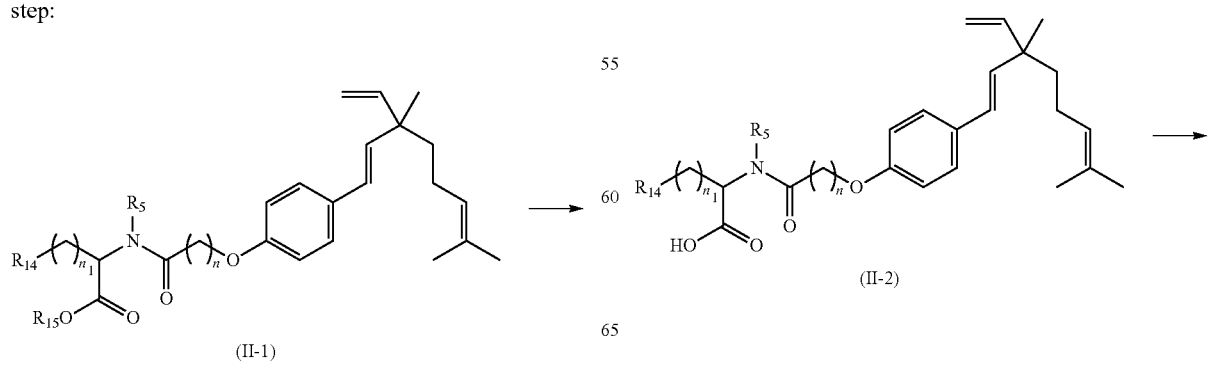

-continued

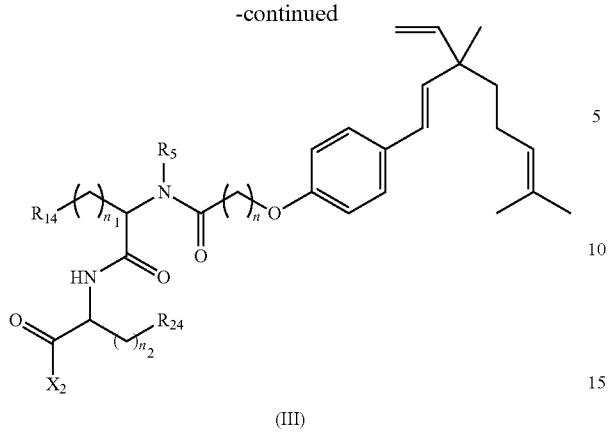

(III)

performing a hydrolysis reaction on a compound shown in formula (II-1), to obtain a compound shown in formula (II-2);

performing a condensation reaction on the compound shown in formula (II-2) and

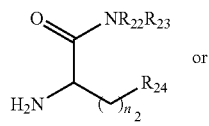 or

-continued

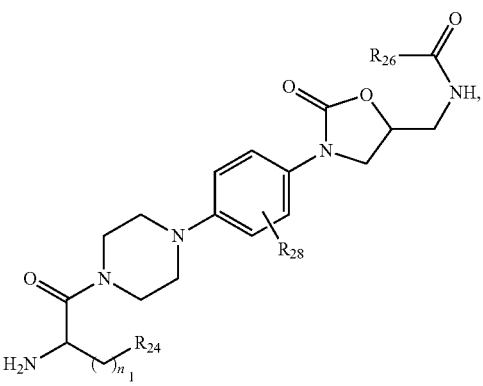

to obtain a compound shown in formula (III); and $R_{15}$ is defined as $R_{35}$ in claim 1.

9. A pharmaceutical composition comprising at least one of the bakuchiol derivative and a pharmaceutically acceptable salt thereof of claim 1, and a pharmaceutically acceptable excipient.

* * * * *